United States Patent [19]
Scarborough et al.

[11] Patent Number: 5,958,732
[45] Date of Patent: *Sep. 28, 1999

[54] PLATELET AGGREGATION INHIBITORS

[75] Inventors: Robert M. Scarborough, Belmont; David Lawrence Wolf, Palo Alto; Israel F. Charo, Lafayette, all of Calif.

[73] Assignee: COR Therapeutics, Inc., South San Francisco, Calif.

[*] Notice: This patent is subject to a terminal disclaimer.

[21] Appl. No.: 08/474,249

[22] Filed: Jun. 7, 1995

Related U.S. Application Data

[63] Continuation of application No. 08/067,139, May 24, 1993, abandoned, which is a continuation of application No. 07/483,229, Feb. 20, 1990, Pat. No. 5,318,899, which is a continuation-in-part of application No. 07/418,028, Oct. 16, 1989, abandoned, which is a continuation-in-part of application No. 07/367,509, Jun. 16, 1989, abandoned.

[51] Int. Cl.$^6$ .............................. C12P 21/06; C12N 5/00; C12N 15/00; C07K 17/00
[52] U.S. Cl. .................... 435/69.2; 435/325; 435/252.3; 435/320.1; 536/23.5
[58] Field of Search ............................... 435/69.1, 320.1, 435/240.1, 69.2, 325, 252.3; 536/23.1, 23.5; 530/300

[56] References Cited

U.S. PATENT DOCUMENTS

| | | | |
|---|---|---|---|
| 4,517,686 | 5/1985 | Ruoslahti et al. | 3/1 |
| 4,578,079 | 3/1986 | Ruoslahti et al. | 623/11 |
| 4,589,881 | 5/1986 | Pierschbacher et al. | 623/11 |
| 4,614,517 | 9/1986 | Ruoslahti et al. | 623/11 |
| 4,661,111 | 4/1987 | Ruoslahti et al. | 623/11 |
| 4,661,471 | 4/1987 | Hawiger et al. | 514/13 |
| 4,792,525 | 12/1988 | Ruoslahti et al. | 435/240.243 |
| 5,318,899 | 6/1994 | Scarborough et al. | 435/69.6 |
| 5,496,724 | 3/1996 | Scarborough et al. | 435/252.3 |

FOREIGN PATENT DOCUMENTS

| | | |
|---|---|---|
| 0 314 576 | 3/1987 | European Pat. Off. |
| 0 298 820 | 5/1987 | European Pat. Off. |
| 0 291 804 A2 | 5/1988 | European Pat. Off. |
| 0 317 053 A2 | 8/1988 | European Pat. Off. |
| 0 319 506 A2 | 12/1988 | European Pat. Off. |
| 0 341 915 A2 | 5/1989 | European Pat. Off. |
| 2 207 922 | 8/1987 | United Kingdom . |
| 88/03151 | 10/1987 | WIPO . |
| WO 89/07609 | 1/1989 | WIPO . |

OTHER PUBLICATIONS

Ali et al., *Structure–Activity Studies Toward the Improvement of Antiaggregatory Activity of Arg–Gly–Asp–Ser (RGDS) Peptides: Chemistry, Structure and Biology* (Proceedings of the 11th American Peptide Symposium), Marshall, G.R. and River, J.E. editors, ESCOM, Leiden (1990) pp. 94–96.

Bennett et al., *Inhibition of Fibrinogen Binding Stimulated Human Platelets by a Monoclonal Antibody*, Proc. Natl. Acad. Sci., 80:2417–2421 (1983).

Cadroy et al., *RGDV Peptide Selectivily Inhibits Platelet–Dependent Thrombus FOrmation In Vivo*, J. clin. Invest., 84:939–944 (1989).

Chao et al., *Applaggin: A Potent Inhibitor of Platelet Aggregation and Secretion*, Thrombosis and Haemostasis, 672(1):50, Abstract No. 120 (1989).

Chao et al., *Agkistrodon Piscivorus Platelet Aggregatin Inhibitor: A Potent Inhibitor of Platelet Activation*, Proc. Natl. Acad. Sci., 86:8050–8054 (1989).

Dennis et al., *Platelet Glycoprotein IIb–IIIa Protein Antagonists from Snake Venoms: Evidence for a Family of Platelet–Aggregation Inhibitors*, Proc. Natl. Acad. Sci., 87:2471–1475 (1989).

Gan et al., *Echistatin, A Potent Platelet Aggregation Inhibitor from the Venom of the Viper, Echis Carinatus*, J. Biol. Chem., 263(36):1982–1987 (1988).

(List continued on next page.)

Primary Examiner—Karen Cochrane Carlson
Attorney, Agent, or Firm—Cooley Godward LLP

[57] ABSTRACT

An assay for screening snake venom for the presence or absence of platelet aggregation inhibitors (PAIs) based on specific receptor binding is described. Using this assay, the identification and characterization of PAIs in a wide range of snake venom samples was accomplished. The isolated and purified PAI from several of these active snake venoms is described and characterized. In addition, PAIs lacking the Arg-Gly-Asp (RGD) adhesion sequence but containing K*-(G/Sar)-D wherein K* is a modified lysyl residue of the formula

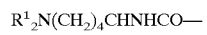

wherein each $R^1$ is independently H, alkyl(1–6C) or at most one $R^1$ is $R^2$—C=$NR^3$ wherein $R^2$ is H, alkyl(1–6C) or is $NR^4_2$ in which each $R^4$ is independently H or alkyl(1–6C) and $R^3$ is H, alkyl(1–6C), phenyl or benzyl, or $R^2$—C=$NR^3$ is a radical selected from the group consisting of:

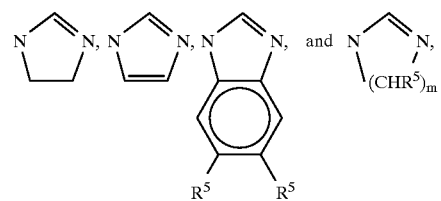

where m is an integer of 2–3, and each $R^5$ is independently H or alkyl(1–6C);

and wherein one or two ($CH_2$) may be replaced by O or S provided said O or S is not adjacent to another heteroatom are prepared and shown to specifically inhibit the binding of fibrinogen or von Willebrand Factor to GP IIb–IIIa.

12 Claims, 47 Drawing Sheets

OTHER PUBLICATIONS

Garsky et al., *Chemical Synthesis of Echistatin, A Potent Inhibitor of Platelet Aggregtion from Echis Carinatus: Synthesis and Biological Activity of Selected Analogs,* Proc. Natl. Acad. Sci., 86:4022–4026 (1989).

Huang et al., *Trigramin A Low Molecular Weight Peptide Inhibiting Fibrinogen Interaction with Platelet Receptor Expressed on Glycoprotein IIb–IIIa Complex,* J. Biol. Chem., 262(33):16157–16163 (1987).

Huang et al., *Trigramin: Primary Structure and Its Inhibition of von Willebrand Factor Binding to Glycoprotein IIb/IIIa Complex on Human Platelets,* Biochemistry, 28:661–666 (1989).

Huang et al., *Halysin, A Potent Platelet Aggregation Inhibitor, Inhibits the Fibrinogen Binding to the Activated Platelets,* Thrombosis and Haemostasis 62(1):48, Abstract No. 112 (1989).

Kloczewiak et al., *Platelet Receptor Recognition Domain on the γ Chain of Human Fibrinogen and Its Synthetic Peptide Analogues,* Biochemistry, 28:2915–2919 (1989).

Knudsen et al., *Trigramin, an RGD–Containing Peptide from Snake Venom, Inhibits Cell–Sbustratum Adhesion of Human Melanoma Cells,* Exerimental Cell Research, 179:42–49 (1988).

Nachman et al., *Complex Formation of Platelet Membrane Glycoproteins IIb and IIIa with Fibrinogen,* Amer, Soc. for Clin. Invest., 69:263–269 (1982).

Niewiarowski et al., *Potential Application of RGD Containing Peptides from Viper Venoms (Disentegrins) in Antiplatelet Therapy,* Thrombosis and Haemostatis, 62(1):319, Abstract No. SY–XIV–5 (1989).

Phillips et al., *The Platelet Membrane Glycoprotein IIb–IIIa Complex,* Blood, 71:831–843 (1988).

Pierschbacher et al., *Influence of Stereochemistry of the Sequence Arg–Asp–Xaa on Binding Specificity in Cell Adhesion,* J. Biol. Chem., 262:17294–17298 (1987).

Ruggeri et al., *Inhibition of Platelet Function With Synthetic Peptides Designed to be High–Affinity Antagonists of Fibrinogen Binding to Platelets;* Proc. Natl. Acad. Sci. USA, 83:5708–5712 (1986).

Ruckinski et al., *Batroxostatin, A RGD Containing Peptide from B. Atrox Venom, is a Potent Inhibitor of Cell Interaction with Adhesive Proteins,* Thrombosis and Haemostasis, 62:50, Abstract No. 1560 (1989).

Ruoslahti et al., *New Perspectives in Cell Adhesion: RGD and Integrins,* Science, 238:491–497 (1987).

Ruoslahti et al., *Arg–Gly–Asr: A Versatile Cell Recognition Signal,* Cell, 44:517–518 (1986).

Samanen et al., *An RGD–Peptide Analog with Potent Antithrombotic Activity In Vivo,* J. Cell. Biol. Supplement 14A:A229 (1990).

Shebuski et al., *Characterization and Platelet Inhibitory Activity of Bitistatin, a Potent Arginine–Glycine–Aspartic Acid–containing Peptide from the Venom of the Viper Bitis arietans,* J. Biol. Chem., 264(36):21550–21556 (1989).

Timmons et al., *Antiplatelet "Hybrid" Peptide Analagous to Receptor Recognition Domains on γ and a α Chains of Human Fibrinogen,* Biochemistry, 28:2919–2923 (1989).

Tranqui et al., *Differential Structural Requirements for Fibrinogen Binding to Platelets and Endothelial Cells,* J. Cell Biol., 108:2519–2527 (1989).

Williams et al., *Purification and Amino Acid Sequence of Two RGD–Containing Peptides from the Venoms of T. Elegans and T. Albolaris, Platelets,* FASEB Journal p. 310, Abstract No. 487.

Yasuda et al, *Monoclonal Antibody Against the Platelet Glycoprotein (GP) IIb/IIIa Receptor Prevents Coronary Artery Reocclusion After Reperfusion with Recombinant Tissue–Type Plasminogen Activator in Dogs,* J. Clin. Invest. 81:1284–1291 (1988).

11th American Peptide Symposia, San Diego, California, Jul. 9–14, 1989.

(K)= fragments from endoproteinase Lys-C digestion (D)= fragments from endoproteinase Asp-N digestion

[Z]= fragment from pyroglutamyl aminopeptidase digestion

```
                                                              Eristicophin
ZRQEEPCATGPCCRRCKFKRAGKVCRVARGDWNNDYCTGKSCDCPRNPWNG

|<----------------->                               [Z]
          |--|    |<----------------->|<---------->|   (K)
|<--------------------------->|<->|<-------->|<------>|   (D)
```

```
                                                              Barbourin
EAGEECDCGSPENPCCDAATCKLRPGAQCADGLCCDQCRFMKKGTVCRVAKGDWNDDTCTGQSADCPRNGLYG

|<----------------------->                                         N-term
              |<------------------>|<------------------------>|
                                         |<------------------------>|  (K)
    |<----------->|    |<------------>|                  |<------>|  (D)
```

```
                                                              Tergeminin
EAGEECDCGSPANPCCDAATCKLRPGAQCADGLCCDQCRFMKKGTVCRVARGDWNDDTCTGQSADCPRNGLYG

|<----------------------->                                         N-term
              |<---------------->| |<------------------------------>|  (K)
                      |<-------------->|                              (D)
```

```
                                                              Cerastin
EAGEECDCGTPENPCCDAATCKLRPGAQCADGLCCDQCRFMKKGTVCRVARGDWNDDTCTGQSADCPRNGLYG

|<------------------------------------------>|                     N-term
              |<-------------->|<--------------------------------->|
                                 |<--------------------------->|   (K)
        |<------->|<--->|<------------------>|<--->|    |<------>|  (D)
```

FIG. 6A

```
                                                                        Ruberin
EAGIECDCGSLENPCCDAATCKLRPGAQCADGLCCDQCRFIKKGTVCRPARGDWNDDTCTGQSADCPRNGLYG

|<--------------------------------------------------->|                 N-term
                    |<----------------------------------------->|       (K)

Lachesin
EAGEECDCGAPANPCCDAATCKLRPGAQCAEGLCCDQCRFIKKGKICRRARGDNPDDRCTGQSADCPRNGYYG

|<-------------------->|                                                N-term
           |<------------->|    |<------------------------->|           (K)
      |<---------------->|<---->|                |<-------->|           (D)

Cotiarin
EAGEECDCGAPENPCCDAATCKLRPCAQCAEGLCCDQCRFKGAGKICRRARGDNPDDRCTGQSADCPRNRF(H)

|<------------------------------------------------------->|             N-term
           |<------------->|    |<------------------------->|           (K)
|<-------->|                    |<------------->|    |<--------->|      (D)

Crotatroxin
AGEECDCGSPANPCCDAATCKLRPGAQCADGLCCDQCRFIKKGTVCRPARGDWNDDTCTGQSADCPRNGLYG

|<------------------------------------->|                               N-term
|<--------------->|<--------------->| |<------------------------->      (K)
      |<-------->|   |<------------->|            |<-------->|          (D)

Horridin
EAGEECDCGSPANPCCDAATCKLRPGAQCADGLCCDQCRFIKKGKICRRARGDNPNDRCTGQSADCPRNRFH

|<--------------------------------------------->|                       N-term
           |<------------->|    |<------------------------->|           (K)
```

FIG. 6B

```
                                                                              Lutosin
EAGEECDCGSPANPCCDAATCKLRPGAQCADGLCCDQCRFIKKGTVCRVARGDWNDDTCTGQSADCPRNGLYG

|<———————>|       |<———————>|              |<———————>|  [D]

|<———————————>|<———————————>||<————————————————————————>|  [K]

Viridin
AGEECDCGSPANPCCDAATCKLRPGAQCADGLCCDQCRFIKKGKICRRARGDNPDDRCTGQSADCPRNRFH

|<———————————>|                                                            N-term

|<———————>|   |<———————————>|  [K]

|<———————>|         |<———>|  [D]

Molossin
EAGIECDCGSPENPCCDAATCKLRPGAQCADGLCCDQCRFIKKGKICRRARGDNPDDRCTGQSADCPRNRFHA

|<—————>|                                                                  N-term

|<———————>|   |<———————————>|  [K]

|<———————>|         |<———>|  [D]

Basilicin
AGEECDCGSPANPCCDAATCKLRPGAQCAEGLCCDQCRFIKKGKICRRARGDNPDDRCTGQSADCPRNHFHA

|<—————————>|                                                              N-term

|<———————>|   |<———————————>|  [K]

|<——————————>|<———>|              |<———>|  [D]
```

FIG. 6C

```
                10        20        30        40        50        60        70
                ..        ..        ..        ..        ..        ..        ..
       EAGEECDCGSPENPCCDAATCKLRPGAQCADGLCCDQCRFMKKGTVCRVAKGDWNDDTCTGQSADCPRNGLYG    BARBOURIN
                A                                            R                      TERGEMININ
        -  T                                                                        CERASTIN
                A                                            R                      LUTOSIN
                A                                                                   CROTATROXIN
        -  L                                                                        RUBERIN
        -  L     A                           -        KI  RR    NP   R     RFHA     MOLOSSIN
                A                            -        KI  RR    NPN  R     RFH-     HORRIDIN
                A                            -        KI  RR    NP   R     RFH-     VIRIDIN
        -  -    A                            -        KI  RR    NP   R     HFHA     BASILICIN
                AA                                    KGA KI RR NP   R     Y        LACHESIN
                A              E                      K RI RR   NP   R     RF(H)-   COTIARIN
                A              GE          S  -       I   RR    DL   YNI G -        ELEGANTIN
        D  A              GE          XX RI            I R      FP R  LNG  P HA     ALBOLABRIN
                S                      S IEE               IR   DL   YNR G XNDL-    FLAVOVIRIDIN
        D  A              E           K E             -RR       DVN  NI G  PFH-     TRIGRAMIN
        -  -                                                                 PFH-   APPLAGGIN
```

FIG. 12A

```
          10        20        30        40        50
           :         :         :         :         :
ZROEEPCATGPCCRRCKFKRAGKVCRVARGDWNNDYCTGKSCDCPRNPWNG    ERISTICOPHIN 30        40        50        60        70
           :         :         :         :         :
ECESGPCCRNCKFLKEGTICKRARGDDMDDYCNGKT

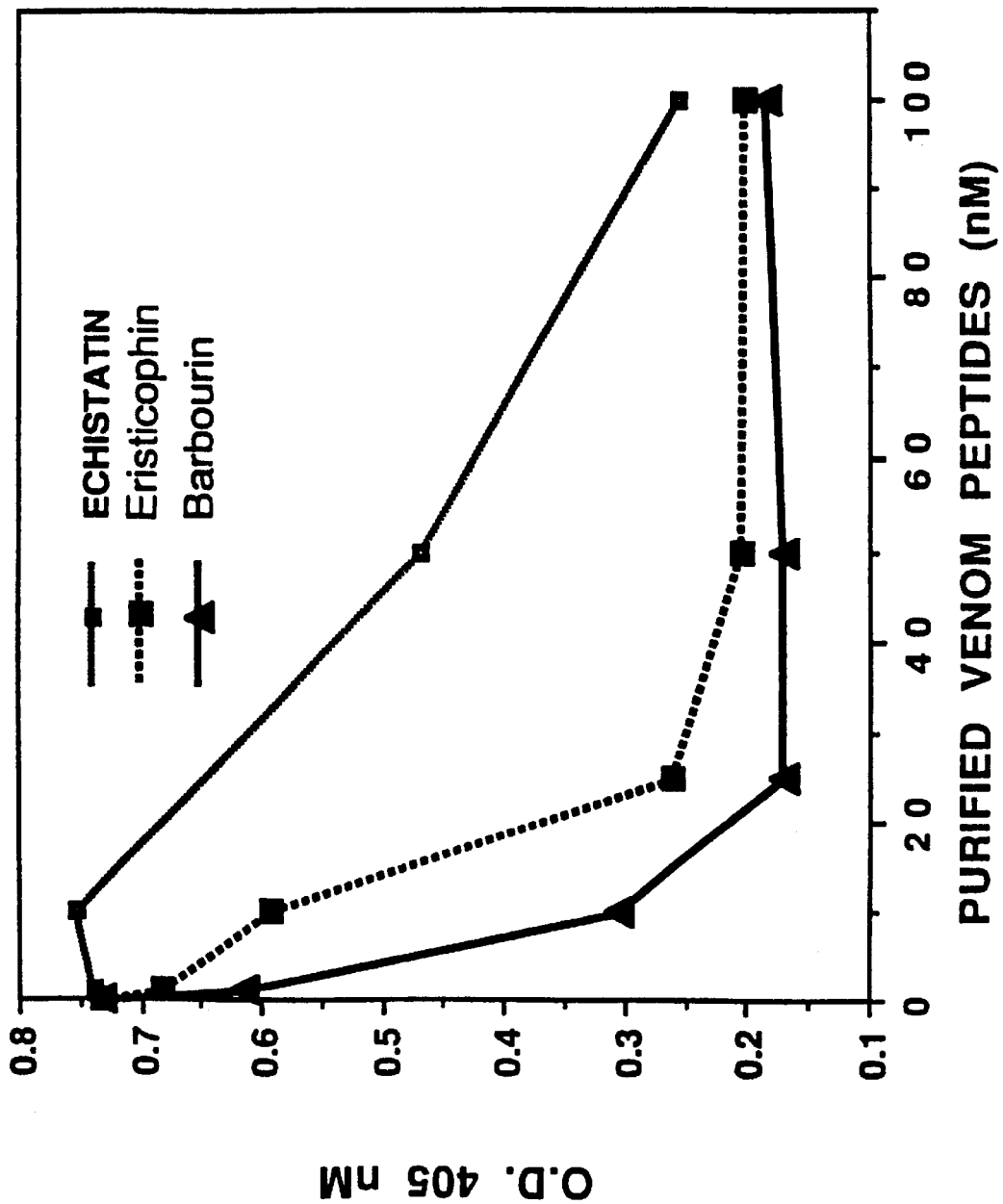

| | Fibrinogen/<br>GP IIb–IIIa | Vitronectin/<br>VnR |
|---|---|---|
| Barbourin | 10nm* | >100nm |
| Tergeminin | 16 | 16 |
| Truncated Sist. m. barbouri. (Analog #1) | 10 | >120 |
| Crotalus v. helleri | 20 | 25 |
| Cerastin | 2 | 2 |
| Ruberin | 10 | 10 |
| Crotalus atrox | 5 | 5 |
| Crotalus d. totonacus | 1-2 | |
| Crotalus v. lutosus | 5 | 5 |
| Bothrups jararacussu | 25 | 5 |
| Cotiarin | >10 | 1 |
| Eristicophin | 25 | 25 |
| Synthetic "Eristicophin" w/ KGDW(Analog#2) | 40 | >150 |
| Cyclic GCGKGDWPCA-NH2 (Analog #3) | 900 | >20,000 |

FIG. 26

Barbourin(1–73)

```
        M   E   A   G   E   E   C   D   C   G   S   P   E
AAT.TCC.ATG.GAA.GCT.GGT.GAA.GAA.TGC.GAC.TGC.GGT.TGT.CCG.GAA
^Eco R1  ^Nco 1

N   P   C   C   D   A   A   T   C   K   L   R   P   G   A
AAC.CCG.TGT.TGC.GAC.GCA.GCG.ACT.TGC.AAA.CTG.CGT.CCG.GGC.GCT

Q   C   A   D   G   L   C   C   D   Q   C   R   F   L   K
CAG.TGC.GCA.GAC.GGT.CTG.TGC.TGT.GAT.CAG.TGC.CGT.TTC.CTG.AAA

K   G   T   V   C   R   V   A   K   G   D   W   N   D   D
AAG.GGT.ACT.GTT.TGC.CGT.GTA.GCT.AAA.GGC.GAC.TGG.AAC.GAC.GAT

T   C   T   G   Q   S   A   D   C   P   R   N   G   L   Y
ACT.TGC.ACT.GGT.CAG.TCT.TGT.GAC.TGC.CCG.CGT.AAC.GGC.CTG.TAC

G
GGT.TGA.A....HindIII
```

FIG. 38

PhoA/M-1,L41 Barbourin(1-73)

Pho A:
```
          M   K   Q   S   T   I   A   L   A
R1......AA.TTC.ATG.AAA.CAA.AGC.ACT.ATT.GCA.CTG.GCA

L   L   P   L   L   F   T   P   V   T   K   A
CTC.TTA.CCG.TTA.CTG.TTC.ACC.CCT.GTG.ACC.AAA.GCC/  (splice site)
```

Barbourin:
```
 M   E   A   G   E   E   C   D   C   G   S   P   E   N   P
ATG.GAA.GCT.GGT.GAA.GAA.TGC.GAC.TGC.GGT.TGT.CCG.GAA.AAC.CCG C   C   D   A   A   T   C   K   L   R   P   G   A   Q   C
TGT.TGC.GAC.GCA.GCG.ACT.TGC.AAA.CTG.CGT.CCG.GGC.GCT.CAG.TGC A   D   G   L   C   C   D   Q   C   R   F   L   K   K   G
GCA.GAC.GGT.CTG.TGC.TGT.GAT.CAG.TGC.CGT.TTC.CTG.AAA.AAG.GGT T   V   C   R   V   A   K   G   D   W   N   D   D   T   C
ACT.GTT.TGC.CGT.GTA.GCT.AAA.GGC.GAC.TGG.AAC.GAC.GAT.ACT.TGC T   G   Q   S   A   D   C   P   R   N   G   L   Y   G
ACT.GGT.CAG.TCT.GCT.GAC.TGC.CCG.CGT.AAC.GGC.CTG.TAC.GGT
```

TGA.A....HindIII

FIG. 39

PhoA/E$^{28}$, L$^{41}$, C$^{64}$ Barbourin$_{(28-73)}$

5' oligonucleotide:

```
     EcoRI        BglII              NcoI        MstI
5' AAA GAA TTC CTA GAT CTC GAC GAA GCC ATG GAA TGC GCA GAC GGT CTG TGC 3'
         D   L   D   E   A   M   E   C   A   D   G   L   C
```

FIG. 41A

3' oligonucleotide:

```
                        BamHI    HindIII
5' CGT ACC GGC CTG TAC GGT ATG GAT CCA TAA CGT TCC C 3'
   R   N   G   L   Y   G   M   D   P   Oc
3' GCA TGG CCG GAC ATG CCA TAC CTA GGT ATT GCA AGG G 5'
```

FIG. 41B

\* Actual oligonucleotide used in the polymerase chain reaction.

PLATELET AGGREGATION INHIBITORS

CROSS-REFERENCE TO RELATED APPLICATIONS

This application is a continuation of U.S. application Ser. No. 08/067,139, filed May 24, 1993, now abandoned which is a Continuation of U.S. application Ser. No. 07/483,229, filed Feb. 20, 1990, now U.S. Pat. No. 5,318,899, which is a continuation-in-part of U.S. patent application Ser. No. 07/418,028 filed Oct. 6, 1989, now abandoned, which is a continuation-in-part of U.S. patent application 07/367,509, filed Jun. 16, 1989, now abandoned.

TECHNICAL FIELD

This invention relates to a group of peptides which are, or are related to, platelet aggregation inhibitors isolated and purified from various snake venoms. These peptides are useful as therapeutic agents for the treatment of, and prevention of, platelet-associated ischemic disorders. More specifically, the invention concerns peptides which block specific receptors for adhesive proteins involved in platelet adherence and aggregation. Furthermore, this invention describes methods for detecting and purifying said polypeptides to substantial homogeneity from snake venoms, as well as processes for using the primary amino acid sequences of these polypeptides to prepare active peptides both synthetically and through use of recombinant DNA methods.

BACKGROUND ART

Heart disease is the primary cause of death in most western societies. Death from heart disease is often induced by platelet-dependent ischemic syndromes which are initiated by atherosclerosis and arteriosclerosis and include, but are not limited to, acute myocardial infarction, chronic unstable angina, transient ischemic attacks and strokes, peripheral vascular disease, arterial thrombosis, preeclampsia, embolism, restenosis and/or thrombosis following angioplasty, carotid endarterectomy, anastomosis of vascular grafts, and chronic cardiovascular devices (e.g., in-dwelling catheters or shunts "extracorporeal circulating devices"). These syndromes represent a variety of stenotic and occlusive vascular disorders thought to be initiated by platelet activation either on vessel walls or within the lumen by blood-borne mediators but are manifested by platelet aggregates which form thrombi that restrict blood flow.

Numerous studies have contributed to an understanding of the mechanism of platelet aggregation and thrombus formation. Platelets respond to a variety of blood vessel injuries, such as narrowing of the lumen, plaque formation, and the presence of foreign bodies (e.g., catheters) and the like. The response of platelets to these injuries is a sequence of events including platelet adherence and activation, and the release of platelet granular components, including potent cellular mitogenic factors. The activated platelet aggregates induce the formation of fibrin, which further stabilizes the thrombus.

Much is now known about mechanisms regulating these responses. Although unstimulated platelets contain receptors for several adhesive proteins including laminin (VLA 2, VLA 6) and collagen (VLA 2, GPIV, others), the initial attachment of platelets to subendothelium is believed to be mediated by the binding of platelet membrane glycoprotein (GP) Ib to the immobilized von Willebrand factor. Subsequent platelet activation can be initiated by one or more of the known physiological agonists including: ADP, epinephrine, thrombin, collagen, and thromboxane A2.

Platelet aggregation is mediated by GP IIb–IIIa complex on the platelet membrane surface. GP IIb–IIIa exists on the surface of unstimulated platelets in an inactive form. When platelets are activated by adhesion and the physiological agonists, the GP IIb–IIIa also becomes activated such that it becomes a receptor for fibrinogen (Fg), von Willebrand Factor (vWF), and fibronectin (Fn) (see Phillips et al., *Blood* (1988) 71:831–843); however, it is the binding of fibrinogen and/or von Willebrand factor that is believed to be principally responsible for platelet aggregation and thrombus formation in vivo. Therefore, substances which specifically inhibit the binding of fibrinogen or von Willebrand factor to GP IIb–IIIa inhibit platelet aggregation and could be candidates for inhibiting thrombus formation in vivo.

Platelet GP IIb–IIIa is now known to be a member of a superfamily of structurally related adhesive protein receptors known collectively as the "integrins." Like GP IIb–IIIa, all integrins known to date are two subunit molecules with a larger alpha-subunit (e.g., GP IIb) and a smaller beta-subunit (e.g., GP IIIa). There is a high degree of homology between the known sequences of the integrin subunits indicating that the integrins evolved from a common precursor. Integrins function in a variety of cellular adhesions and have been found in leucocytes, endothelial cells, smooth muscle cells and other cells in the vasculature. Because integrins are widely distributed, while GP IIb–IIIa is restricted to platelets, a preferred antiaggregating agent would selectively inhibit GP IIb–IIIa as opposed to other integrins.

Several classes of peptides have been disclosed which block the binding of adhesive proteins to activated platelets and inhibit platelet aggregation (see Hawiger et al., U.S. Pat. No. 4,661,471; and Rouslahti et al., U.S. Pat. Nos. 4,614, 517; 4,578,079; 4,792,525; and UK application GB 2,207, 922A). In one class of peptides, the sequence RGD is critical, and the tetrapeptide sequences RGDS, RGDT, RGDC, have been used specifically. The amino acid sequence RGDX is found in a variety of adhesive proteins including Fg, Vn, vWF and Fn. This sequence has been demonstrated to play an important role in the interaction of adhesive proteins with adhesive protein receptors because peptides containing this sequence block the binding of adhesive proteins. See, e.g., Pierschbacher, M. D., et al., *J Biol Chem* (1987) 262:17294–17298; Ruggeri et al., *Proc Natl Acad Sci* (USA) (1986) 83:5708–5712; and Rouslahti et al., *Cell* (1986) 44:517–518.

The structural variations permitted in RGD-containing peptides have been explored by Pierschbacher, M. D. et al. *J Biol Chem* (supra). In these studies, it was found that manipulating the RGD-containing sequence not only effected the activity related to inhibition of binding of fibronectin or vitronectrin to substrate, but could also effect differentiation between binding of the two ligands. The peptide sequence GRGDSPC which was taken from the cell attachment domain of fibronectin was used as a model peptide. Certain substitutions, such as replacement of L-Arg with D-Arg seem to have no effect on the binding of either ligand, but substituting D-Ala for Gly or D-Asp for L-Asp destroyed the inhibition activity. While substituting D-Ser for L-Ser reduced inhibition of vitronectin interaction with vitronectin receptor, there was little effect on fibronectin interaction with fibronectin receptor; substitution of Asn for Ser resulted in a peptide that had enhanced inhibition of fibronectin binding, and a decreased effect on vitronectin binding. Alternate substitutions for Ser had other effects. Threonine substituted for Ser gave a peptide with increased inhibition of binding to the vitronectin receptor; substitution of L-Pro led to an inactive peptide. A cyclic peptide was also prepared of the sequence Gly-Pen-Gly-Arg-Gly-Asp-Ser-Pro-Cys-Ala, wherein "Pen" is penicillamine and a disulfide bridge was formed between the Pen and Cys. In the view of the authors, penicillamine had the function of increasing conformational restraints on the ring whereas the N-terminal Gly and carboxy-terminal Ala were added to distance the free amino and carboxyl groups from the ring. This cyclic peptide was able to inhibit vitronectin binding more strongly than the same peptide before cyclization, but was ineffective in inhibiting fibronectin binding.

Recently, an antithrombotic peptide with a modification of the RGD sequence having the "R" residue alkylated was reported by Samanen, J., et al., *J Cell Biochem* (1990) *Suppl* 14A:A229.

A separate class of inhibitory peptides utilizes peptide sequences modeled on the carboxyl terminal sequence derived from the gamma chain of fibrinogen, the dodecapeptide HHLGGAQKAGDV (Kloczewiak et al., *Biochemistry* (1989) 28:2915–2919; Timmons et al., (Ibid), 2919–2923 U.S. Pat. No. 4,661,471 (supra); EP application 298,820,). Although this sequence inhibits Fg and vWF binding to GP IIb–IIIa and subsequent platelet aggregation, the usefulness of this peptide is limited because it has a low affinity of interaction with platelet receptors ($IC_{50}$=10–100 $\mu M$).

Recently, several groups have isolated and characterized a new class of low molecular weight polypeptide factors from snake venoms which have extremely high affinity for the GP IIb–IIIa complex. Huang, T.-F., et al., *J Biol Chem* (1987) 262:16157–16163; Huang, T.-F., et al., *Biochemistry* (1989) 28:661–666 report the primary structure of trigramin, a 72 amino acid peptide containing RGD and 6 disulfide bridges isolated from *Trimeresurus gramineus*. Gan, Z.-R., et al., *J Biol Chem* (1988) 263:19827–19832, report the properties and structure of echistatin, a 49 amino acid peptide also containing RGD and 4 putative disulfide bridges which is isolated from *Echis carinatus*. Williams, J. A., et al., *FASEB Journal* (1989) 3:A310, Abstr. No. 487m, report the sequence and properties of the related peptides elegantin, albolabrin, and flavoviridin.

Included in this group of inhibitory peptides from snake venoms are alboabrin isolated from *Trimeresurus albolabris*, elegantin isolated from *T. elegans*, flavoviridin isolated from *T. flavoviridis*, batroxostatin isolated from *Bothrops atrox*, bitistatin isolated from *Bitis arietans* reported by Niewiarowski, S., et al., *Thromb Haemostas* (1989) 62:319 (Abstr. SY-XIV-5). In addition, applaggin has been purified from *Agkistrodon p. piscivorus* and reported by Chao, B., et al., *Thromb Haemostas* (1989) 62:50 (Abstr. 120) and halysin, purified from *Aqkistrodon halys* which was reported by Huang, T. F., et al., *Thromb haemostas* (1989) 62:48 (Abstr. 112). All of these peptides show a high degree of sequence homology. In addition, all of the peptides reported to date from snake venoms which inhibit the binding of adhesive proteins to integrin receptors contain the RGD sequence.

Although these reported snake venom factors are potent platelet aggregation inhibitors in vitro, these peptides also bind with high affinity to other members of the adhesive protein receptors such as the vitronectin and fibronectin receptors (Knudsen, K. A., et al., *Exp Cell Res* (1988) 179:42–49; Rucinski, B., et. al., *Thromb Haemostas* (1989) 62:50 (Abstr. 120). This lack of specificity of snake venom factors for GP IIb–IIIa is an undesirable feature of their therapeutic use as inhibitors of thrombus formation, because they have the potential of affecting the adhesive properties of other cells in the vasculature, particularly those adhesions mediated by integrins.

Another approach developed for the generation of platelet thrombus inhibitors has been the use of murine anti-GP IIb–IIIa monoclonal antibodies which block the binding of the adhesive proteins to stimulated platelets. These monoclonal antibodies have been used to prevent coronary artery reocclusion after reperfusion with tissue plasminogen activator in dogs (Yasuda, T., et al., *J Clin Invest* (1988) 81:1284–1291) and to prevent cyclic reduction of flow in injured canine coronary arteries with a high grade stenosis. Potential side effects of the use of such monoclonal antibodies in humans may result from their long-lasting effects and from their potential immunogenicity.

Clearly, additional therapeutic treatment regimens are needed for preventing or at least mitigating undesirable thrombus formation. In particular, therapeutic agents capable of blocking or inhibiting thrombus formation at specific locations without compromising hemostasis and without affecting other cellular adhesions, would provide major therapeutic benefits. Ideally, these agents should be potent, specific for GP IIb–IIIa, and nonimmunogenic to most patients; they also should be easy to administer, stable and economical to produce. Further, these agents should act transiently and be capable of functioning at the earliest stages of thrombus formation, without interfering with long-term hemostasis. The present invention fills these and other related needs.

Disclosure of the Invention

The invention provides a simple screening procedure to identify low molecular weight (<10 kd) factors in snake venom or other biological sources that specifically inhibit thrombus formation mediated by platelet aggregation. This procedure takes advantage of the understanding that platelet aggregation is primarily effected through binding of fibrinogen and/or vWF to GP IIb–IIIa at the surface of platelets when the platelets are treated with appropriate stimuli, such as ADP. By using these criteria, i.e., inhibition of binding of fibrinogen and/or vWF to isolated receptor and analogous criteria related to inhibition of binding of fibronectin (Fn) to fibronectin receptor (Fn/FnR binding) and vitronectin to vitronectin receptor (Vn/VnR binding), as well as the binding of other factors, such as Fn and Vn to GP IIb–IIIa, a specificity profile for the platelet aggregation inhibitor (PAI) can be rapidly and conveniently obtained. This approach has been used to screen and characterize an extensive panel of snake venoms for the presence or absence of PAI, to characterize the specificity of PAI identified from this panel for their specificity at inhibiting binding to GP IIb–IIIa as opposed to inhibiting other integrins, and to identify active peptides which are derivatives of these PAIs.

Accordingly, in one aspect, the invention is directed to a rapid screening method for the presence or absence of PAI in a biological fluid, which method comprises contacting the fluid with isolated GP IIb–IIIa in a test reaction in the presence of fibrinogen and comparing the amount of fibrinogen bound to GP IIb–IIIa in this test reaction with the amount of fibrinogen bound to GP IIb–IIIa in a control reaction. The method may further include test and control reactions which involve contacting Fn with Fn receptor, Vn with Vn receptor, Fn with GP IIb–IIIa, or vWF with GP IIb–IIIa to characterize the specificity of the PAI.

In another aspect, the invention is directed to novel PAI in isolated form which is identified in, and can be isolated from, active snake venom according to the methods of the invention. In particular, the invention relates to PAI, in isolated form, which can be isolated from *Echis colorata*,

*Eristicophis macmahonii; A. hypnale, A. acutus, A. piscivorous leucostoma, A. piscivorus conanti; Bothrops asper; Bothrops cotiara, B. jararaca, B. jararacussu, B. lansbergi, B. medusa, B. nasuta, B. neuwiedi, B. pradoi, B. schlegli; Crotalus atrox, C. basilicus, C. cerastes cerastes, C. durissus durissus, C. durissus totonatacus, C. horridus horridus, C. molossus molossus, C. ruber ruber, C. viridis cereberus, Crotalus v. helleri, Crotalus v. lutosus, Crotalus v. oreganus, Crotalus v. viridis; Lachesis mutas; Sistrurus catenatus tergeminus*, and *Sistrurus milarus barbouri.*

Preferred are PAIs in isolated form prepared from, or having the amino acid sequences of, those obtained from *Eristicophis macmahonii* (eristicophin); *Bothrops cotiara* (cotiarin); *B. jararacussu; Crotalus atrox* (crotatroxin); *Crotalus basilicus* (basilicin); *C. cerastes cerastes* (cerastin); *C. durissus totanatacus; C. durissus durissus; C. h. horridus* (horridin); *Crotalus m. molossus* (molossin); *C. ruber ruber* (ruberin); *Crotalus viridis lutosus* (lutosin); *C. v. viridis* (viridin); *Crotalus v. oreganus; Crotalus v. helleri; Lachesis mutas* (lachesin); *Sistrurus catenatus tergeminus* (tergeminin); and *S. milarus barbouri* (barbourin).

Especially preferred are eristicophin, cotiarin, crotatroxin, cerastin, horridin, ruberin, lachesin, basilicin, lutosin, molossin, viridin, tergeminin and barbourin.

The invention also includes peptides of the amino acid sequences as described above which are truncated and/or modified forms of the naturally occurring peptides and/or have one or more peptide linkages replaced by alternate linkages such as $—CH_2NH—$ or $—CH_2CH_2—$.

In a preferred aspect, the invention relates to PAI in isolated form which can be prepared from active snake venom identified by the method of the invention, and shown to specifically inhibit the binding fibrinogen (Fg) and/or von Willebrand Factor (vWF) to GP IIb–IIIa, and their truncated and/or modified forms.

In still another preferred aspect, the invention relates to PAI of snake venom in isolated form wherein the sequence responsible for binding to the adhesive protein receptor includes the sequence KGD.

In another major aspect, the invention is directed to a group of peptides or peptide-related compounds in general which are platelet aggregation inhibitors that are capable of inhibiting binding of Fg or vWF to GP IIb–IIIa at a substantially higher potency than that at which they inhibit binding of vitronectin to vitronectin receptor or fibronectin to fibronectin receptor. These peptides are characterized by having the binding sequence K*GDX in place of the RGDX binding sequence which is found in the prior art PAI proteins. K* is a substituted or unsubstituted lysyl residue of the formula $R^1{}_2N(CH_2)_4CHNHCO—$ wherein each $R^1$ is independently H or a substituent which is sufficiently electron donating so as not to destroy the bacicity of the adjacent nitrogen, and wherein one or two of the methylene residues may optionally be substituted by O or S, as described below. The barbourin PAI isolated from *S. milarus barbouri* is one illustration of this series of peptides. However, shorter forms of this peptide can also be used, as well as analogous sequences which also contain 1–10 amino acid residue modifications elsewhere in the peptide chain, and/or replacement of peptide linkages with alternate linkages. Other illustrative embodiments include isolated PAI peptides having a native RGDX sequence wherein this is replaced by K*GDX. As in the case of barbourin, these isolated PAI may be otherwise in native form, or may be truncated and/or may contain 1–10 amino acid residue substitutions or deletions, and/or may have non-peptide linkages substituted for peptide linkages.

Another group of compounds which falls within the scope of the invention is that wherein the foregoing compounds are as described, except that the glycyl residue in the RGD or K*GD sequence is replaced by a sarcosyl residue. This class of compounds retains the potency and specificity of the related RGD or K*GD-containing peptides.

Another illustrative group of embodiments are peptides or modified peptides having specific PAI activity of the formula wherein K* is a substituted or unsubstituted lysyl residue of the formula $R^1{}_2N(CH_2)_4$ CHNHCO— as described above, wherein each $R_1{}^1$ is independently H, alkyl (1–6C), or at most one $R^1$ is $R^2—C{=}NR^3$ wherein $R^2$ is H, alkyl (1–6C) or is $NR^4{}_2$ in which each $R^4$ is independently H or alkyl(1–6C) and $R^3$ is H, alkyl(1–6C), phenyl or benzyl, or $R^2—C{=}NR^3$ is a radical selected from the group consisting of:

, , , and , where m is an integer of 2–3, and each $R^5$ is independently H or alkyl(1–6C);

and wherein one or two ($CH_2$) may be replaced by O or S provided said O or S is not adjacent to another heteroatom;

$AA_1$ is a small, neutral (polar or nonpolar) amino acid and n1 is an integer of 0–3;

$AA_2$ is a neutral, nonpolar large (aromatic or nonaromatic) or a polar aromatic amino acid and $n_2$ is an integer of 0–3;

$AA_3$ is a proline residue or a modified proline residue (as defined below) and $n_3$ is an integer of 0–1;

$AA_4$ is a neutral, small amino acid and $n_4$ is an integer of 0–3;

each of $X_1$ and $X_2$ is independently a residue capable of forming a bond between $X_1$ and $X_2$ to obtain a cyclic compound as shown; and each of $Y_1$ and $Y_2$ is independently a noninterfering substituent or may be absent;

wherein one or more peptide linkages may optionally be replaced by a linkage selected from the group consisting of $—CH_2NH—$, $—CH_2S—$, $CH_2CH_2—$, $—CH{=}CH—$ (cis and trans), $—COCH_2—$, $—CH(OH)CH_2—$ and $—CH_2SO—$.

Other aspects of the invention are concerned with recombinant methods and materials related to the synthesis of these and other related peptides, to methods of in vitro synthesis thereof, to pharmaceutical compositions containing these compounds, and to methods to inhibit platelet aggregation and thrombus formation using these compounds and compositions.

BRIEF DESCRIPTION OF THE DRAWINGS

FIG. 1 shows inhibition of the binding of fibrinogen to GP IIb–IIIa by partially purified snake venoms.

FIGS. 2A, 2B, and 2C show the dose-response adhesion inhibition of Centricon-10 ultrafiltrates of crude venoms in both fibrinogen/GP IIb–IIIa and vitronectin/vitronectin receptor assays. Selectivity of snake venom peptides in GPIIb–IIIa and vitronectin receptor binding assays is shown. Sistrurus m. barbouri venom is used in FIG. 2A. Crotalus ruber venom is used in FIG. 2B. Crotalus basilicus venom is used in FIG. 2C.

FIGS. 6A, 6B and 6C show the complete amino acid sequences of eristicophin, barbourin, tergeminin, lachesin, ruberin, cerastin, cotiarin, crotatroxin, and horridin and enzyme digestion fragments determined by automated Edman degradation.

FIGS. 12A and 12B compare the amino acid sequences of a number of snake venom PAIs to that of barbourin.

Figure 13:
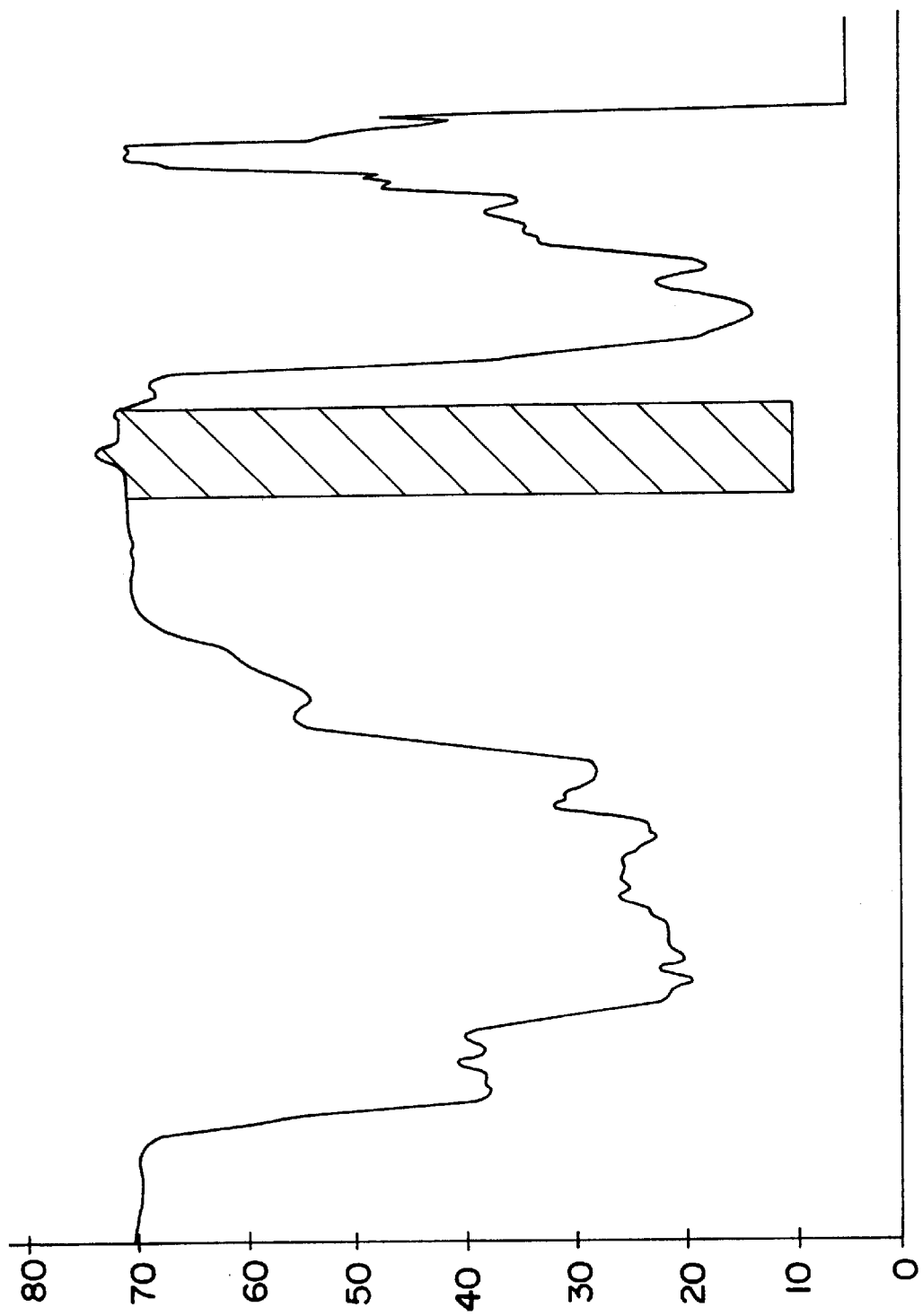

FIG. 13 depicts the HPLC profile of crude PAI from Lachesis mutas venom. Cross-hatched areas contain the biologically active fractions.

Figure 14:
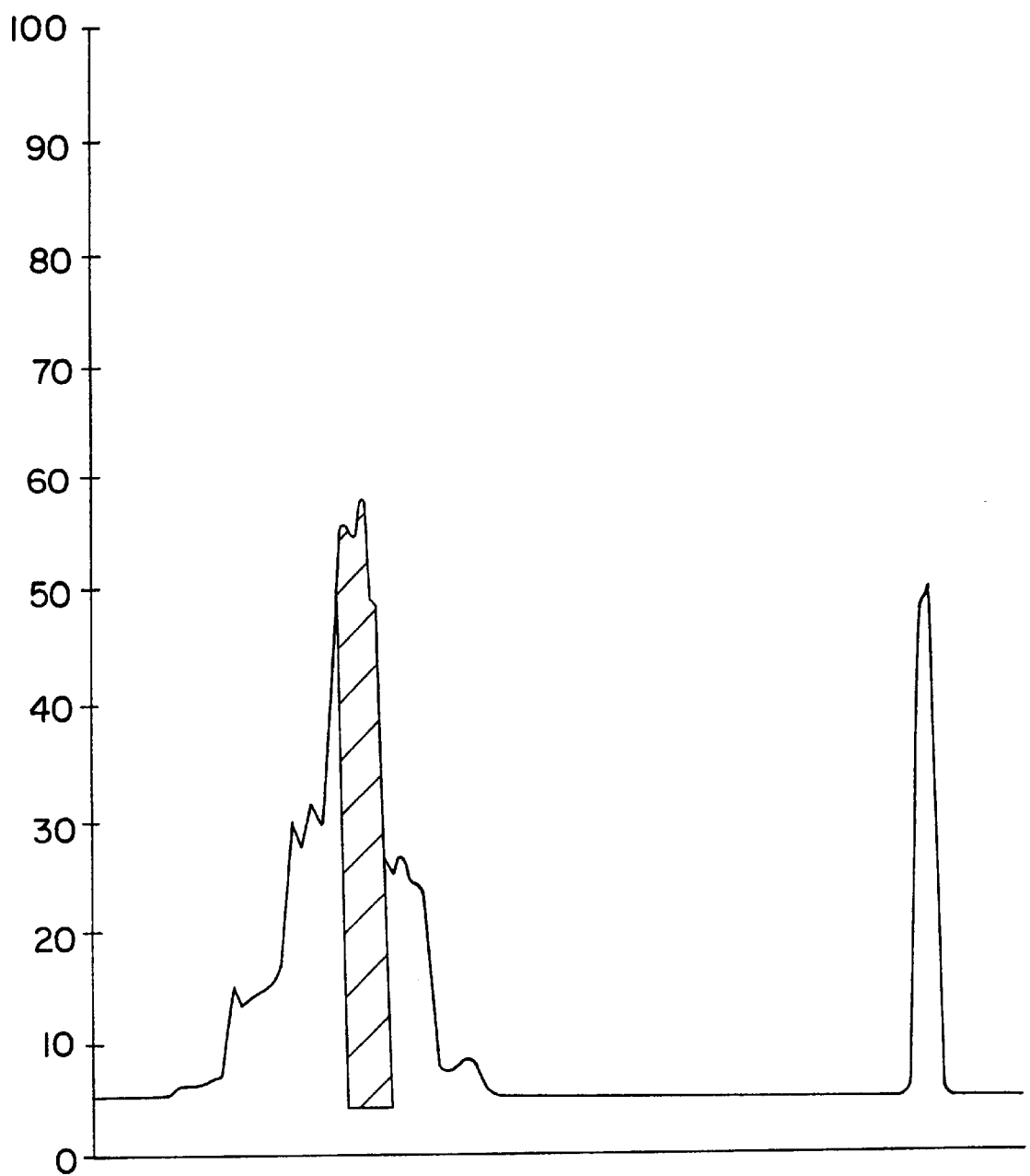

FIG. 14 depicts the slow gradient HPLC profile of the PAI active fractions from FIG. 13. Cross-hatched area contains the biologically active fractions.

Figure 15:
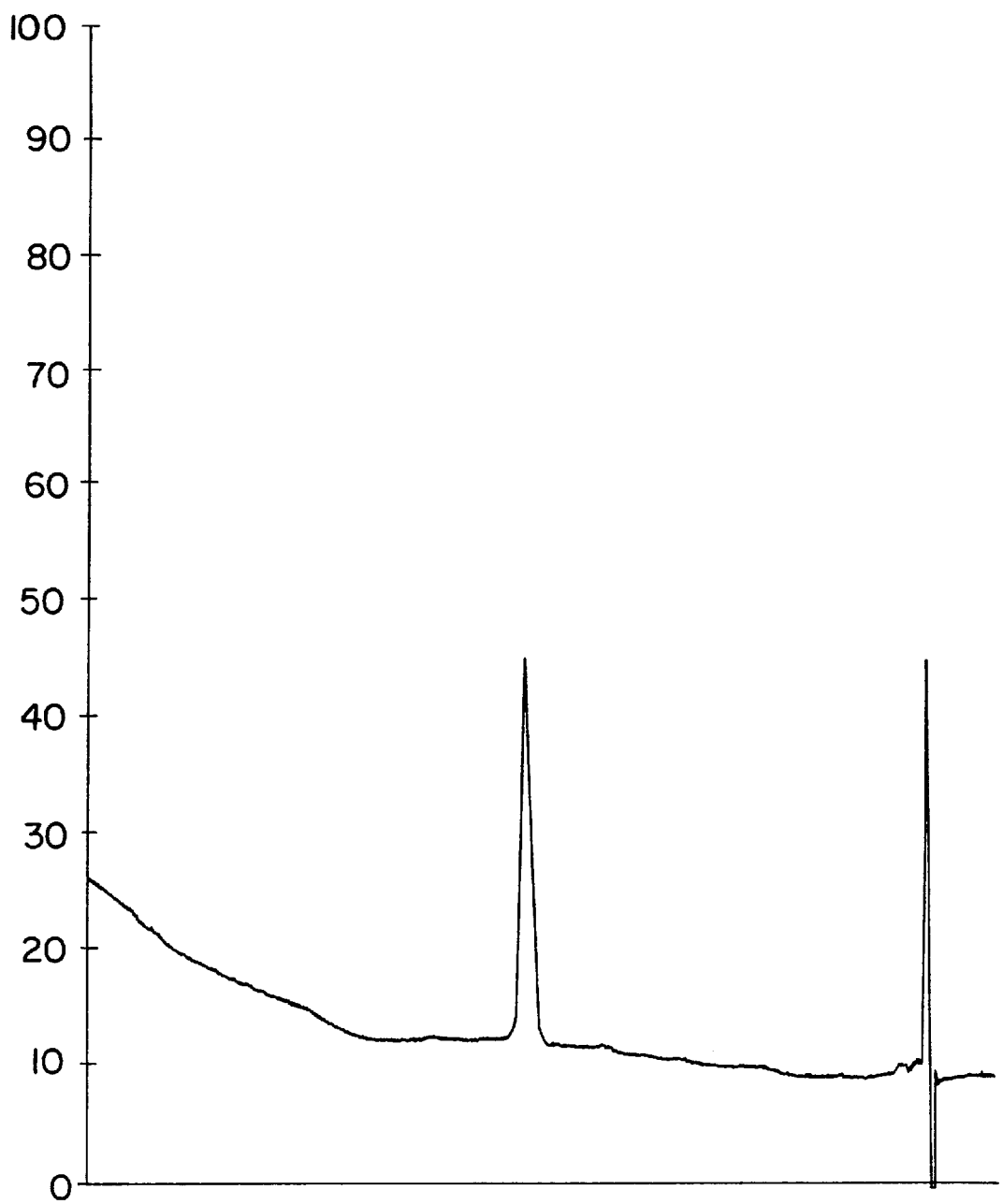

FIG. 15 depicts the analytical HPLC profile of PAI fractions of FIG. 14 from Lachesis mutas to show purified PAI from Lachesis mutas venom.

Figure 16:
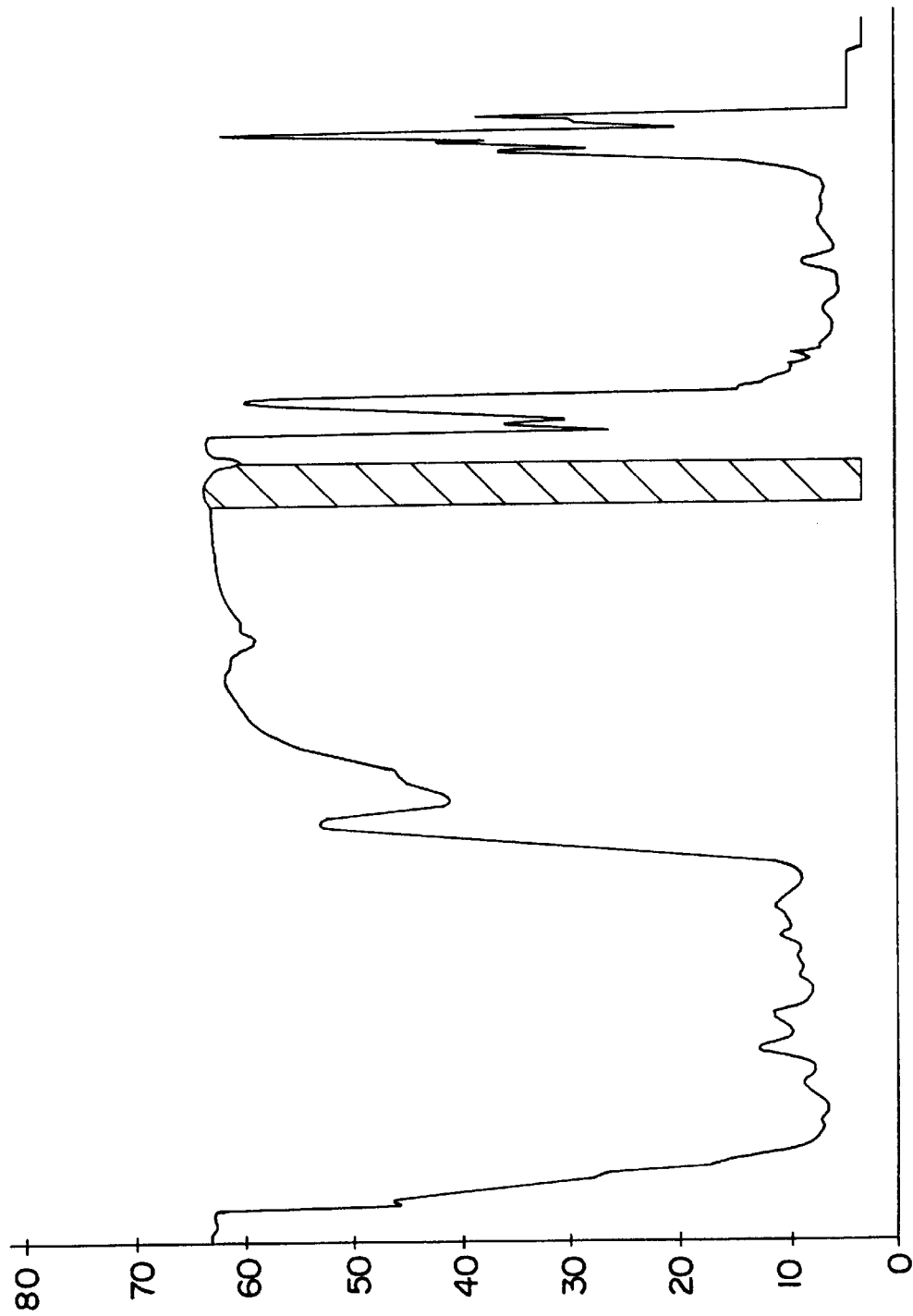

FIG. 16 depicts the HPLC profile of crude PAI from Crotalus viridis viridis venom. Cross-hatched area contains the biologically active fractions.

Figure 17:
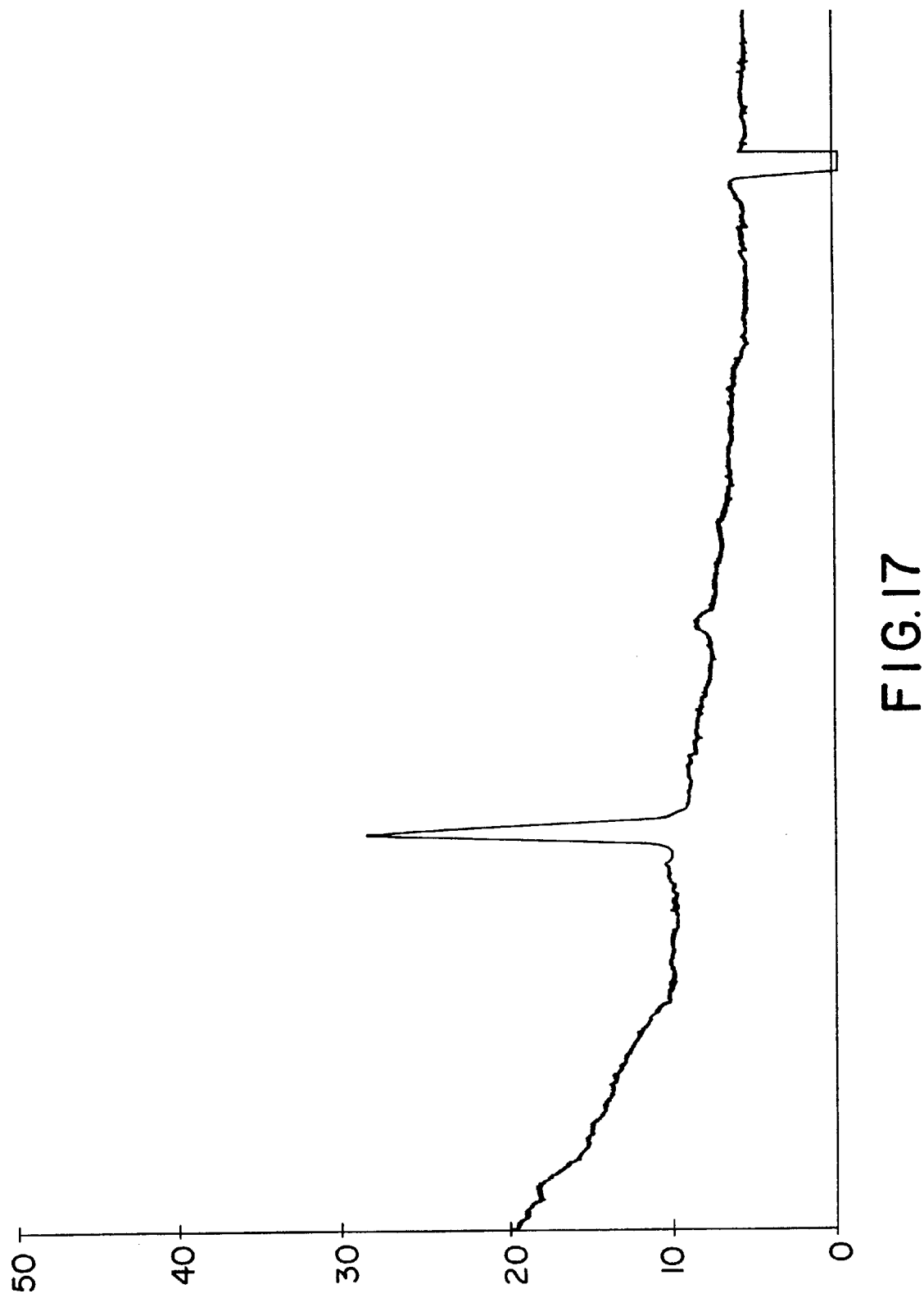

FIG. 17 depicts the HPLC profile of the PAI fractions of FIG. 16 to show purified PAI from Crotalus viridis viridis venom.

FIG. 18 shows the dose-response effects of purified snake venom peptides to inhibit fibrinogen/GP IIb–IIIa binding as compared to echistatin.

Figure 19A:
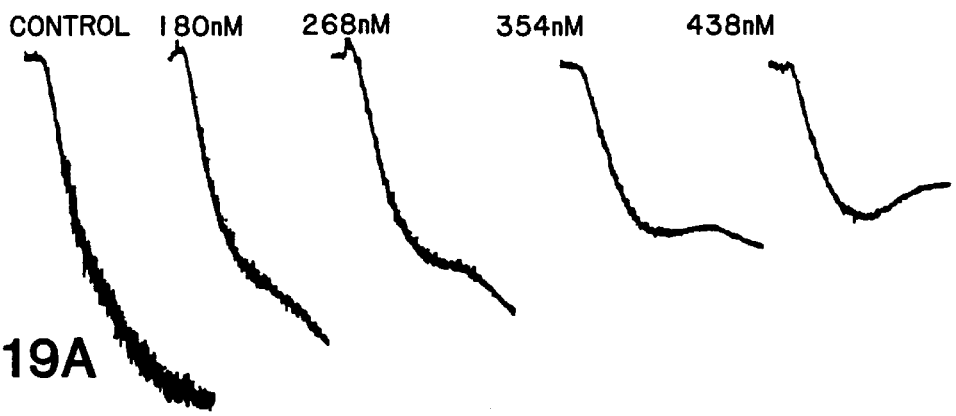
Figure 19B:
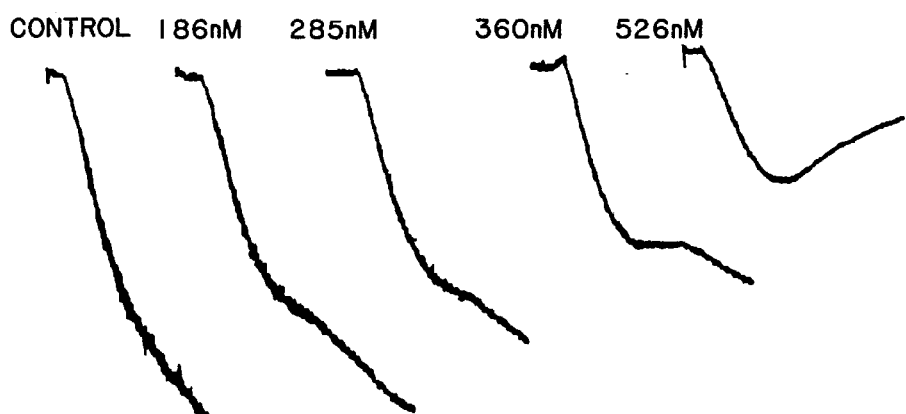
Figure 19C:
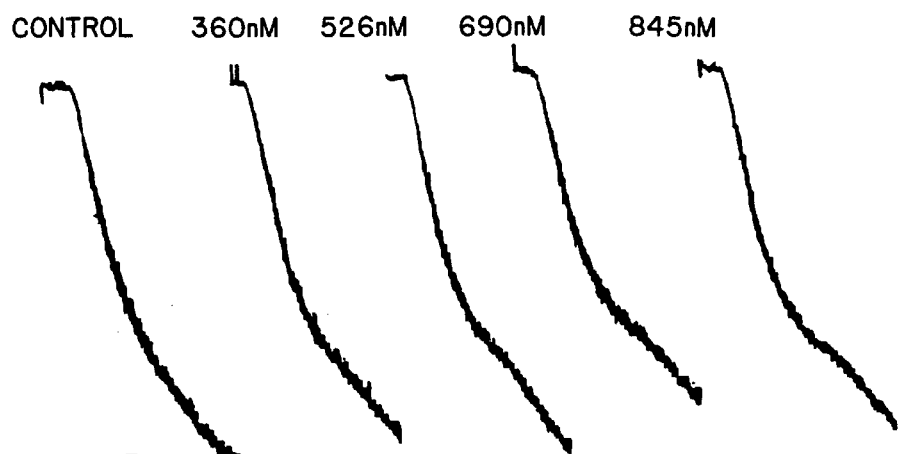

FIGS. 19A, 19B and 19C show the dose-response effects of purified snake venom peptides to inhibit ADP (4 µM) induced human platelet aggregation in platelet rich plasma (PRP), as compared to echistatin. FIG. 19A shows the effect of Sistrurus m. barbouri PAI barbourin. FIG. 19B shows the effect of Eristicophus macmahoni PAI eristicophin. FIG. 19C shows the effect of Echis carnitus PAI echistatin.

Figure 20:
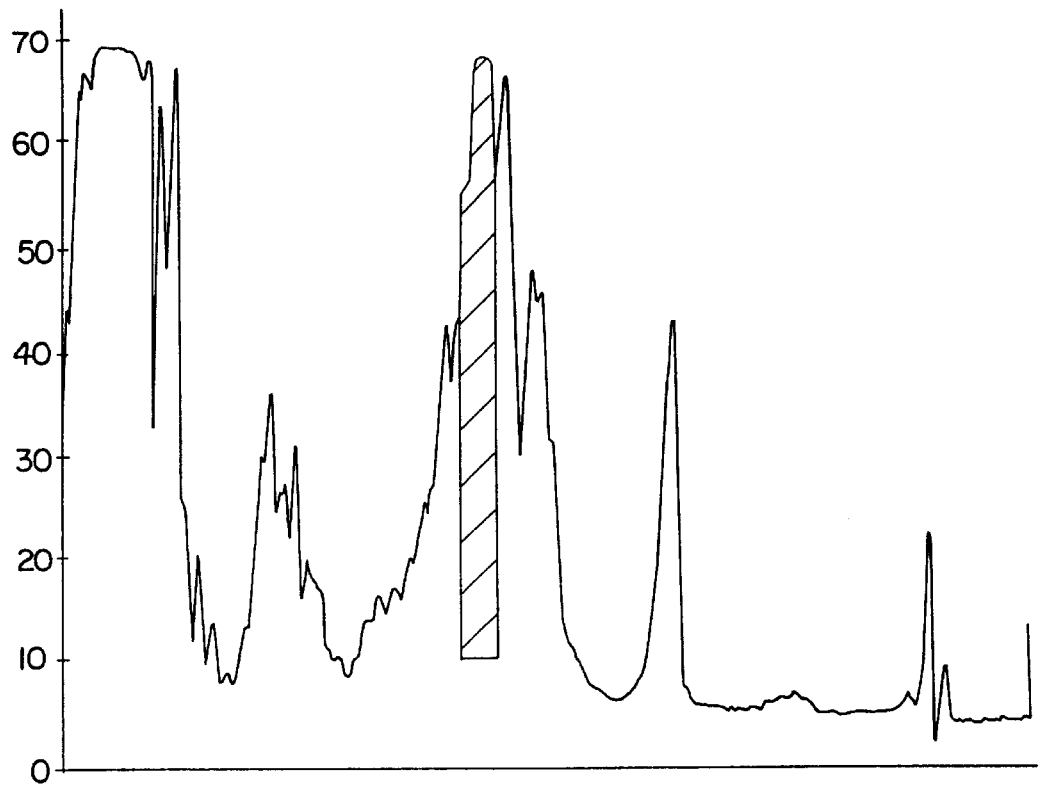

FIG. 20 shows the activity profile from HPLC fractionation of C. c. cerastes venom. Cross-hatched area contains the biologically active fractions.

Figure 21:
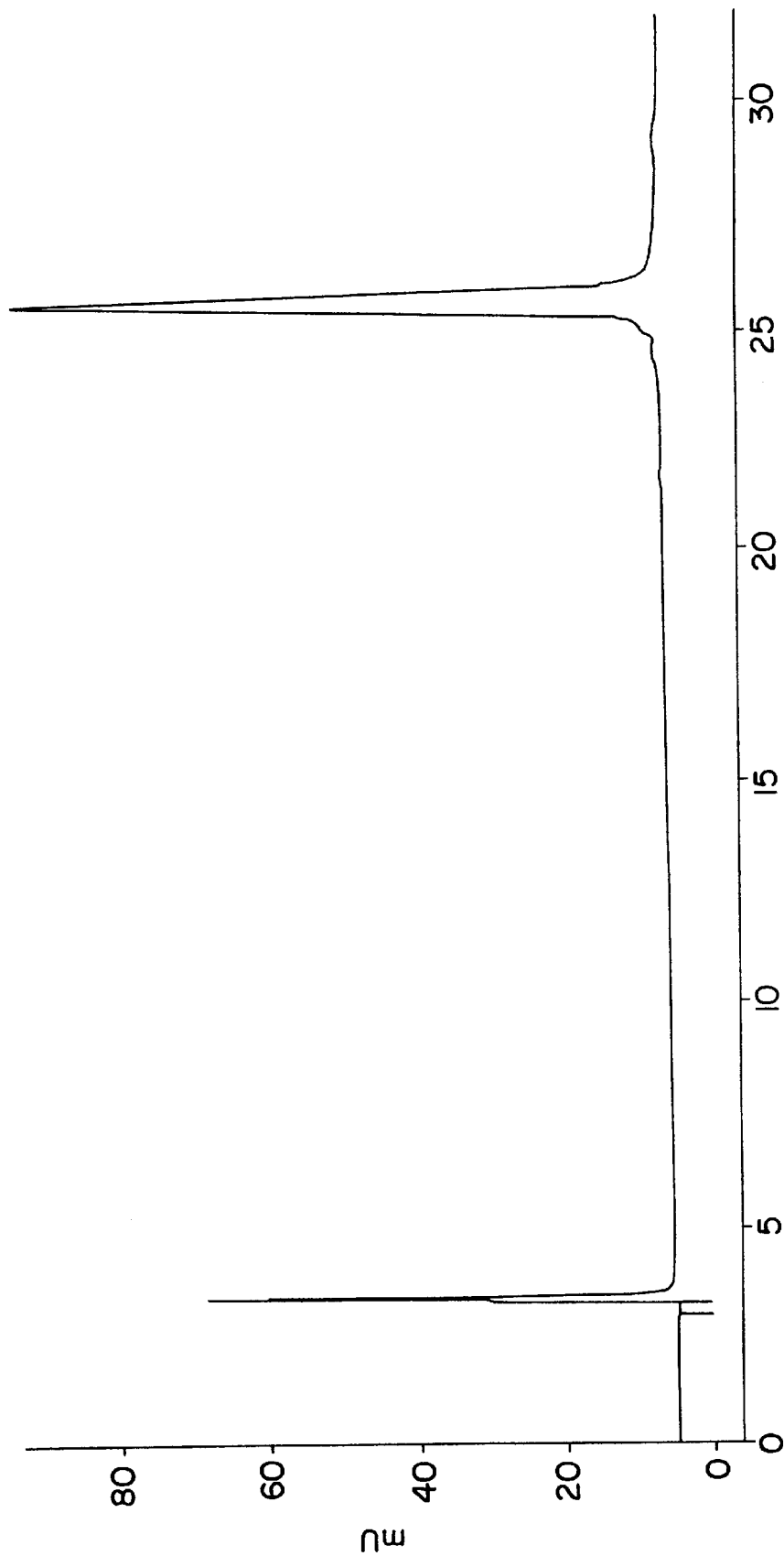

FIG. 21 shows the results of HPLC analysis of the active fractions of FIG. 20 to show purified PAI from Crotalus cerastes cerastes venom.

Figure 22:
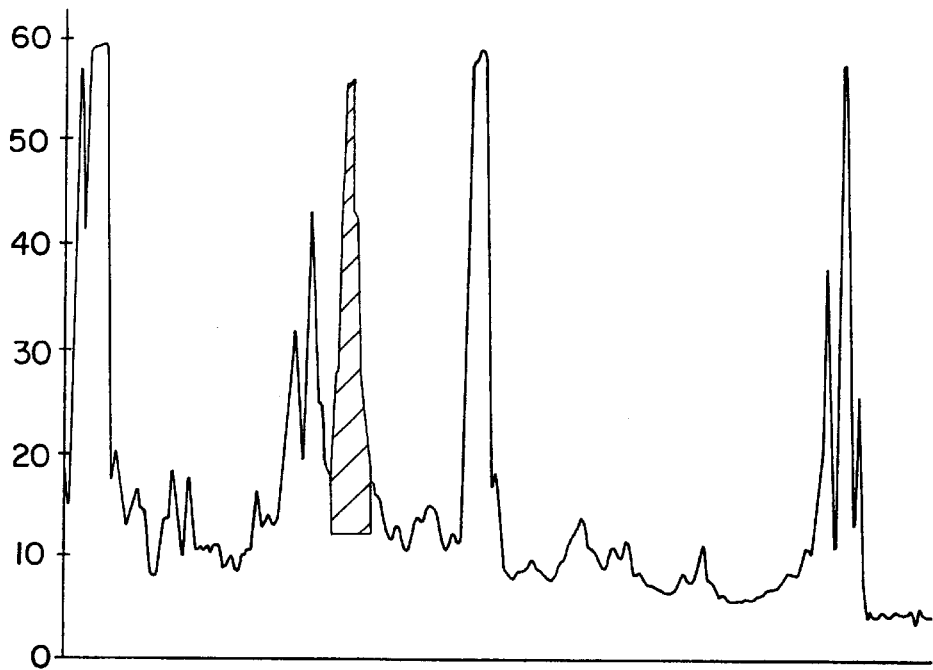

FIG. 22 shows the activity profile of HPLC fractionation of PAI from C. ruber ruber. Cross-hatched area contains the biologically active fractions.

Figure 23:
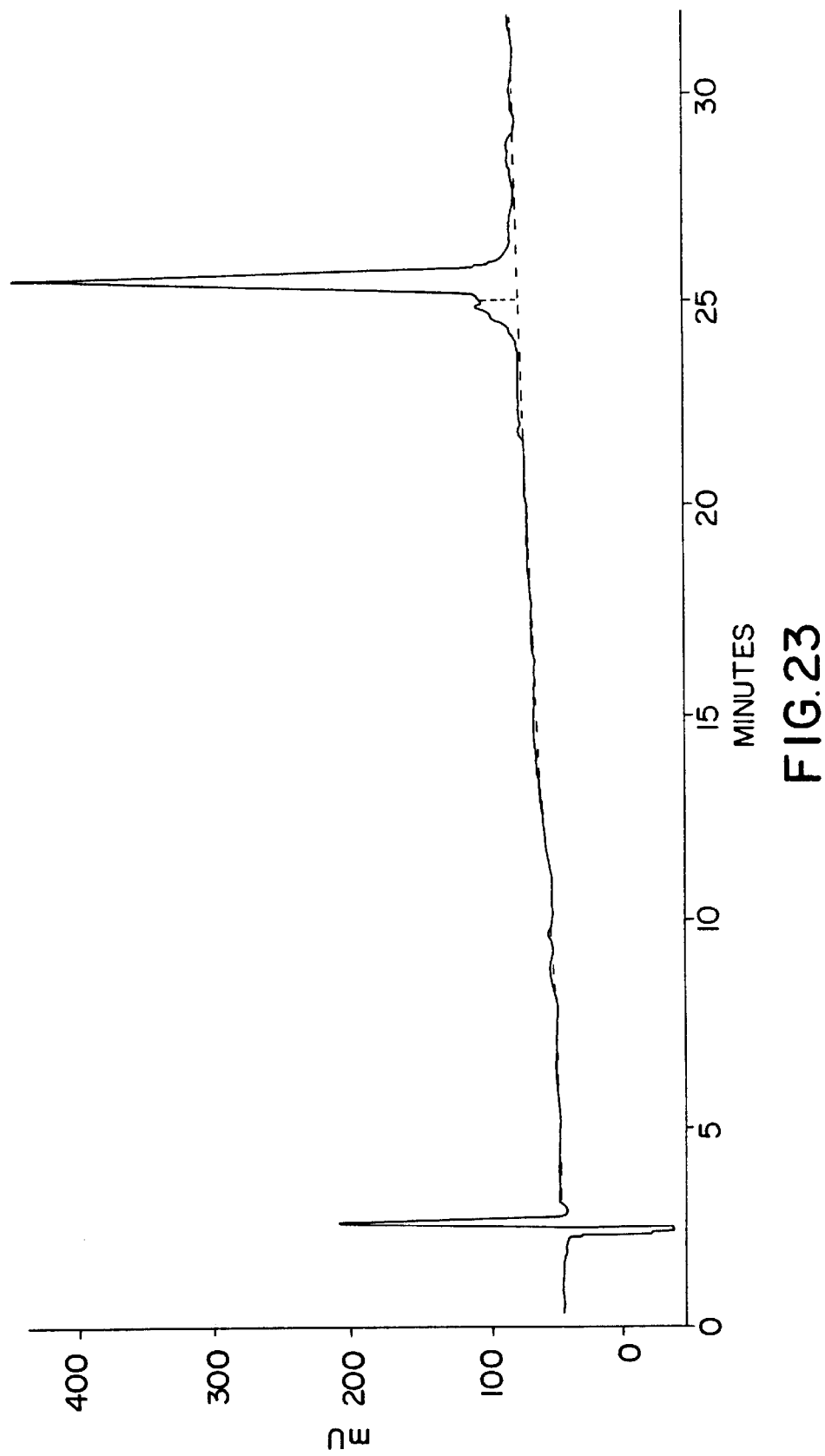

FIG. 23 shows the activity profile of an analytical C-18 column on homogeneous peptide obtained from C. atrox.

Figure 24:
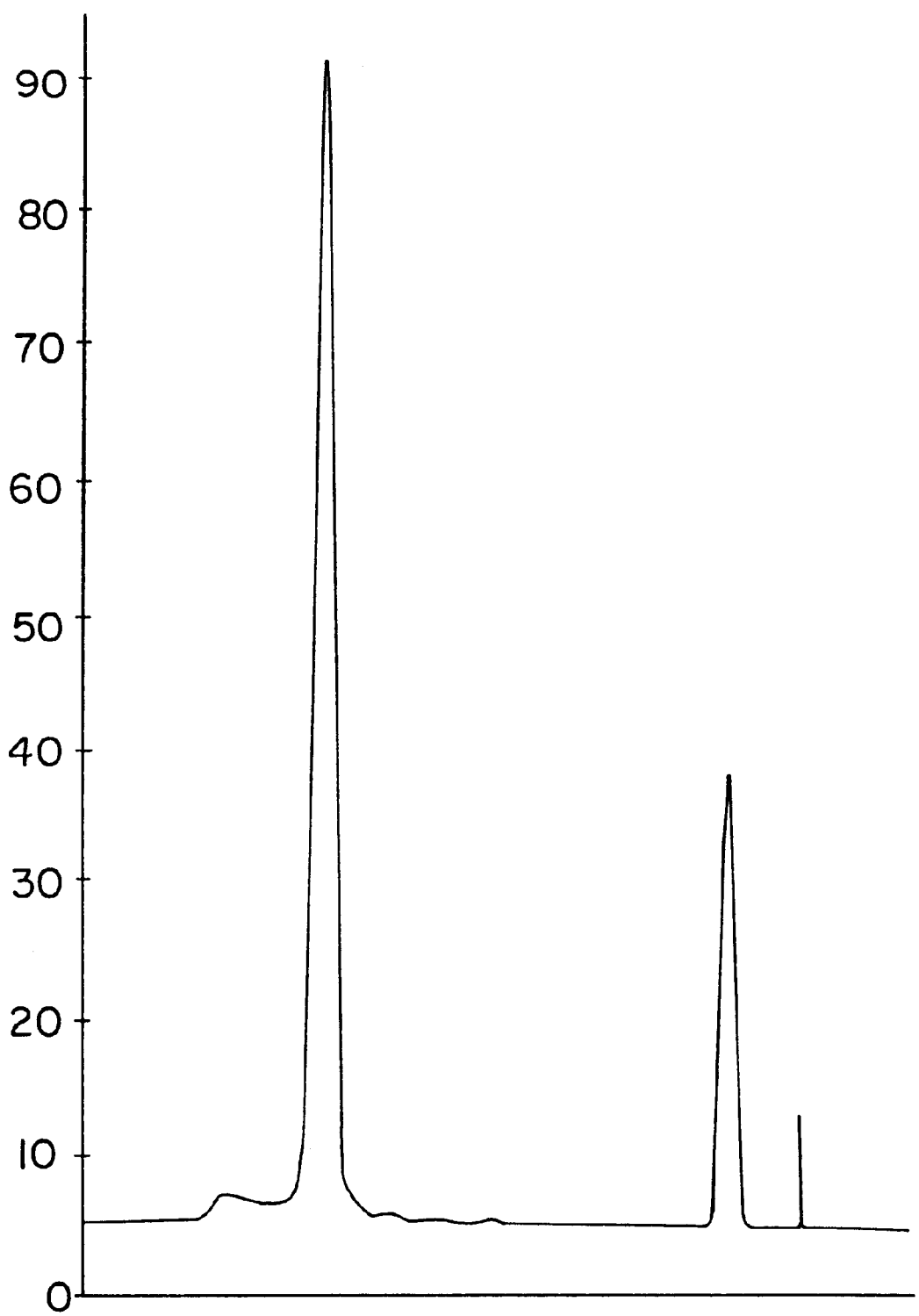

FIG. 24 shows the analytical HPLC profile of the homogeneous peptide isolated from Bothrops cotiara.

Figure 25:
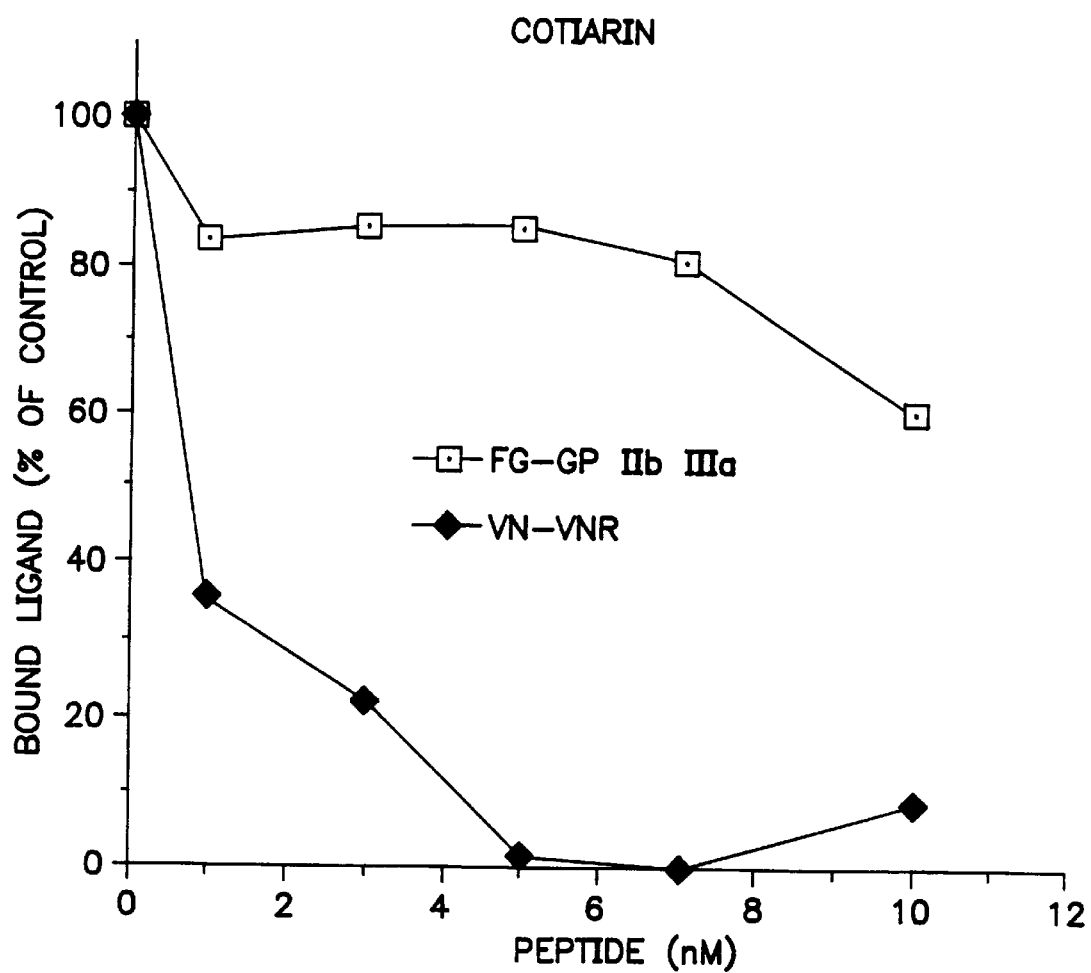

FIG. 25 shows the dose-response effects of purified cotiarin on inhibiting the binding of fibrinogen to GP IIb–IIIa and inhibition of the binding of vitronectin to the vitronectin receptor.

FIG. 26 shows the effects of purified snake venom peptides on binding of fibrinogen to GP IIb–IIIa and vitronectin to the vitronectin receptor. The values indicate the concentration of purified peptide which inhibits the binding of fibrinogen to GPIIb–IIIa or vitronectin to the vitronectin receptor by 50% (IC50). The symbol ">" indicates that the IC50 is greater than this value, which is the highest concentration examined to date. Note that substitution of the arginine in the "RGDW" sequence in Eristicophin with a lysine (KGDW) imparts specificity for inhibiting fibrinogen binding to GPIIb–IIIa versus vitronectin to the vitronectin receptor.

Figure 27:
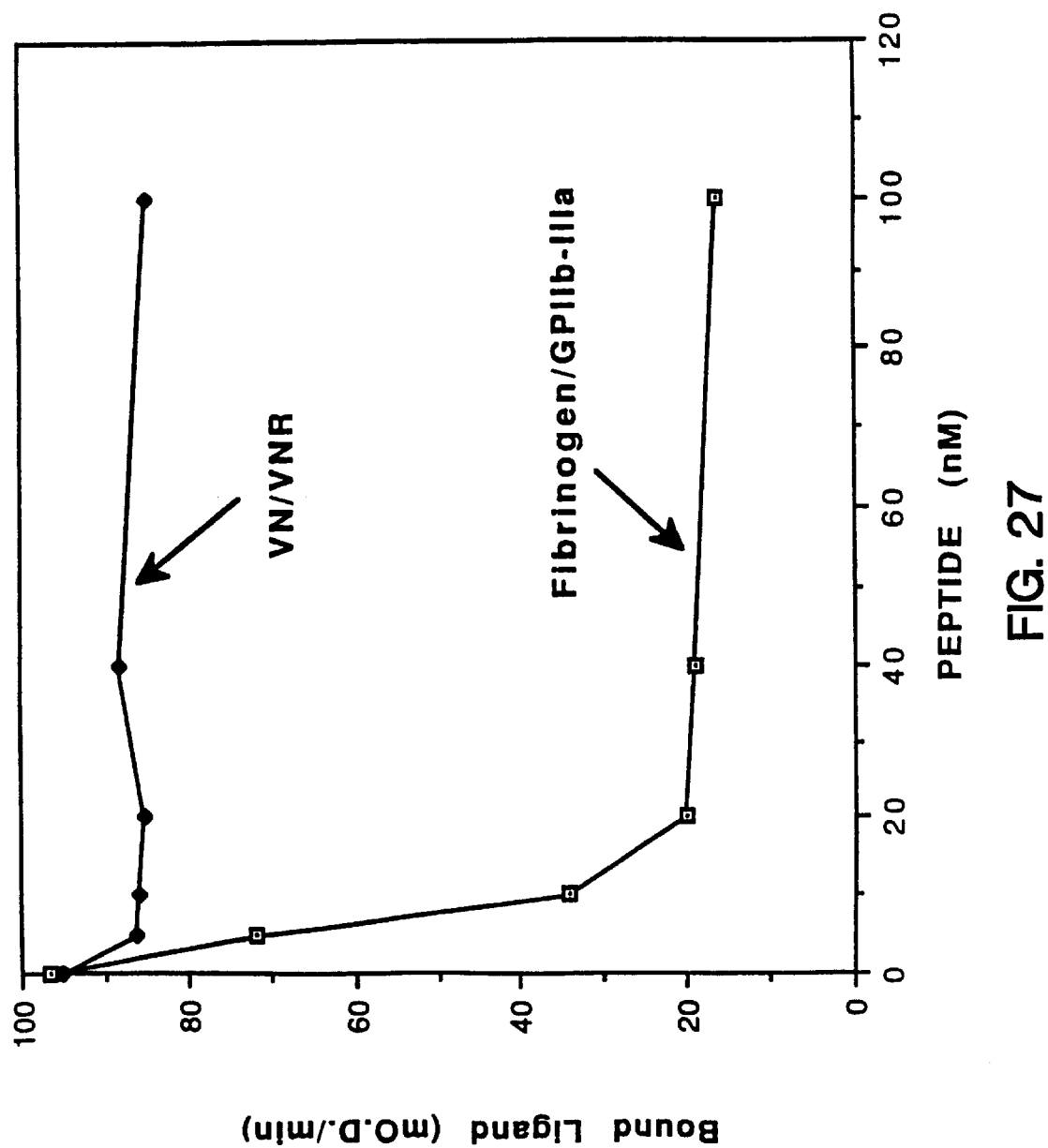

FIG. 27 shows the results of binding activity for analog #1, $[E^{28}L^{41}C^{64}]$barbourin (28–73), with regard to GP IIb–IIIa and vitronectin receptor.

Figure 28:
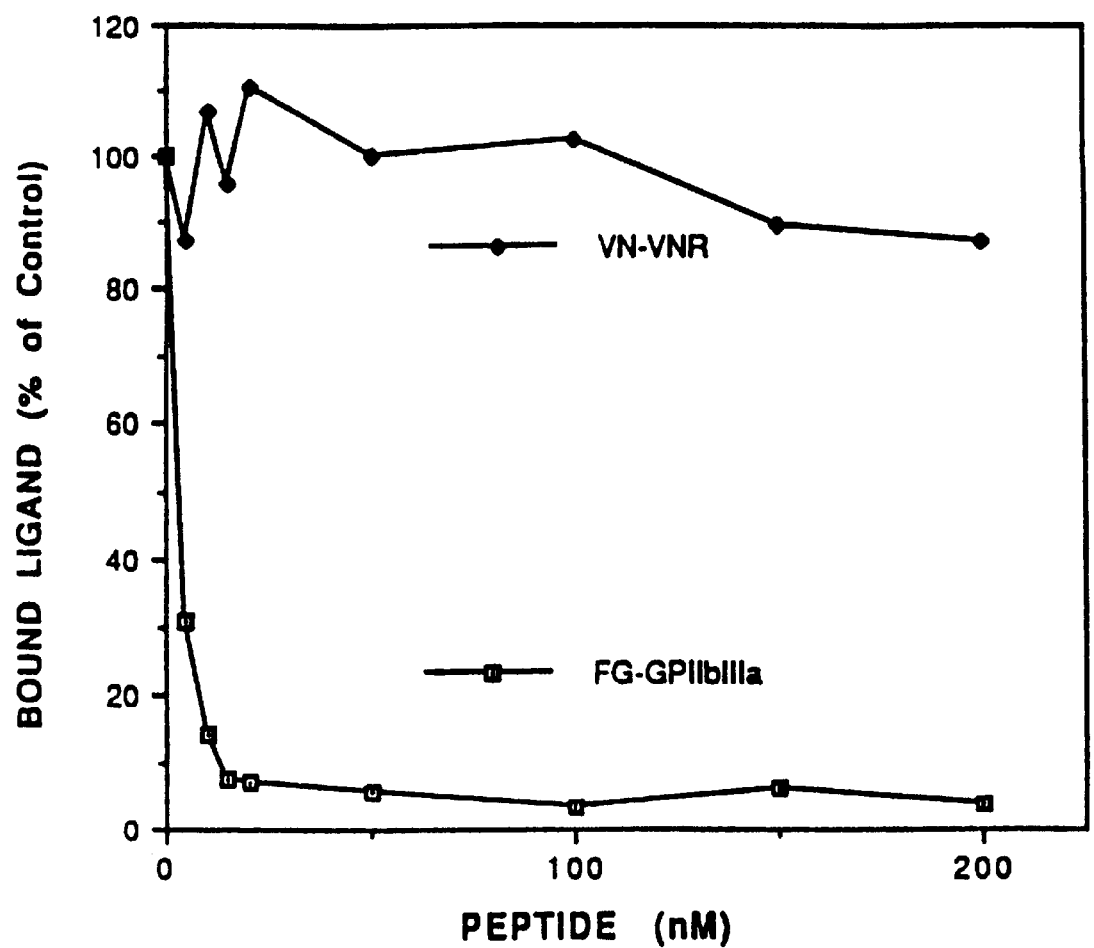

FIG. 28 shows the ability of synthetic eristicophin analog $[K^{29}]$-eristicophin (4–51) to inhibit the binding of fibrinogen to GP IIb–IIIa and inability to inhibit the binding of vitronectin to the vitronectin receptor.

Figure 29A:
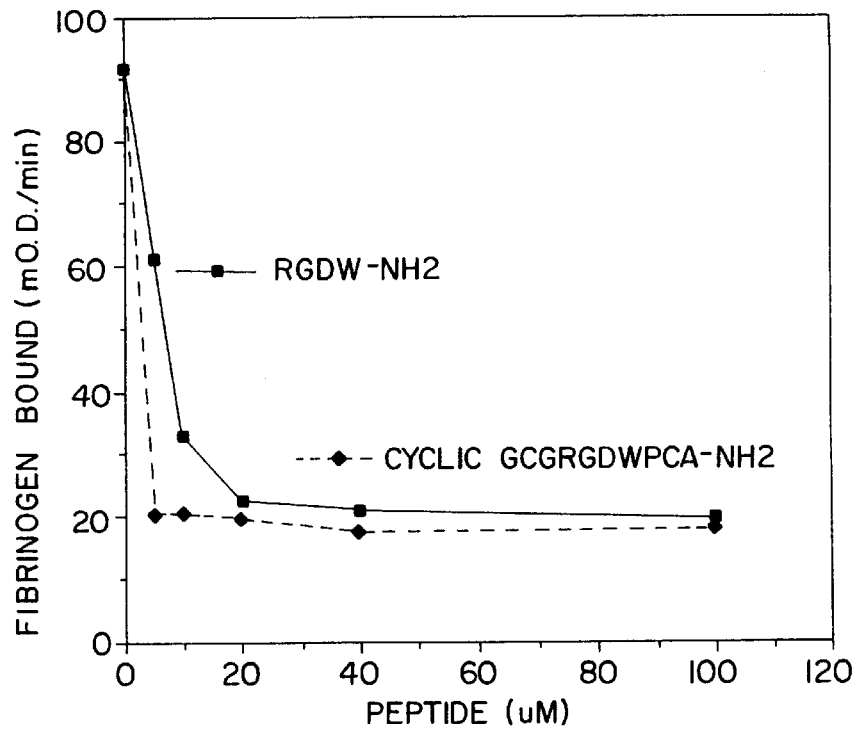
Figure 29B:
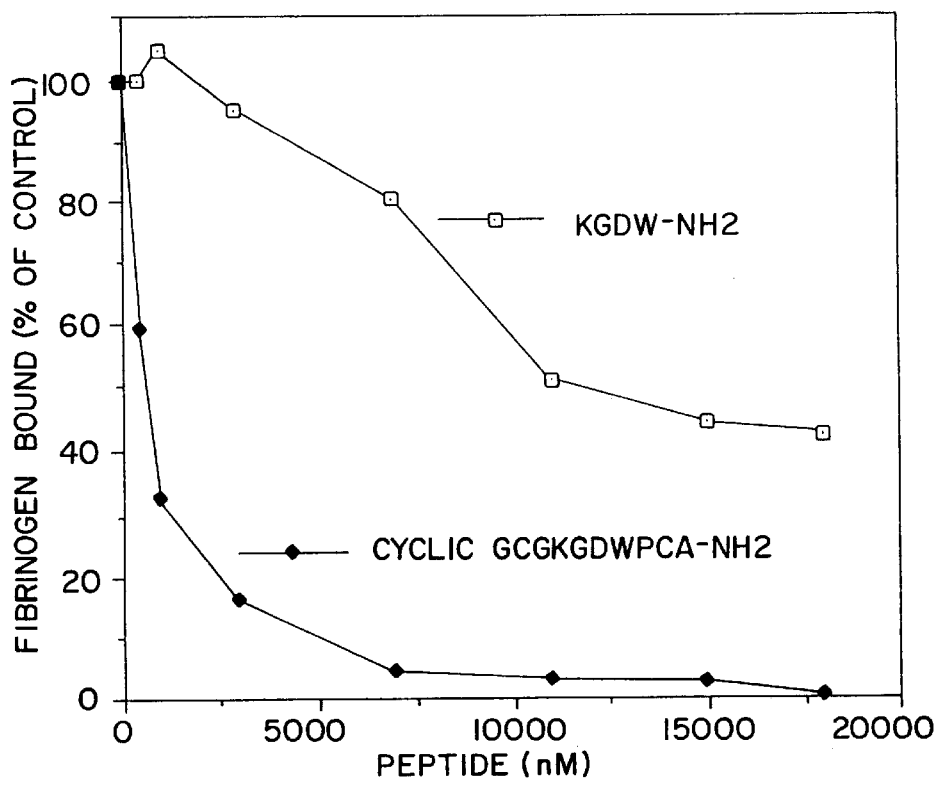

FIGS. 29A and 29B show the ability of linear and cyclic RGDW compounds and linear and cyclic KGDW compounds to inhibit the binding of fibrinogen to GP IIb–IIIa.

Figure 30A:
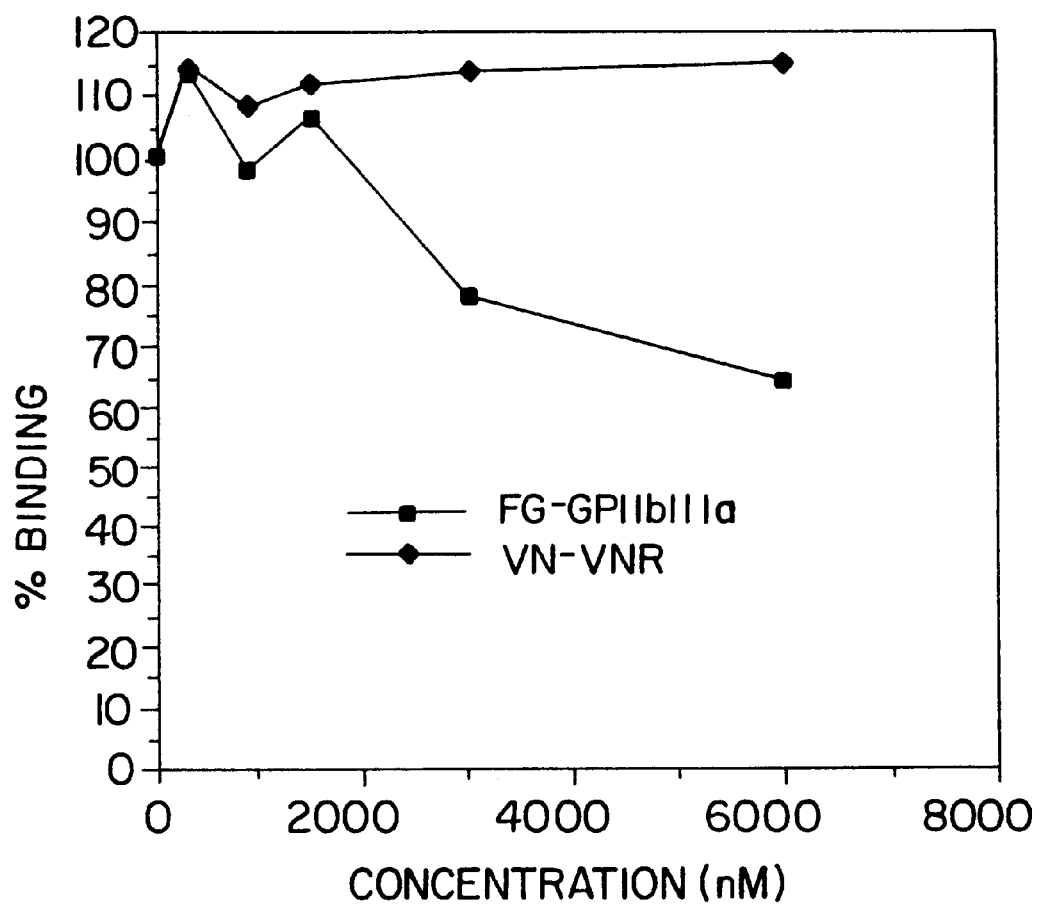
Figure 30B:
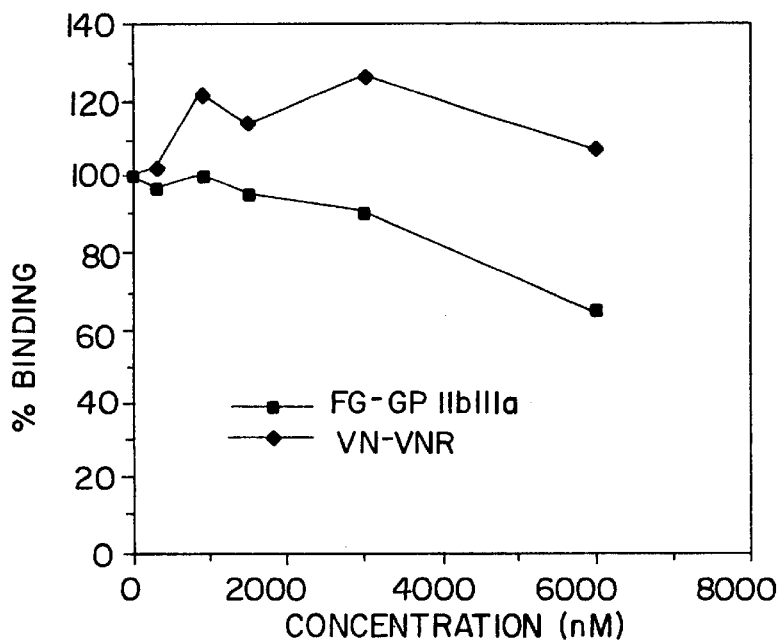
Figure 30C:
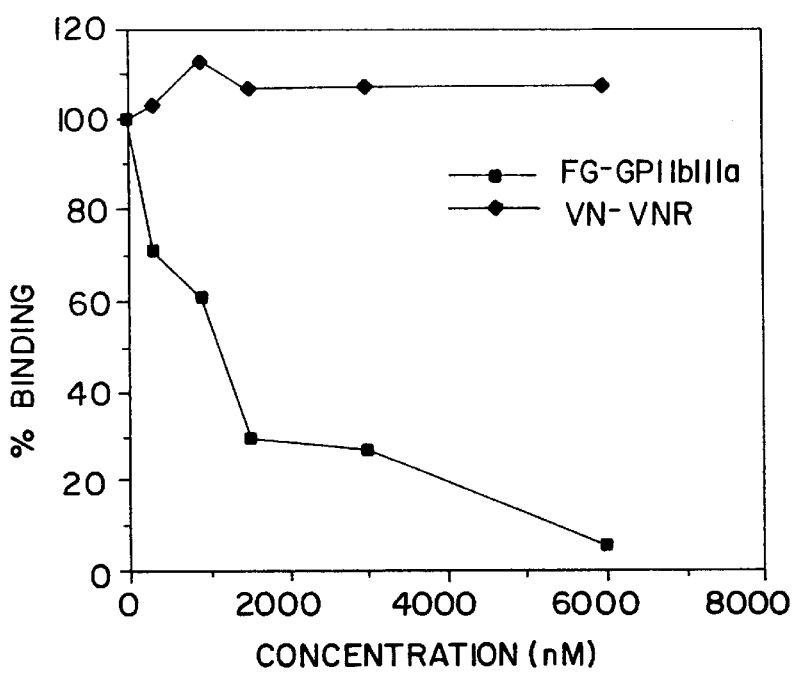
Figure 30D:
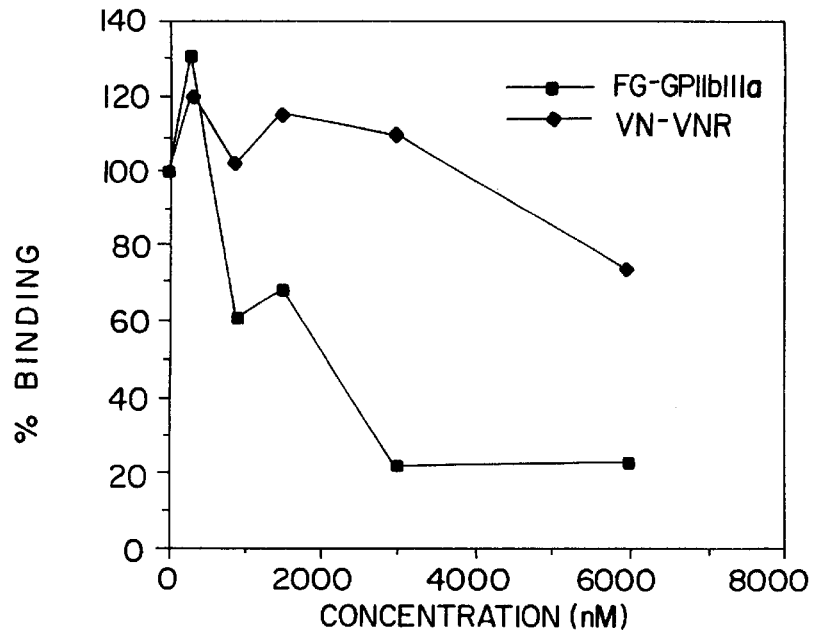
Figure 30E:
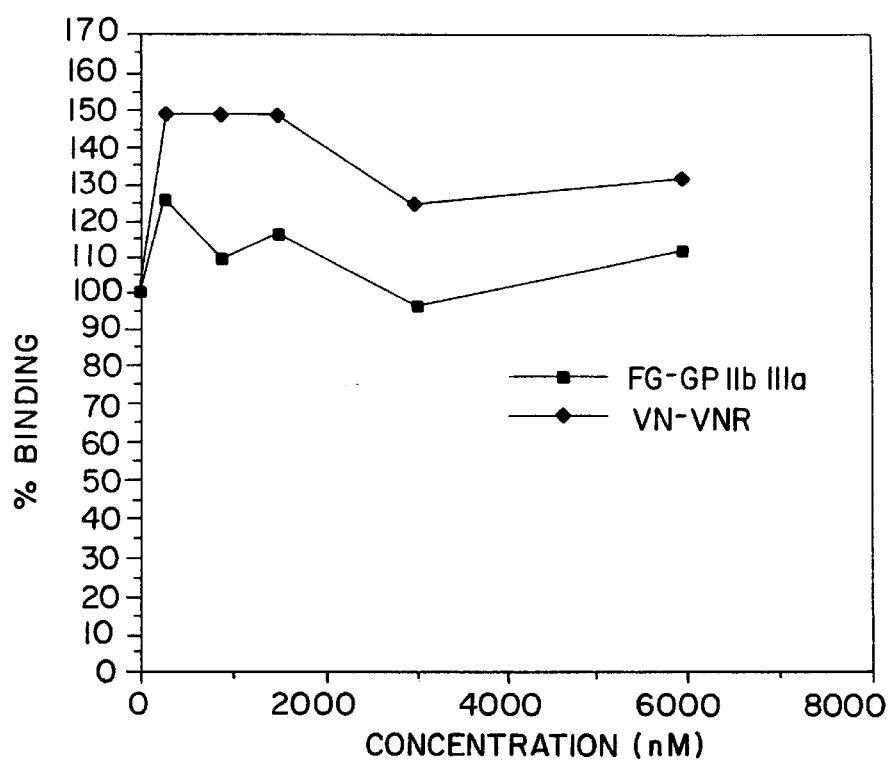

FIGS. 30A, 30B, 30C, 30D and 30E show the ability of various KGDW analogs to inhibit binding of fibrinogen to GP IIb–IIIa and inhibit binding of vitronectin to vitronectin receptor. FIG. 30A represents Analog #7. FIG. 30B represents Analog #8. FIG. 30C represents Analog #4. FIG. 30D represents Analog #5. FIG. 30E represents Analog #6.

Figure 31:
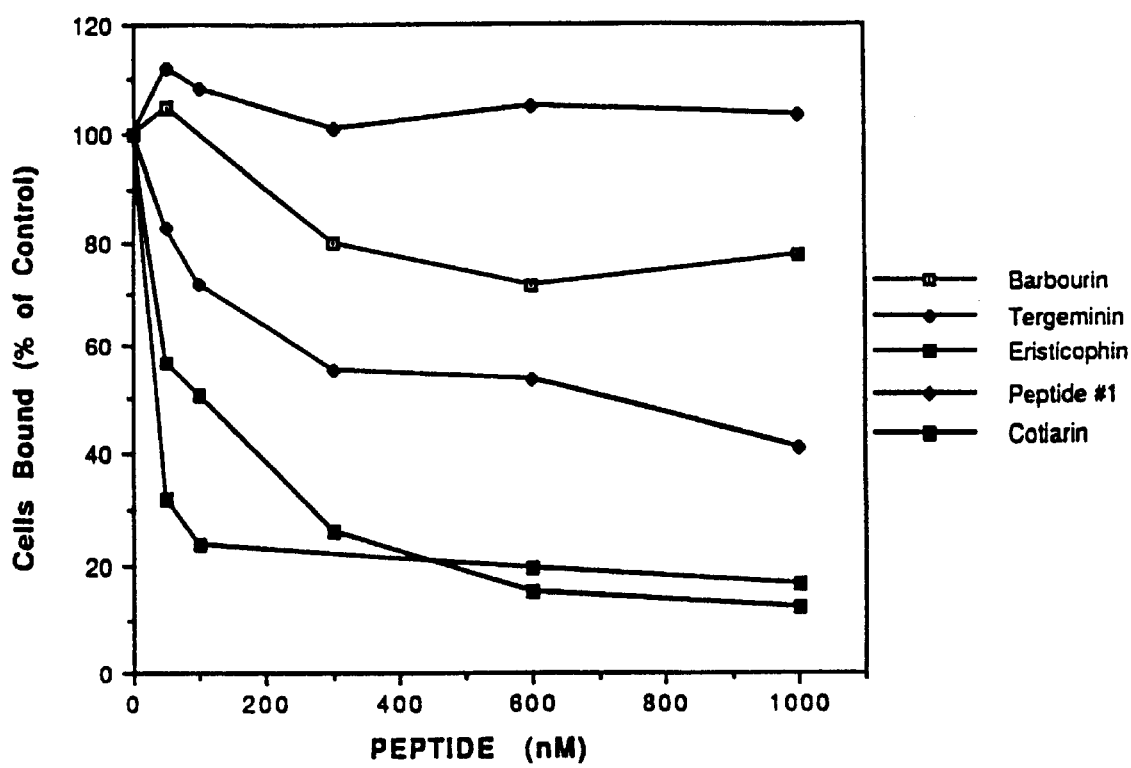

FIG. 31 shows the ability of various native and synthetic platelet aggregation inhibitors to inhibit the attachment of M21 melanoma cells to vitronectin.

Figure 32:
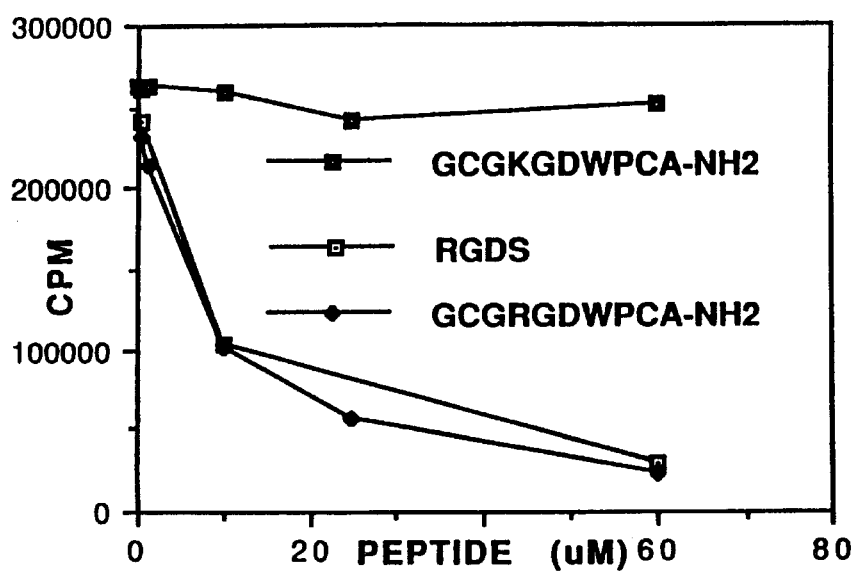

FIG. 32 shows the ability of RGDS and a cyclic RGD compound to inhibit the attachment of M21 melanoma cells to vitronectin and the lack of ability of a cyclic KGDW analog to inhibit the attachment of M21 melanoma cells to vitronectin.

Figure 33:
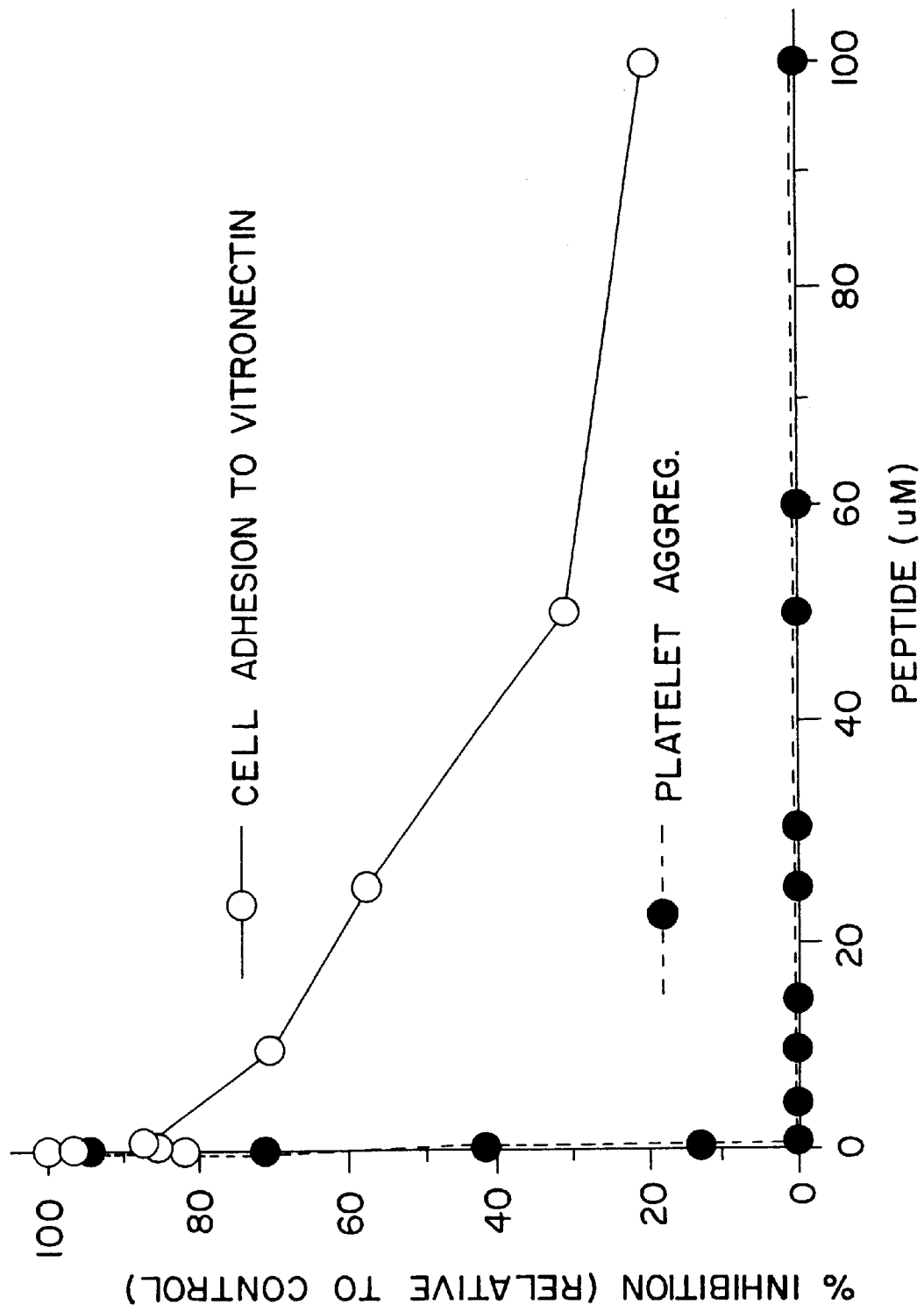

FIG. 33 shows the activity of analog number 60, Mpr-(Har)-G-D-W-P-C-NH$_2$, in inhibiting aggregation of platelets and cell adhesion to vitronectin.

Figure 34:
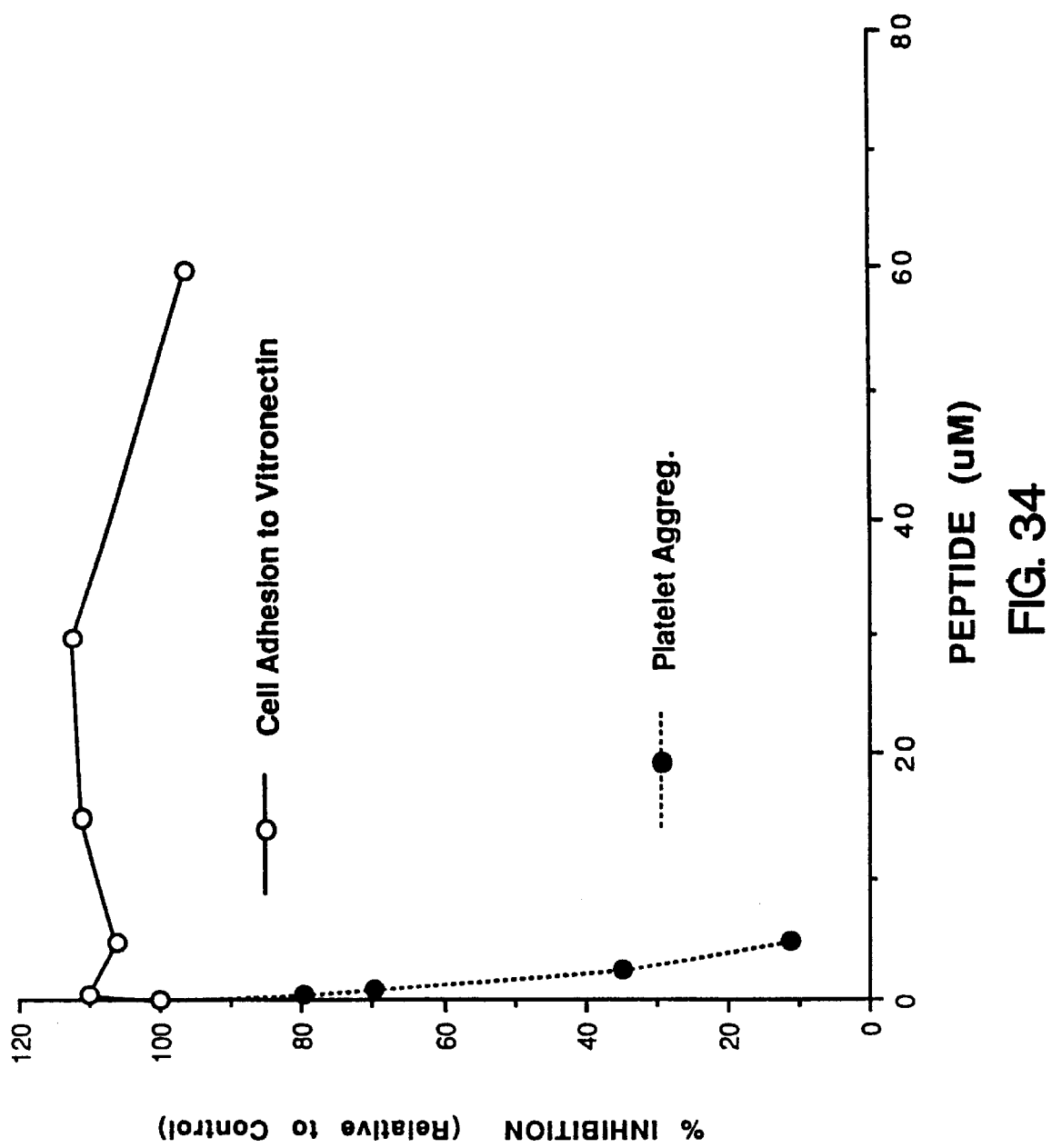

FIG. 34 shows the activities of FIG. 33 for analog 19, Mpr K-G-D-W-P-C-NH$_2$.

Figure 35:
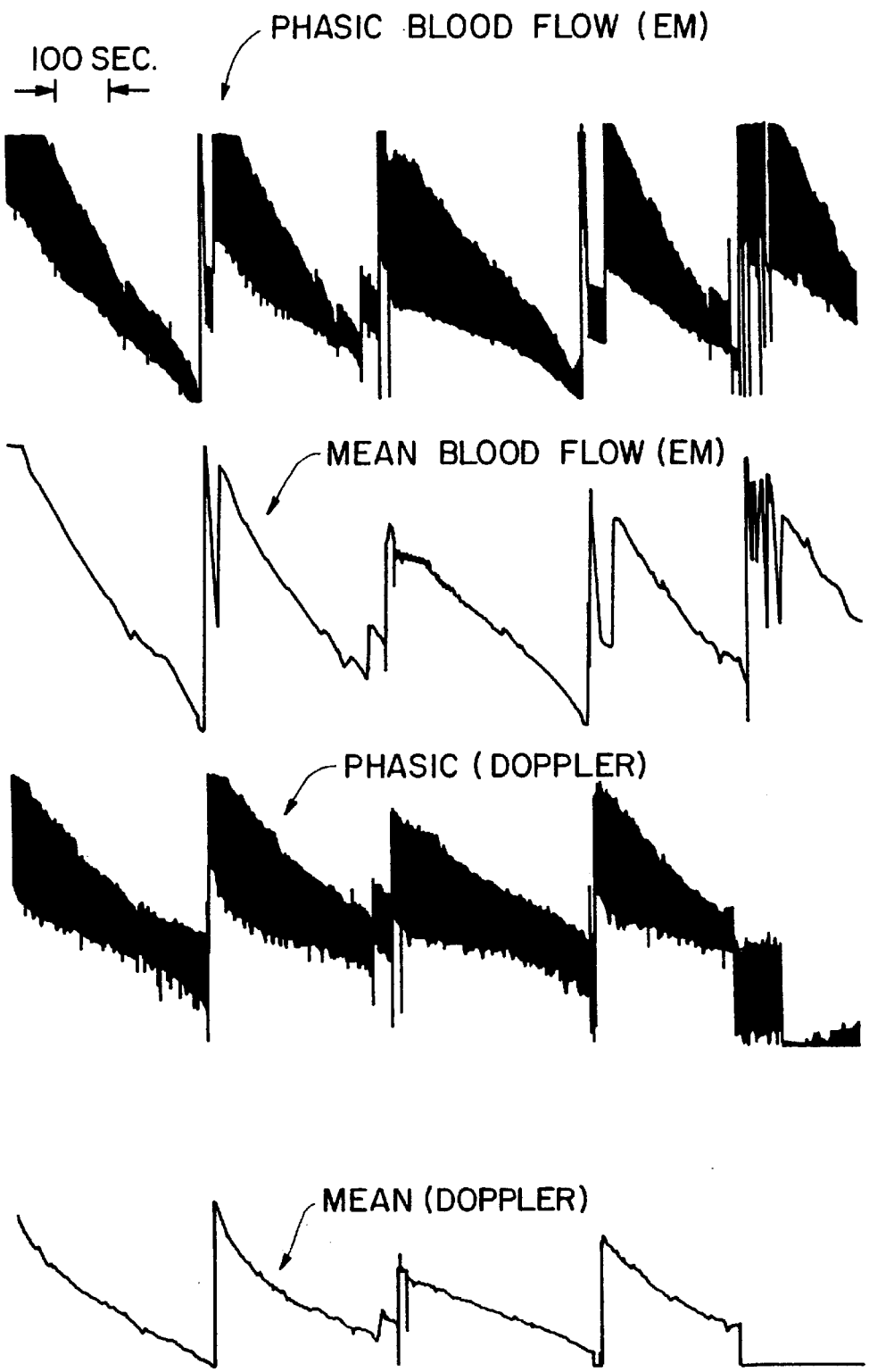

FIG. 35 shows the initiation of cyclic flow reductions (CFRs) in an open chest dog model of thrombosis (Folts Model).

Figure 36:
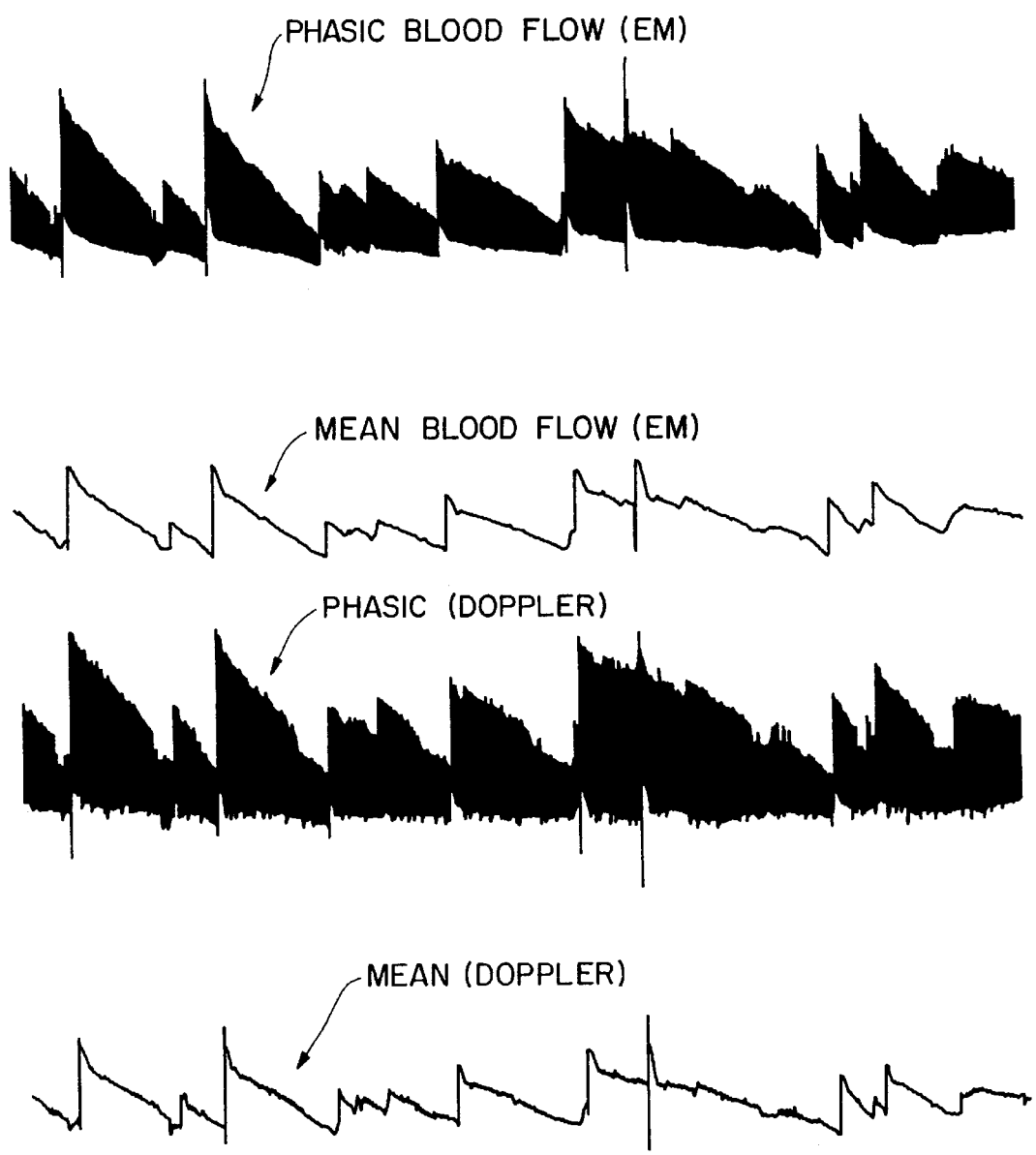

FIG. 36 shows the effects of a 10 mg bolus dose administration on the CFRs initiated in the open chest dog model of thrombosis (Folts Model).

Figure 37:
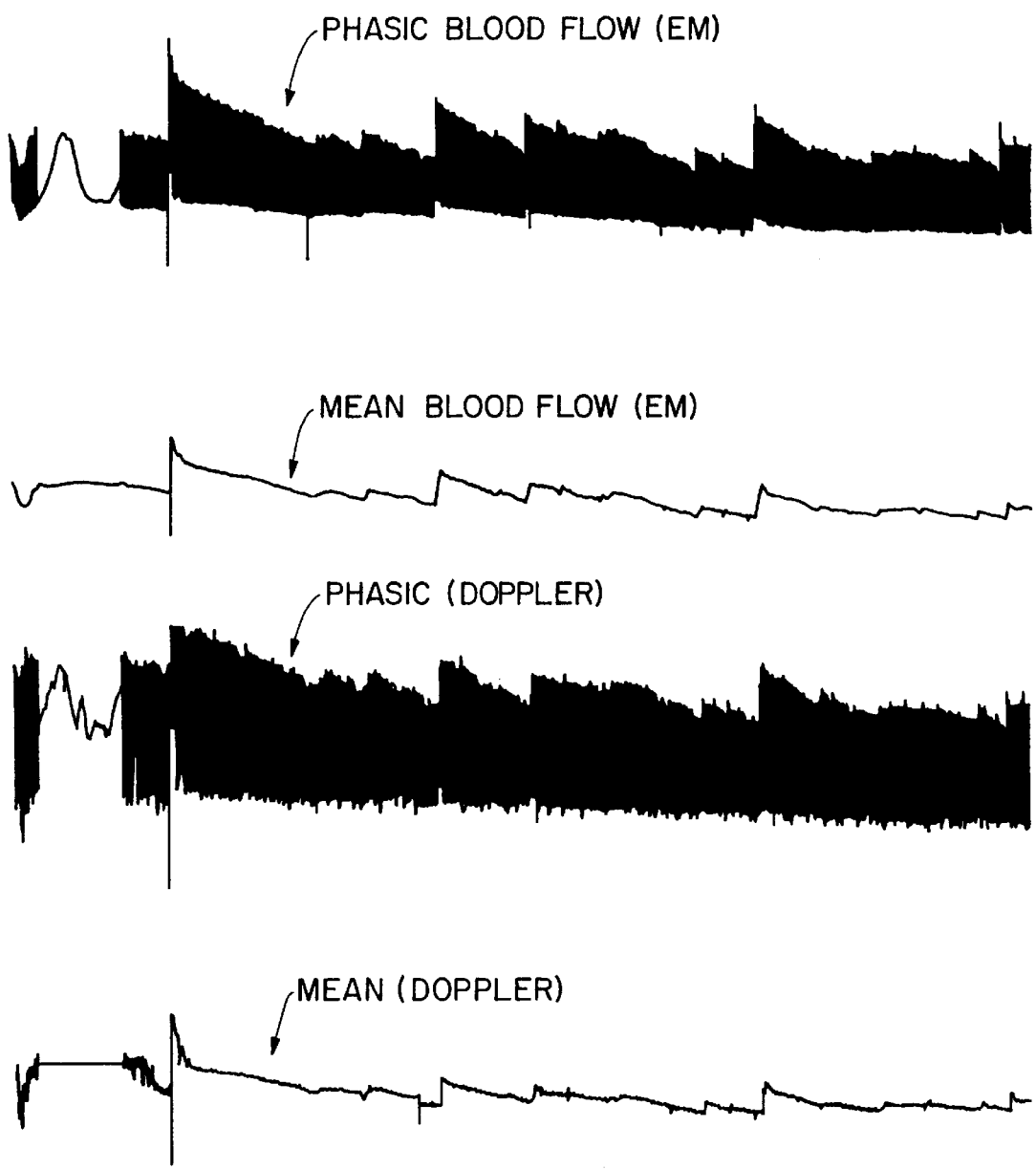

FIG. 37 shows the effects of a 40 mg bolus dose administration on the CFRs initiated in the open chest dog model of thrombosis (Folts Model).

FIG. 38 shows the full-length DNA sequence encoding the amino acid sequence of barbourin (1–73).

FIG. 39 shows the DNA sequence encoding [$M^{-1}, L^{41}$] barbourin(1–73) ligated to a PhoA leader sequence.

FIG. 40 shows the DNA sequence encoding analog #1, [$E^{28}$, $L^{41}$, $C^{64}$]barbourin (28–73), linked to a PhoA leader sequence for expression in bacteria.

FIGS. 41A and 41B show oligonucleotides utilized in a PCR reaction to obtain DNA encoding analog #1. The amino acids included in the analog per se are shown in boldface type.

Figure 42:
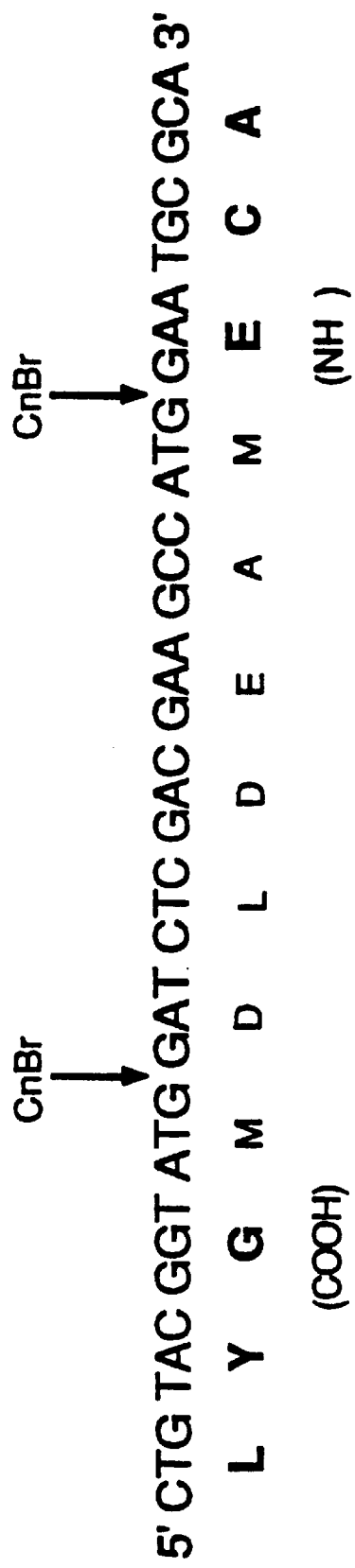

FIG. 42 shows the junction sequence of tandem repeats of the analog #1-encoding DNA.

Figure 43A:
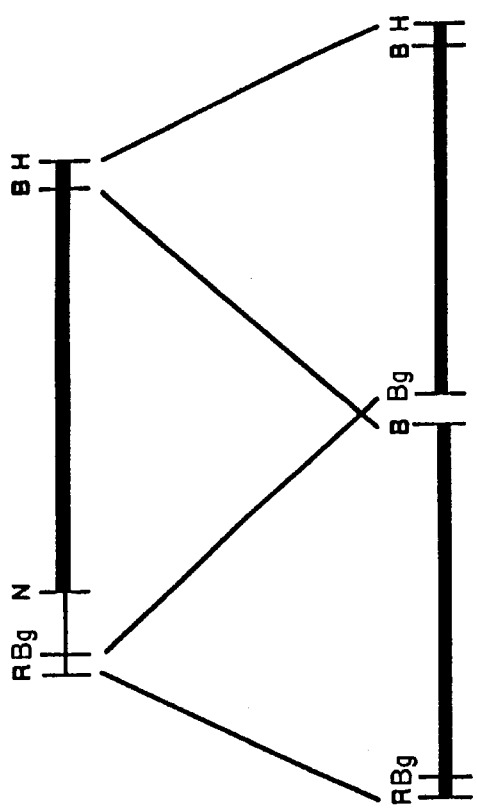
Figure 43B:
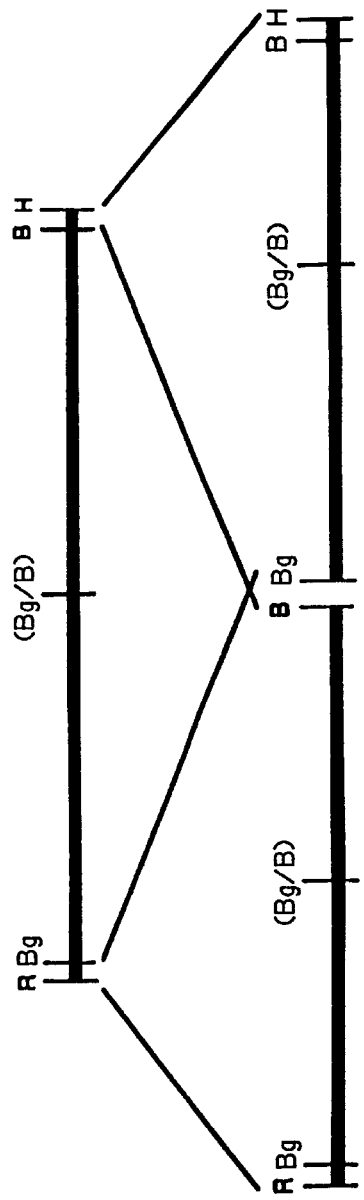

FIGS. 43A and 43B show a diagram of the truncated barbourin gene as tandem repeats.

MODES OF CARRYING OUT THE INVENTION

The invention provides platelet aggregation inhibitors (PAI) which may be isolated from snake venom which has been identified as active by the assay methods of the invention and compounds which have similar structures and are synthesized using standard in vitro techniques, such as solid phase peptide synthesis, or using recombinant methods, or combinations of these. Some of these inhibitors are uniquely specific for inhibition of platelet aggregation and do not inhibit alternate binding within the integrin family. Others have different ranges of specificity. The sections below describe the isolation of naturally occurring PAI from snake venom; the design of inhibitors which are of substantially higher potency in inhibiting platelet aggregation than in inhibiting, for example, vitronectin/vitronectin receptor interaction by incorporating a K* GD sequence in preference to RGD; methods of synthesizing these peptides; methods of recombinant production; antibodies raised against the invention peptides; the assay method which permits identification of snake venoms which contain PAI; and the administration and utility of the PAI of the invention.

By PAI is meant a factor which is capable of preventing the aggregation of stimulated platelets in standard assays, for example those described by Gan, Z.-R., et al., and Huang, T.-F., et al., (supra). In these assays, washed platelets are combined with fibrinogen, $Ca^{+2}$ and the material to be tested. The platelets are stimulated with ADP (or other known stimulators or combinations thereof) and aggregation (or lack thereof) is observed using, for example, a commercially available aggregometer.

Some of the PAIs of the invention are identified as specific for the inhibition of binding of fibrinogen and/or vWF to GP IIb–IIIa. It is understood that specificity is a matter of degree; therefore, a PAI specific for inhibition of Fg or vWF binding to GP IIb–IIIa inhibits this binding substantially more than it inhibits the binding of Fn to FnR, or Vn to VnR. By "substantially more" is meant that either the % inhibition is at least twofold greater at a given concentration of PAI or that the concentration of PAI that causes 50% inhibition is at least twofold less for Fg or vWF/GP IIb–IIIa binding inhibition than for alternate ligand/receptor binding.

Isolated Native PAI and Purification Methods

The platelet aggregation inhibitors (PAI) of the invention include low molecular weight peptides which can be prepared in isolated form, as described below, from snake venom which has been identified as "active", i.e., has been found to contain PAI using the method of the invention, which is described hereinbelow.

The invention method permits ready identification and characterization of the presence of an effective PAI in snake venom which selectively inhibits binding to GP IIb–IIIa as opposed to other integrins as, for example, the vitronectin receptor and the fibronectin receptor. Upon such identification, and, optionally and optimally, characterization, the PAI can be isolated and purified using a variety of standard techniques illustrated herein and disclosed in the art. For example, a combination of separation based on molecular weight (typically recovery of substances of <10 kd), ion exchange chromatography, and reverse phase HPLC can be used. Other techniques can also be employed, but a workable procedure applicable to PAI from any active snake venom is as follows:

About 10–1000 mg venom is dissolved in dilute acetic acid and applied to a sizing column, such as Sephadex G-50, and eluted in the same solvent. Fractions are assayed for activity using the Fg/GP IIb–IIIa binding assay of the invention, a standard platelet aggregation assay (PAA) or any similar assay relying on the adhesive protein binding activity of GP IIb–IIIa. Alternatively, the <10 kd fraction of the fraction of the venom can be recovered using ultrafiltration and similarly assayed.

The low MW fraction isolated by either procedure is then loaded onto a preparative C-18 HPLC column, such as a C-18 Delta Pak reverse phase HPLC column, available from Waters, preequilibrated in 0.1% trifluoroacetic acid (TFA)/ 8% acetonitrile. The adsorbed PAI is then eluted using a gradient of 8%–60% acetonitrile in 0.1% TFA. The slope of the gradient and flow rate are optimized using routine procedures. Active fractions are determined by PAA or by the invention receptor binding method. The active fractions are then pooled, concentrated, and tested for homogeneity using analytical HPLC or SDS-PAGE. Further reverse-phase HPLC gradient purification is applied until the recovered PAI is homogenous.

PAIs of the invention, obtainable by the foregoing or other purification methods include those from venoms selected from the group consisting of *Echis colorata, Eristicophis macmahonii; A. hypnale, A. acutus, A. piscivorous leucostoma, A. piscivorus conanti; Bothrops asper; Bothrops cotiara, B. jararaca, B. jararacussu, B. lansbergi, B. medusa, B. nasuta, B. neuwiedi, B. pradoi, B. schlegli; Crotalus atrox, C. basilicus, C. cerastes cerastes, C. durissus durissus, C. durissus totonatacus, C. horridus horridus, C. molossus molossus, C. ruber ruber, C. viridis cereberus, Crotalus v. helleri, Crotalus v. lutosus, Crotalus v. oreganus, Crotalus v. viridis; Lachesis mutas; Sistrurus catenatus tergeminus*, and *Sistrurus milarus barbouri*.

Preferred are PAIs in isolated form prepared from, or having the amino acid sequences of, those obtained from *Eristicophis macmahonii* (eristicophin); *Bothrops cotiara* (cotiarin); *B. lararacussu; Crotalus atrox* (crotatroxin); *Crotalus basilicus* (basilicin); *C. cerastes cerastes* (cerastin); *C. durissus totonatacus; Crotalus d. durissus; C. h. horridus* (horridin); *Crotalus m. molossus* (molossin); *C. ruber ruber* (ruberin); *Crotalus viridis lutosus* (lutosin); *C. v. viridis* (viridin); *Crotalus v. oreganus; Crotalus v. helleri; Lachesis mutas* (lachesin); *Sistrurus catenatus tergeminus* (tergeminin); and *S. milarus barbouri* (barbourin). Particularly preferred are PAI specific for inhibiting Fg or vWF/GP IIb–IIIa binding, e.g., that from *Sistrurus m. barbouri*.

Especially preferred are eristicophin, cotiarin, crotatroxin, cerastin, horridin, ruberin, lachesin, basilicin, lutosin, molossin, viridin, tergeminin and barbourin.

The purified PAI of the invention can be sequenced using standard procedures, thus permitting synthesis using standard solid phase techniques (in particular for shorter forms of the PAI) or recombinant production. For example, an Applied Biosystems Sequenator can be used following carboxyamido methylation or pyridylethylation of the peptide as described by Huang et al., *J Biol Chem* (1987) 262:16157–16163 followed by desalting of the sample on a C-18 Delta Pak column using 0.1% TFA and acetonitrile.

It is understood that the isolated PAI of determined sequence can, when synthesized in vitro, be modified by sequence alterations which do not destroy activity. In general, these modified forms will differ from the native forms by 1–10, preferably 1–4, amino acid substitutions or will be truncated forms. In addition, one or more peptide linkages may be replaced by alternate linkages as described hereinbelow. A particularly preferred substitution is replacement of RGD by KGD to confer GP IIb–IIIa specificity as described below.

The PAI of *Sistrurus m. barbouri* has been purified to homogeneity and sequenced, and termed "barbourin". Unlike the adhesive proteins for GP IIb–IIIa so far identified and the peptides from snake venoms that block GP IIb–IIIa function, barbourin does not contain the standard Arg-Gly-Asp sequence of the adhesive proteins known in the art. The apparent binding sequence in barbourin is Lys-Gly-Asp-(Trp). The presence of the KGD sequence in the apparent binding region of this peptide is especially surprising in view of the observation that replacement of Lys for Arg in small synthetic peptides based on the RDGX sequence greatly decreases the ability of these peptides to bind to integrin receptors (Pierschbacher et al., *Proc Natl Acad Sci* (USA) (1984) 81:5985–5988; Williams et al., *Thromb Res* (1987) 46:457–471); Huang et al., *J.Biol Chem* (1987) 262:16157–16163. It is thought that this substitution may in part be responsible for the specificity of the barbourin peptide to inhibit Fg and vWF binding to GP IIb–IIIa, versus, for example, inhibition of vitronectin binding to the vitronectin receptor.

K*GDX-Containing Peptides

The "barbourin" peptide isolated by the method of the invention has been shown to have the binding sequence KGDX in contrast to the RGDX found in the PAI compounds of the prior art. The presence of the KGDX in this PAI sequence appears to be associated with a preferential affinity for GP IIb–IIIa as opposed to the vitronectin or fibronectin receptors. The effect of the substitution of a lysyl residue for an arginine in the sequence appears to be associated with increased length of the sidechain along with retained basicity of the nitrogen as is further described hereinbelow. Surprisingly, it appears that it is not the lysyl residue per se which accounts for the enhanced activity and specificity, but rather the spacing provided by this homologous extension of the replaced arginine. Thus, the peptides of the invention which contain K*GDX in the binding sequence are substantially more potent in inhibiting the binding of Fg or vWF to GP IIb–IIIa as compared to their ability to inhibit the binding of vitronectin to the vitronectin receptor and the binding of fibronectin to the fibronectin receptor. As stated above, by "substantially more" potent in inhibiting the preferred binding is meant that the percent inhibition is at least 2-fold greater at a set concentration of inhibitor or that the concentration of PAI that causes 50% inhibition is at least 2-fold less for the binding of Fg or vWF to GP IIb–IIIa than for the binding of alternate ligands to other integrins.

As used herein K* refers to a lysyl residue which is unsubstituted, or which contains substitutions for the hydrogens on the epsilon amino group. The substituents must be sufficiently electron donating so as to maintain the basicity of the nitrogen to which they are attached. Thus, K* is defined as a lysyl residue of the formula $R^1_2$ $N(CH_2)_4$ CHNHCO—, wherein each $R^1$ is independently H, alkyl (1–6) or at most one $R^1$ is $R^2$—C=$NR^3$ wherein $R^2$ is H, alkyl (1–6C) or is $NR^4_2$ in which each $R^4$ is independently H or alkyl(1–6C) and $R^3$ is H, alkyl(1–6C), phenyl or benzyl, or $R^2$—C=$NR^3$ is a radical selected from the group consisting of:

where m is an integer of 2–3, and each $R^5$ is independently H or alkyl(1–6C);

and wherein one or two ($CH_2$) may be replaced by O or S provided said O or S is not adjacent to another heteroatom.

"Alkyl" is conventionally defined as a straight or branched chain or cyclic hydrocarbyl residue of the indicated number of carbon atoms such as methyl, ethyl, isopropyl, N-hexyl, 2-methylbutyl, cyclohexyl and the like.

As the essential feature of the preferential inhibition of binding appears to reside in the substitution of K* for R of RGDX, one class of peptides or peptide-related compounds of the invention comprises naturally occurring platelet aggregation inhibitors which ordinarily contain RGDX in the binding sequence whereby these forms are modified by substituting K* for R in this sequence. Included in the invention are the native peptides having this substitution, as well as their fragments of sufficient length to be effective in selectively inhibiting the binding of adhesive proteins to GP IIb–IIIa and fragments or full-length peptides which have irrelevant substitutions in positions of the peptide which do not destroy this activity. For the most part, the fragments will contain residues corresponding to the length of a peptide chain of at least 7 amino acids if the conformation is controlled by, for example, cyclization, and are of greater length if there is no such conformational control. In general, aside from the K*GDX required sequence, there may be 1–10, preferably 1–4, and more preferably 1–3 amino acid substitutions in the non-KGDX portion of the peptides.

Additionally, the G of RGDX or K*GDX may be replaced by a sarcosine residue.

In addition, one or more of the peptide bonds may be optionally replaced by substitute linkages such as those obtained by reduction or elimination. Thus, one or more of the —CONH— peptide linkages can be replaced with other types of linkages such as —$CH_2NH$—, —$CH_2S$—, $CH_2CH_2$—, —CH=CH— (cis and trans), —$COCH_2$—, —CH(OH)$CH_2$— and —$CH_2SO$—, by methods known in the art. The following references describe preparation of peptide analogs which include these alternative-linking moieties: Spatola, A. F., Vega Data (March 1983), Vol. 1, Issue 3, "Peptide Backbone Modifications" (general review); Spatola, A. F. in "Chemistry and Biochemistry of Amino Acids, Peptides and Proteins," B. Weinstein, eds., Marcel Dekker, New York, p. 267 (1983) (general review); Morley, J. S., *Trends Pharm Sci* (1980) pp. 463–468 (general review); Hudson, D. et al. *Int J Pept Prot Res* (1979) 14:177–185 (—CH$_2$NH—, CH$_2$CH$_2$—); Spatola, A. F. et al., *Life Sci* (1986) 38:1243–1249 (—CH$_2$—S); Hann, M. M. *J Chem Soc Perkin Trans I* (1982) 307–314 (—CH═CH—, cis and trans); Almquist, R. G., et al., *J Med Chem* (1980) 23:1392–1398 (—COCH$_2$—); Jennings-White, C. et al. *Tetrahedron Lett* (1982) 23:2533 (—COCH$_2$—); Szelke, M., et al., European Appln. EP 45665 (1982) CA: 97:39405 (1982) (—CH(OH)CH$_2$—); Holladay, M. W. et al. *Tetrahedron Lett* (1983) 24:4401–4404 (—C(OH)CH$_2$—); and Hruby, V. J. *Life Sci* (1982) 31:189–199 (—CH$_2$—S—). Particularly preferred is —CH$_2$NH—.

Examples of fragments and/or modified forms of the naturally-occurring snake venom PAI include [E$^{28}$, L$^{41}$, C$^{64}$]barbourin(28–73) of the sequence

```
 1                                              46
ECADGLCCDQCRFLKKGTVCRVAKGDWNDDTCTGQSCDCPRNGLYG
28                                              73
``` and [K$^{29}$]eristicophin(4–51) of the sequence

```
 4                                               51
EEPCATGPCCRRCKFKRAGKVCRVAKGDWNNDYCTGKSCDCPRNPWNG
 4                                               51
```

In this notation, the size of the fragment is noted in parentheses after the name by the numbers of the amino acids which are included in the fragment, and the bracketed prefix letters and numbers indicate amino acid substitutions at the numbered positions in the native full-length peptide. Thus, for the barbourin fragment above, the length of the fragment spans residues 28–73 inclusive of the native sequence and the amino acids originally in positions 28, 41 and 64 of the numbered native sequence have been replaced by Glu (E), Leu (L), and Cys (C), respectively.

As additional examples, the arginine of the RGD sequence appearing in trigramin, elegantin, albolabrin, crotatroxin, flavoviridin, echistatin, bitistatin, viridin, molossin, lutosin, basilicin, applagin, halysin, horridin, tergeminin, lachesin, cotiarin, and ruberin can be replaced by a K* residue to provide specifically active PAIs with a preferential affinity for GP IIb–IIIa. In addition, shortened forms of these peptides, containing at least 20, preferably at least 30, and more preferably at least 40, amino acids, can be prepared from the native peptide or in this modified form. In addition, or in the alternative, 1–10, preferably 1–4, amino acids irrelevant to the RGD/K*GD sequence can be substituted or modified, preferably with conservative amino acid substitutions. By conservative amino acid substitutions is meant, for example, substitution of an acidic amino acid residue for an acidic amino acid residue, neutral for neutral, basic for basic, etc., as is further described hereinbelow.

Still an additional group of examples includes that wherein the glycyl residue of RGD or KGD can be replaced by a sarcosyl residue with retention of activity. Thus, the active PAIs which are isolated and/or modified in other ways as described above may further be modified by this substitution.

While fragments and/or modified PAIs from snake venom can be included among the Fg/vWF/GP IIb–IIIa binding-specific compounds of the invention by replacing RGD by K*GD, in additional embodiments of the invention specifically active peptides are based on compatible extensions of the K*GD sequence per se. In this regard, a preferred group of peptides or peptide-related compounds of the invention are cyclic peptides of the general formula:

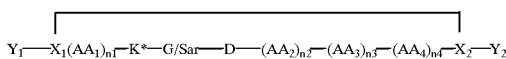

(1)

wherein K* is substituted or unsubstituted lysyl as above defined;

AA$_1$ is a small, neutral (polar or nonpolar) amino acid and n1 is an integer of 0–3;

AA$_2$ is a neutral, nonpolar large (aromatic or nonaromatic) or a polar aromatic amino acid and n2 is an integer of 0–3;

AA$_3$ is a proline residue or a modified proline residue, and n3 is an integer of 0–1;

AA$_4$ is a neutral, small amino acid and n4 is an integer of 0–3;

each of X$_1$ and X$_2$ is independently a residue capable of forming a bond between X$_1$ and X$_2$ to obtain a cyclic compound as shown; and each of Y$_1$ and Y$_2$ is independently a noninterfering substituent or may be absent;

wherein one or more peptide linkages may optionally be replaced by a linkage selected from the group consisting of —CH$_2$NH—, —CH$_2$S—, CH$_2$CH$_2$—, —CH═CH— (cis and trans), —COCH$_2$—, —CH(OH)CH$_2$— and —CH$_2$SO—.

Y$_1$ and Y$_2$ can be peptide extensions of 0–25 amino acid residues and may be in derivatized form. The Y$_1$ N-terminal extension may, for example, be acetylated or otherwise acylated; the Y$_2$ C-terminal extension may be amidated with NH$_2$ or with a primary or secondary amine of the formula R—NH$_2$ or R$_2$NH wherein each R is independently a lower alkyl of 1–4C such as methyl, n-butyl, or t-butyl. Y$_1$ can also be (H) or acyl; Y$_2$ can be (OH), NH$_2$ or an amine as above. Where the compound of formula (1) is a simple cyclic peptide, Y$_1$ and Y$_2$ are absent.

X$_1$ and X$_2$ are typically amino acid residues capable of cyclization such as, for example and most preferably, cysteine residues capable of forming a disulfide ring. However, other residues capable of forming disulfide or other linkages may also be used—for example, the Pen (penicillamine) residue described by Pierschbacher et al. (supra) or the Mpr (mercapto propionyl) or Mvl (mercaptovaleryl) residue at X$_1$. Other types of covalent linkages for cyclization envisioned include peptide linkages, as for example, an amide formed between the side-chain amino group of a lysyl residue with a side-chain carboxyl group of a glutamyl residue and ester linkages, such as would be formed between a side-chain alcohol of a threonine residue with a side-chain carboxyl of an aspartyl residue. Any compatible residue capable of forming peptide bonds with the remainder of the chain (or modified peptide bonds as described above) and capable of covalent bond formation to effect cyclization can be used. This includes, for example, simple cyclic peptides, wherein a peptide bond is directly formed between the NH$_2$ at the N-terminus and the COOH at the C-terminus.

As described above, one or more of the indicated peptide bonds may be replaced by a substitute linkage such as —CH$_2$NH—, —CH$_2$S—, CH$_2$CH$_2$—, —CH═CH— (cis and trans), —COCH$_2$—, —CH(OH)CH$_2$— and —CH$_2$SO—.

In the designation of the amino acid residues AA$_1$–AA$_4$ above, description has been made on the basis of a classification method, wherein amino acid residues can be generally subclassified into four major subclasses. This classification is also shown diagrammatically hereinbelow.

Acidic: The residue has a negative charge due to loss of H ion at physiological pH and the residue is attracted by aqueous solution so as to seek the surface positions in the conformation of a peptide in which it is contained when the peptide is in aqueous medium at physiological pH.

Basic: The residue has a positive charge due to association with H ion at physiological pH and the residue is attracted by aqueous solution so as to seek the surface positions in the conformation of a peptide in which it is contained when the peptide is in aqueous medium at physiological pH.

Neutral/nonpolar: The residues are not charged at physiological pH and the residue is repelled by aqueous solution so as to seek the inner positions in the conformation of a peptide in which it is contained when the peptide is in aqueous medium. These residues are also designated "hydrophobic" herein.

Neutral/polar: The residues are not charged at physiological pH, but the residue is attracted by aqueous solution so as to seek the outer positions in the conformation of a peptide in which it is contained when the peptide is in aqueous medium.

It is understood, of course, that in a statistical collection of individual residue molecules some molecules will be charged, and some not, and there will be an attraction for or repulsion from an aqueous medium to a greater or lesser extent. To fit the definition of "charged", a significant percentage (at least approximately 25%) of the individual molecules are charged at physiological pH. The degree of attraction or repulsion required for classification as polar or nonpolar is arbitrary, and, therefore, amino acids specifically contemplated by the invention have been specifically classified as one or 1034 the other. Most amino acids not specifically named can be classified on the basis of known behavior.

Amino acid residues can be further subclassified as cyclic or noncyclic, and aromatic or nonaromatic, self-explanatory classifications with respect to the side chain substituent groups of the residues, and as small or large. The residue is considered small if it contains a total of 4 carbon atoms or less, inclusive of the carboxyl carbon. Small residues are, of course, always nonaromatic.

For the naturally occurring protein amino acids, subclassification according to the foregoing scheme is as follows (see also the diagram below).

Acidic: Aspartic acid and Glutamic acid;

Basic/noncyclic: Arginine, Lysine;

Basic/cyclic: Histidine;

Neutral/polar/small: Glycine, Serine and Cysteine;

Neutral/polar/large/nonaromatic: Threonine, Asparagine, Glutamine;

Neutral/polar/large/aromatic: Tyrosine;

Neutral/nonpolar/small: Alanine;

Neutral/nonpolar/large/nonaromatic: Valine, Isoleucine, Leucine, Methionine;

Neutral/nonpolar/large/aromatic: Phenylalanine, and Tryptophan.

The gene-encoded amino acid proline, although technically within the group neutral/nonpolar/large/cyclic and nonaromatic, is a special case due to its known effects on the secondary conformation of peptide chains, and is not, therefore, included in this defined group, but is classified separately. $AA_3$ is designated a proline residue or a "modified proline residue." Proline, as is understood, is a five-membered nitrogen heterocycle with a carboxyl group in the 2-position. Modified proline residues are all nitrogen five or six-membered heterocycles with carboxyl groups in the position alpha to the nitrogen; additional heterocyclic atoms may also be included in the ring. Thus, modified proline residues include residues of pipecolic acid (2-carboxypiperidine, abbreviated Pip) and thiazolidine (Thz). Thus, proline or modified proline residues are of the formula

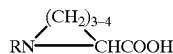

wherein one or two of the methylene groups may be replaced by NR, S, or O and where any ring nitrogen may optionally be substituted with a noninterfering substituent such as alkyl.

Certain commonly encountered amino acids, which are not encoded by the genetic code, include, for example, beta-alanine (beta-ala), or other omega-amino acids, such as 3-amino propionic, 4-amino butyric and so forth, alpha-aminoisobutyric acid (Aib), sarcosine (Sar), ornithine (Orn), citrulline (Cit), homoarginine (Har), t-butylalanine (t-BuA), t-butylglycine (t-BuG), N-methylisoleucine (N-MeIle), phenylglycine (Phg), and cyclohexylalanine (Cha), norleucine (Nle), cysteic acid (Cya); pipecolic acid (Pip), thiazolidine (Thz), 2-naphthyl alanine (2-Nal) and methionine sulfoxide (MSO). These also fall conveniently into particular categories.

Based on the above definition,

Sar and beta-ala are neutral/nonpolar/small;

t-BuA, t-BuG, N-MeIle, Nle and Cha are neutral/nonpolar/large/nonaromatic;

Har and Orn are basic/noncyclic;

Cya is acidic;

Cit, Acetyl Lys, and MSO are neutral/polar/large/nonaromatic;

2-Nal and Phg are neutral/nonpolar/large/aromatic; and

Pip and Thz are modified proline residues.

The foregoing may be shown diagrammatically as follows:

---

Amino Acid Classification Scheme

Acidic: Glu (E), Asp (D); Cysteic (Cya)

Basic: Non-cyclic: Lys (K), Arg (R); Ornithine (Orn); homoarginine (Har)
Cyclic: His (H)

Amino Acid Classification Scheme

```
                        Neutral
                       /       \
                   Polar        Non-Polar
                  /     \       /        \
              Small    Large  Small      Large
                |       |       |        /    \
           Non-aromatic Aromatic Non-aromatic Aromatic
                |       |       |        |      |
           Gly (G)   Thr (T) Tyr (Y)  Ala (A) Val (V)  Phe (F)
           Ser (S)   Asn (N)          Leu (L) Trp (W)
           Cys (C)   Gln (Q)          Ile (I)
           -------   -------          -------  ------
           Cit       Sar              tBuA
           MSO       Beta-ala         tBuG     Phg
           Acetyl Lys Aib             N—MeIle
                                      Nle
                                      Cha
```

The various omega-amino acids are classified according to size as neutral/nonpolar/small (beta-ala, i.e., 3-aminopropionic, 4-aminobutyric) or large (all others).

Other amino acid substitutions for those encoded in the gene can also be included in peptide compounds within the scope of the invention and can be classified within this general scheme.

In the formulas representing selected specific embodiments of the present invention, the amino-and carboxy-terminal groups, although often not specifically shown, will be understood to be in the form they would assume at physiological pH values, unless otherwise specified. Thus, the N-terminal $H^+_2$ and C-terminal-$O^-$ at physiological pH are understood to be present though not necessarily specified and shown, either in specific examples or in generic formulas. Of course, the basic and acid addition salts which are formed at nonphysiological pH values are also included in the compounds of the invention. Unless otherwise noted, the residues are in the L-form; in generic formulas, the specified residues can be either L- or D-. Generally, the peptides of the invention have 0, 1, or 2 D-residues included, preferably 0 or 1, most preferably 0. In the peptides shown, each encoded residue where appropriate is represented by a single letter designation, corresponding to the trivial name of the amino acid, in accordance with the following conventional list:

| Amino Acid | One-Letter Symbol |
|---|---|
| Alanine | A |
| Arginine | R |
| Asparagine | N |
| Aspartic acid | D |
| Cysteine | C |
| Glutamine | Q |
| Glutamic acid | E |
| Glycine | G |
| Histidine | H |
| Isoleucine | I |
| Leucine | L |
| Lysine | K |
| Methionine | M |
| Phenylalanine | F |
| Proline | P |
| Serine | S |
| Threonine | T |
| Tryptophan | W |
| Tyrosine | Y |
| Valine | V |
| Pyroglutamic acid | Z |

The amino acids not encoded genetically are abbreviated as indicated above.

In the specific peptides shown in the present application, the L-form of any amino acid residue having an optical isomer is intended unless otherwise expressly indicated by a dagger superscript (°). While the residues of the invention peptides are normally in the natural L optical isomer form, one or two, preferably one, amino acid may be replaced with the optical isomer D form.

Free functional groups, including those at the carboxy- or amino-terminus, can also be modified by amidation, acylation or other substitution, which can, for example, change the solubility of the compounds without affecting their activity.

In forming amidated peptides of the present invention, the analog compounds can be synthesized directly, for example using Boc-$AA_x$-pMBHA-Resin or Boc-$AA_x$-BHA-Resin, wherein $AA_x$ is the selected carboxy-terminal amino acid of the desired peptide as described in further detail below. Alternatively, the peptides of the present invention can be chemically or enzymatically amidated subsequent to peptide synthesis using means well known to the art, or prepared by standard solution-phase peptide synthesis protocols.

Certain embodiments of the de novo peptides of the invention are preferred. In the K*(G/Sar)D sequence, G/Sar is preferably G. $AA_1$ and $AA_4$ are preferably Gly, Ala or Ser; n1 is preferably 0–2, n4 is preferably 1–2. Preferred for $AA_2$ are neutral/nonpolar/aromatic amino acids, especially tryptophan and phenylalanine, particularly tryptophan, $n_2$ is preferably 1. $X_1$ and $X_2$ are preferably Cys, Mpr, or Pen (penicillamine) residues. $Y_1$ is preferably H, acetyl, or Gly; $Y_2$ is preferably —$NH_2$ or —A—$NH_2$. Also preferred generally are C-terminal amidated forms of $Y_2$.

Thus, preferred embodiments of the PAI analogs of the invention include peptides of the following formulas. Although all of these may be in cyclic form through formation of disulfide linkages, these linkages are not shown; other cyclic forms are noted by "cyclo."

Preferred Peptides

PAI 1: E-C-A-D-G-L-C-C-D-Q-C-R-F-L-K-K-G-T-V-C-R-V-A-K-G-D-W-N-D-D-T-C-T-G-Q-S-C-D-C-P-R-N-G-L-Y-G

PAI 2: E-E-P-C-A-T-G-P-C-C-R-R-C-K-F-K-R-A-G-K-V-C-R-V-A-K-G-D-W-N-N-D-Y-C-T-G-K-S-C-D-C-P-R-N-P-W-N-G

PAI 3: G-C-G-K-G-D-W-P-C-A-$NH_2$;

PAI 4: G-C-K-G-D-W-P-C-A-$NH_2$

PAI 5: C-G-K-G-D-W-P-C-$NH_2$

PAI 7: C-K-G-D-W-C-A-$NH_2$;

PAI 9: Mpr-K-G-D-Pen-$NH_2$

PAI 10: C-K-G-D-W-P-C-$NH_2$

PAI 12: C-K-G-D-Y-P-C-$NH_2$

PAI 13: C-K-G-D-F-P-C-$NH_2$

PAI 14: C-K-G-D-L-P-C-$NH_2$

PAI 15: C-K-G-D-V-P-C-NH$_2$
PAI 16: C-K-G-D-Y(OMe)-P-C-NH$_2$
PAI 17: C-K-G-D-(2-Nal)-P-C-NH$_2$
PAI 16: C-K-G-D-(Cha)-P-C-NH$_2$
PAI 19: Mpr-K-G-D-W-P-C-NH$_2$
PAI 20: Mpr-K-G-D-Y-P-C-NH$_2$
PAI 21: Mpr-K-G-D-F-P-C-NH$_2$
PAI 22: Mpr-K-G-D-L-P-C-NH$_2$
PAI 23: Mpr-K-G-D-V-P-C-NH$_2$
PAI 24: Mpr-K-G-D-Y(OMe)-P-C-NH$_2$
PAI 25: Mpr-K-G-D-(2-Nal)-P-C-NH$_2$
PAI 26: Mpr-K-G-D-(Cha)-P-C-NH$_2$
PAI 27: cyclo(G-K-G-D-W-P)
PAI 28: cyclo(A-K-G-D-W-P)
PAI 29: cyclo(D-Ala-K-G-D-W-P)
PAI 30: cyclo(F-K-G-D-W-P)
PAI 31: cyclo(beta-Ala-K-G-D-W-P)
PAI 32: cyclo(gamma-Abu-K-G-D-W-P)
PAI 33: cyclo(R-K-G-D-W-P)
PAI 34: C-K-G-D-W-G-C-NH$_2$
PAI 37: C-K-A-D-W-P-C-NH$_2$
PAI 39: C-K-G-D-W-(Sar)-C-NH$_2$
PAI 41: C-K-G-D-I-P-C-NH$_2$
PAI 42: C-K-G-D-(4-Cl-Phe)-P-NH$_2$
PAI 43: C-K-(Sar)-D-W-P-C-NH$_2$
PAI 44: C-K-G-D-(4-NO$_2$-Phe)-P-C-NH$_2$
PAI 47: Acetyl-C-K-G-D-W-P-C-NH$_2$
PAI 48: Mpr-K-G-D-W(Formyl)-P-C-NH$_2$
PAI 49: Mvl-K-G-D-W-P-C-NH$_2$
PAI 51: Mpr-K-G-D-W-P-Pen-NH$_2$
PAI 52: Mpr-K-G-D-W-P-Pen°-NH$_2$
PAI 54: Mpr-K-G-D°-W-P-Pen-NH$_2$
PAI 55: Mpr-K-G-D-W-(Thz)-C-NH$_2$
PAI 56: Mpr-K-G-D-H(2,4-DNP)-P-C-NH$_2$
PAI 57: Mpr-K-G-D-(2-Nal)-P-Pen-NH$_2$
PAI 58: Mvl-K-G-D-W-P-Pen-NH$_2$
PAI 59: Mpr-K-G-D-W-(Pip)-Pen-NH$_2$
PAI 60: Mpr-(Har)-G-D-W-P-C-NH$_2$
PAI 61: Mpr-K-G-D-W-P-C°-NH$_2$
PAI 62: Mpr-K°-G-D-W-P-Pen-NH$_2$
PAI 63: Mpr-(Har)-G-D-W-P-Pen-NH$_2$
PAI 64: Mpr-(Acetimidyl-Lys)-G-D-W-P-C-NH$_2$
PAI 65: Mpr-(Acetimidyl-Lys)-G-D-W-P-Pen-NH$_2$
PAI 66: Mpr-(N$^G$, N$^{G'}$-ethylene-Har)-G-D-W-P-C-NH$_2$
PAI 67: Mpr-(N$^G$, N$^{G'}$-ethylene-Har)-G-D-W-P-Pen-NH$_2$
PAI 68: Mpr-Har-Sar-D-W-P-C-NH$_2$
PAI 69: Mpr-(Acetimidyl-Lys)-G-D-W-P-Pen-NH$_2$
PAI 70: Mpr-(Phenylimidyl-Lys)-G-D-W-P-C-NH$_2$
Particularly preferred are peptides of the formulas
PAI 3: G-C-G-K-G-D-W-P-C-A-NH$_2$;
PAI 4: G-C-K-G-D-W-P-C-A-NH$_2$;
PAI 5: C-G-K-G-D-W-P-C-NH$_2$;
PAI 9: Mpr-K-G-D-Pen-NH$_2$; and
PAI 10: C-K-G-D-W-P-C-NH$_2$
PAI 12: C-K-G-D-Y-P-C-NH$_2$
PAI 13: C-K-G-D-F-D-C-NH$_2$
PAI 19: Mpr-K-G-D-W-P-C-NH$_2$ PAI 25: Mpr-K-G-D-(2-Nal)-P-C-NH$_2$
PAI 34: C-K-G-D-W-G-C-NH$_2$
PAI 39: C-K-G-D-W-(Sar)-C-NH$_2$
PAI 42: C-K-G-D-(4-Cl-Phe)-P-NH$_2$
PAI 43: C-K-(Sar)-D-W-P-C-NH$_2$
PAI 44: C-K-G-D-(4-NO$_2$-Phe)-P-C-NH$_2$
PAI 47: Acetyl-C-K-G-D-W-P-C-NH$_2$
PAI 48: Mpr-K-G-D-W(Formyl)-P-C-NH$_2$
PAI 49: Mvl-K-G-D-W-P-C-NH$_2$
PAI 51: Mpr-K-G-D-W-P-Pen-NH$_2$
PAI 52: Mpr-K-G-D-W-P-(D-Pen)-NH$_2$
PAI 55: Mpr-K-G-D-W-(Thz)-C-NH$_2$
PAI 56: Mpr-K-G-D-H(2,4-DNP)-P-C-NH$_2$
PAI 57: Mpr-K-G-D-(2-Nal)-P-Pen-NH$_2$
PAI 58: Mvl-K-G-D-W-P-Pen-NH$_2$
PAI 59: Mpr-K-G-D-W-(Pip)-Pen-NH$_2$
PAI 60: Mpr-(Har)-G-D-W-P-C-NH$_2$
PAI 61: Mpr-K-G-D-W-P-C°-NH$_2$
PAI 62: Mpr-K°-G-D-W-P-Pen-NH$_2$
PAI 63: Mpr-(Har)-G-D-W-P-Pen-NH$_2$
PAI 64: Mpr-(Acetimidyl-Lys)-G-D-W-P-C-NH$_2$
PAI 65: Mpr-(Acetimidyl-Lys)-G-D-W-P-Pen-NH$_2$
PAI 66: Mpr (N$^G$, N$^{G'}$-ethylene-Har)-G-D-W-P-C-NH$_2$
PAI 67: Mpr (N$^G$, N$^{G'}$-ethylene-Har)-G-D-W-P-Pen-NH$_2$
PAI 68: Mpr-Har-Sar-D-W-P-C-NH$_2$
PAI 69: Mpr-(Acetimidyl-Lys)-G-D-W-P-Pen-NH$_2$
PAI 70: Mpr-(Phenylimidyl-Lys)-G-D-W-P-C-NH$_2$ Chemical Synthesis of the Invention Peptides Compounds within the scope of the present invention can be synthesized chemically by means well known in the art such as, e.g., solid-phase peptide synthesis. The synthesis is commenced from the carboxy-terminal end of the peptide using an alpha-amino protected amino acid. t-Butyloxycarbonyl (Boc) protective groups can be used for all amino groups even though other protective groups such as fluorenylmethyloxycarbonyl (Fmoc), are suitable. For example, Boc-Gly-OH, Boc-Ala-OH, Boc-His (Tos)-OH, (i.e., selected carboxy-terminal amino acids) can be esterified to chloromethylated polystyrene resin supports, p-methyl benzhydrylamine (pMBHA) or PAM resins. The polystyrene resin support is preferably a copolymer of styrene with about 0.5 to 2% divinyl benzene as a cross-linking agent which causes the polystyrene polymer to be completely insoluble in certain organic solvents. See Stewart, et al., *Solid-Phase Peptide Synthesis* (1969) W. H. Freeman Co., San Francisco and Merrifield, *J Am Chem Soc* (1963) 85:2149–2154. These and other methods of peptide synthesis are also exemplified by U.S. Pat. Nos. 3,862,925, 3,842,067, 3,972,859, and 4,105,602.

The synthesis may use manual synthesis techniques or automatically employ, for example, an Applied BioSystems 430A or 431A Peptide Synthesizer (Foster City, Calif.) following the instructions provided in the instruction manual supplied by the manufacturer. Cleavage of the peptides from the resin can be performed using the "low-high" HF deprotection protocols as described in Lu, G.-S., et al., *Int J Peptide & Protein Res* (1987) 29:545–557. Refolding of analogs of the snake venom PAIs can be performed using the procedure outlined in Garsky, V., et al., *Proc Natl Acad Sci USA* (1989) 86:4022–4026 which describes the solid-phase synthesis of echistatin.

The cyclic peptides of this invention which do not have disulfide bonds can be conveniently prepared by a combination of solid phase synthesis and formation of the cyclic ring structure in solution using the general methods as outlined in U.S. Pat. No. 4,612,366 to Nutt. Thus, linear peptides prepared on standard Merrifield resin can be cleaved from the resin with hydrazine, followed by cyclization of the corresponding azide to form the cyclic peptides.

It will be readily appreciated by those having ordinary skill in the art of peptide synthesis that the intermediates which are constructed in accordance with the present disclosure during the course of synthesizing the present analog compounds are themselves novel and useful compounds and are thus within the scope of the invention.

Recombinant Production

Alternatively, selected compounds of the present invention can be produced by expression of recombinant DNA constructs prepared in accordance with well-known methods. Such production can be desirable to provide large quantities or alternative embodiments of such compounds. Since the peptide sequences are relatively short, recombinant production is facilitated.

The DNA encoding the sequenced PAI is preferably prepared using commercially available nucleic acid synthesis methods. Methods to construct expression systems for production of PAI in recombinant hosts are also generally known in the art.

Expression can be effected in either procaryotic or eucaryotic hosts. Procaryotes most frequently are represented by various strains of E. coli. However, other microbial strains may also be used, such as bacilli, for example *Bacillus subtilis*, various species of Pseudomonas, or other bacterial strains. In such procaryotic systems, plasmid vectors which contain replication sites and control sequences derived from a species compatible with the host are used. For example, a workhorse vector for *E. coli* is pBR322 and its derivatives. Commonly used procaryotic control sequences, which contain promoters for transcription initiation, optionally with an operator, along with ribosome binding-site sequences, include such commonly used promoters as the beta-lactamase (penicillinase) and lactose (lac) promoter systems, the tryptophan (trp) promoter system, and the lambda-derived $P_L$ promoter and N-gene ribosome binding site. However, any available promoter system compatible with procaryotes can be used.

Expression systems useful in eucaryotic hosts comprise promoters derived from appropriate eucaryotic genes. A class of promoters useful in yeast, for example, includes promoters for synthesis of glycolytic enzymes, e.g., those for 3-phosphoglycerate kinase. Other yeast promoters include those from the enolase gene or the Leu2 gene obtained from YEp13.

Suitable mammalian promoters include the early and late promoters from SV40 or other viral promoters such as those derived from polyoma, adenovirus II, bovine papilloma virus or avian sarcoma viruses. Suitable viral and mammalian enhancers are cited above. In the event plant cells are used as an expression system, the nopaline synthesis promoter, for example, is appropriate.

The expression systems are constructed using well-known restriction and ligation techniques and transformed into appropriate hosts.

Transformation is done using standard techniques appropriate to such cells. The cells containing the expression systems are cultured under conditions appropriate for production of the PAI, and the PAI is then recovered and purified.

Antibodies

The availability of the purified PAI of the invention also permits the production of antibodies specifically immunoreactive with these forms of the active peptide.

The compositions containing purified PAI isolated from snake venom or otherwise synthesized can be used to stimulate the production of antibodies which immunoreact with the PAI peptide. Standard immunization protocols involving administering PAI to various vertebrates, such as rabbits, rats, mice, sheep, and chickens result in antisera which are immunoreactive with the purified peptide. PAI may be advantageously conjugated to a suitable antigenically neutral carrier, such as an appropriate serum albumin or keyhole limpet hemocyanin, in order to enhance immunogenicity. In addition, the free peptide can be injected with methylated BSA as an alternative to conjugation. Furthermore, the antibody-secreting cells of the immunized mammal can be immortalized to generate monoclonal antibody panels which can then be screened for reactivity with PAI.

The resulting polyclonal or monoclonal antibody preparations are useful in assays for levels of the corresponding PAI in biological samples using standard immunoassay procedures.

The Invention Assay

The identification of snake venom starting material which contains active PAI, and which PAI has known specificity, is made possible by the assay of the invention. The assay rests on the observation that compounds which block the binding of fibrinogen to the GP IIb–IIIa complex in vitro also are capable of inhibiting thrombin or ADP-induced aggregation of human platelets and the formation of platelet-thrombi in vivo. This observation provides the basis for obtaining potent PAI by evaluating the ability of test materials to disrupt fibrinogen-GP IIb–IIIa interactions.

In the assay, GP IIb–IIIa, prepared in purified form, for example as described by Fitzgerald, L. A., et al., *Anal Biochem* (1985) 151:169–177, incorporated herein by reference, is coated onto a solid support such as beads, test tubes, or microtiter plates. The coated support is then contacted with fibrinogen and with the test material and incubated for a sufficient time to permit maximal binding of fibrinogen to the immobilized GP IIb–IIIa. Fibrinogen is typically provided at a concentration of about 5–50 nM and the test material can, if desired, be added at a series of dilutions. Typical incubations are 2–4 hr at 35° C., the time and temperature being interdependent.

After incubation, the solution containing the fibrinogen and test material is removed and the level of binding of fibrinogen measured by quantitating bound fibrinogen to GP IIb–IIha. Any suitable means of detection may be used, but it is convenient to employ labeled fibrinogen, for example using radioactive, fluorescent or biotinylated labels. Such methods are well known and need not be elaborated here.

Assessment of the results is aided by employing a control sample, usually identical to the test sample except that the test substance is absent. In this case, percent inhibition may be calculated using the amount of Fg bound in the control as representing the basis, so that $$\% \text{ inhibition} = \frac{\text{control} - \text{test}}{\text{control}} \times 100.$$

Other measures of inhibition effectiveness, such as $IC_{50}$, may also be used.

The assay systems of the invention further include characterization of the PAI specificity by binding inhibition assays identical to that above but substituting other adhesive proteins for Fg and other receptors for GP IIb–IIIa. In particular, inhibition of the binding of vitronectin to the vitronectin receptor; fibronectin to the fibronectin receptor; fibronectin to GP IIb–IIIa and fibrinogen and/or vWF to GP IIb–IIIa may be assessed. The adhesive protein and receptors for these assays are available in the art.

Other Assays

In addition to the plate assays of the invention, other assays for platelet aggregation inhibition activity and related activities are also available, as set forth above. In summary, a list of commonly employed assays is as follows:

1. The plate assays utilizing specific receptors described in the previous paragraphs;
2. Standard assays directly applied to platelet aggregation, such as those described by Gann, Z.-R., et al., *J Biol Chem* (1988) 263:19827–19832; Huang, T. F., et al., *J Biol Chem* (1987) 262:16157–16163; *Biochemistry* (1989) 28:661–666, cited above and incorporated herein by reference;
3. An in vivo thrombosis model in dogs as described hereinbelow in Example 1, and by Folts, J. D., et al., *Circulation* (1976) 54:365; and
4. Effect on cell adhesion using S35 methionine-labeled cells as described hereinbelow in Example 19.

Administration and Utility

The PAIs of the invention are useful therapeutically to prevent thrombus formation. Indications appropriate to such treatment include, without limitation, atherosclerosis and arteriosclerosis, acute myocardial infarction, chronic unstable angina, transient ischemic attacks and strokes, peripheral vascular disease, arterial thrombosis, preeclampsia, embolism, restenosis and/or thrombosis following angioplasty, carotid endarterectomy, anastomosis of vascular grafts, and chronic cardiovascular devices (e.g., in-dwelling catheters or shunts "extracorporeal circulating devices"). These syndromes represent a variety of stenotic and occlusive vascular disorders thought to be initiated by platelet activation on vessel walls.

The PAIs may be used for prevention or abortion of arterial thrombus formation, in unstable angina and arterial emboli or thrombosis, as well as treatment or prevention of myocardial infarction (MI) and mural thrombus formation post MI. For brain-related disorders, treatment or prevention of transient ischemic attack and treatment of thrombotic stroke or stroke-in-evolution are included.

The PAIs may also be used for prevention of platelet aggregation, embolization, or consumption in extracorporeal circulations, including improving renal dialysis, cardiopulmonary bypasses, hemoperfusions, and plasmapheresis.

PAIs prevent platelet aggregation, embolization, or consumption associated with intravascular devices, and administration results in improved utility of intraaortic balloon pumps, ventricular assist devices, and arterial catheters.

The PAIs will also be useful in treatment or prevention of venous thrombosis as in deep venous thrombosis, IVC, renal vein or portal vein thrombosis, and pulmonary venous thrombosis.

Various disorders involving platelet consumption, such as thrombotic thrombocytopenic purpura are also treatable.

In addition, the PAIs of the present invention may be used in numerous nontherapeutic applications where inhibiting platelet aggregation is desired. For example, improved platelet and whole blood storage can be obtained by adding sufficient quantities of the peptides, the amount of which will vary depending upon the length of proposed storage time, the conditions of storage, the ultimate use of the stored material, etc.

The PAI dosage can range broadly depending upon the desired affects and the therapeutic setting. Typically, dosages will be between about 0.01 and 10 mg/kg, preferably between about 0.01 to 0.1 mg/kg, body weight. Administration is preferably parenteral, such as intravenous on a daily basis for up to a week or as much as one or two months or more, all of which will vary with the peptide's size. If the peptides are sufficiently small (e.g., less than about 8–10 amino acid residues) other routes of administration can be utilized, such as intranasally, sublingually, or the like.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride or the like. In addition, if desired, the injectable pharmaceutical compositions may contain minor amounts of nontoxic auxiliary substances, such as wetting agents, pH buffering agents, and the like. If desired, absorption enhancing preparations (e.g., lutisomes) may be utilized.

EXAMPLE 1

Assay for Snake Venom Platelet Adhesion Inhibitors

A. Description of Assays—Plate Assays

Purified platelet GP IIb–IIIa receptor was prepared as described by Fitzgerald, L. A., et al., *Anal Biochem* (1985) 151:169–177. Vitronectin receptor was prepared as described by Smith, J. W., *J Biol Chem* (1988) 263:18726–18731. After purification, the receptors were stored in 0.1% Triton X-100 at 0.1–1.0 mg/ml.

The receptors were coated to the wells of 96-well flat-bottom ELISA plates (Linbro EIA-Plus microtiter plate, Flow Laboratories) after diluting 1:200 with a solution of 20 mM Tris-HCl, 150 mM NaCl, 1 mM $CaCl_2$, pH 7.4, to reduce the Triton X-100 concentration to below its critical micellar concentration and adding an aliquot of 100 ul to each well. The wells were all allowed to incubate overnight at 4° C., and then aspirated to dryness. Additional sites were blocked by the addition of bovine serum albumin (BSA) at 35 mg/ml in the above buffer for 2 hr at 30° C. to prevent nonspecific binding. The wells were then washed once with binding buffer (50 nM Tris-HCl, 100 mM NaCl, 2 mM $CaCl_2$, 1 mg/ml BSA).

The corresponding ligands (fibrinogen, von Willebrand Factor, or vitronectin) were labeled with $^{125}I$ or conjugated to biotin using commercially available reagents and standard protocols. The labeled ligands were added to the receptor-coated wells at final concentration of 10 nM (100 ul/well) and incubated for 3 h at 30° C. in the presence or absence of the test samples. After incubation, the wells are aspirated to dryness and bound ligand is quantitated.

For $^{125}I$-labeled ligands, the protein is solubilized with 250 ul SDS. For biotinylated ligands, the bound protein is detected by the addition of antibiotin antibody conjugated to alkaline phosphatase followed by addition of substrate (p-nitrophenyl phosphate), and determination of the optical density of each well at 405 nm. Decreased color development or decreased $^{125}I$ content is observed in wells incubated with test samples which inhibit binding of ligand to receptor.

B. Determination of Adhesion Inhibition in Crude Venom

Sixty-eight crude, lyophilized snake venoms obtained from either Sigma Chemical Company (St. Louis, Mo.) or Miami Serpentarium Labs (Salt Lake City, Utah) were dissolved at 1 mg/ml in buffer (50 mM Tris, 100 mM NaCl, 0.02% azide, 2 mM $CaCl_2$). One ml aliquots of the solutions were subjected to ultrafiltration through Centrocon-10 (YM membrane) microconcentrators (Amicon, Danvers, Mass.). The filtrates were used as test samples in the receptor/ligand assay of paragraph A using the GP IIb–IIIa/fibrinogen system, and detecting binding using biotinylated fibrinogen. The results are shown in Table 1.

It is seen that the activity is present in some, but not all, species of Viperinae, but absent in all species tested of Elapidae.

Figure 1:
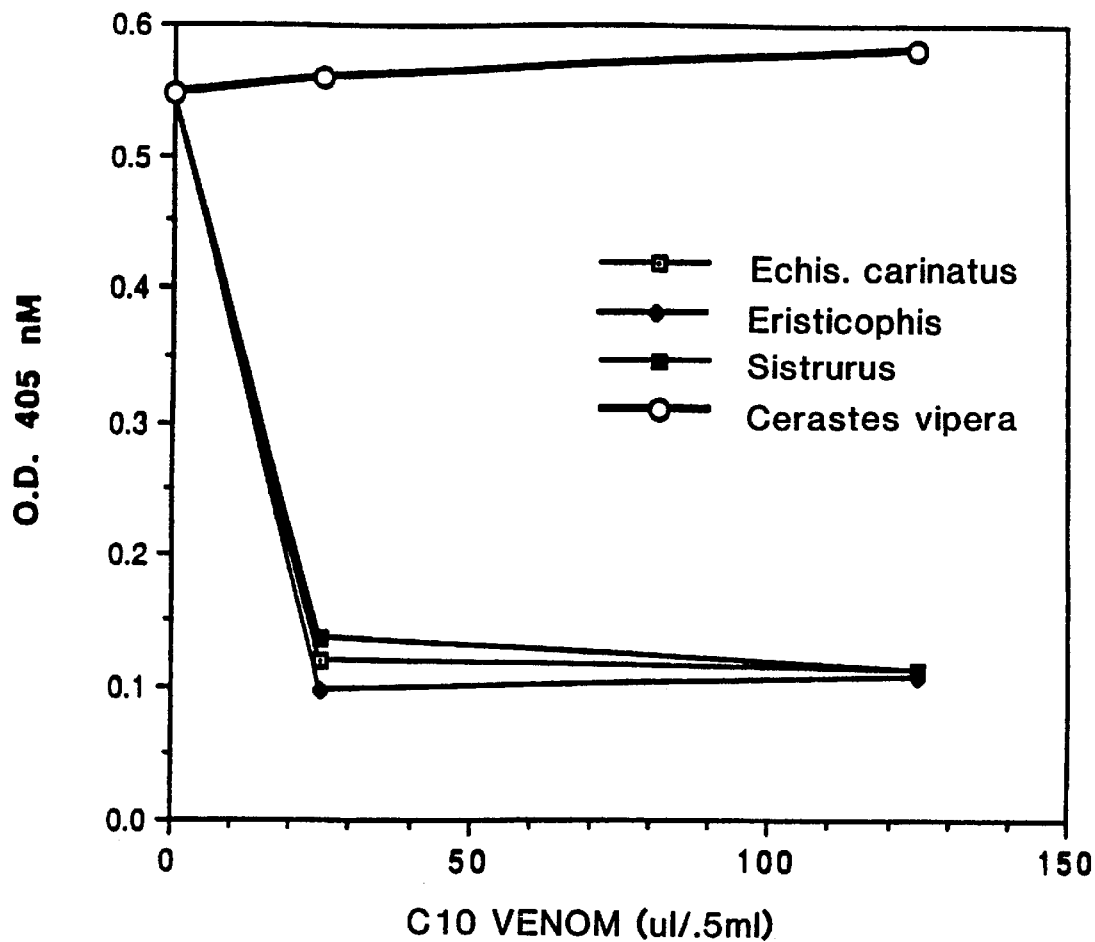

FIG. 1 shows the results at various dilutions of the filtrate for four species. Even at the greatest dilution, 25 ul/0.5 ml, the three active venoms showed maximal inhibition.

C. Determination of the Activity of Peptides in an in vivo Model of Thrombosis

Purified peptides were tested for their ability to prevent thrombi formation in dog coronary arteries in the model described by Folts (Folts J. D., et al., *Circulation* (1976) 54:365. In this model, flow reductions in a constricted coronary artery have been shown to be due to the formation of platelet aggregates, and agents which block the binding of fibrinogen to GP IIb–IIIa have been shown to prevent these flow reductions (Coller, B. S., et al., *Blood* (1986) 68:783. The peptides were dissolved in normal saline and administered into a peripheral vein as a single bolus.

TABLE 1

CENTRICON 10 PURIFIED VENOMS SCREENED IN IIb–IIIa PLATE ASSAY

| | Activity |
|---|---|
| Elapids | |
| *Austrelaps superba* (Australian Copperhead) | – |
| *Acanthopis antarcticus* (Death Adder) | – |
| *Dendroaspis jamesonii* (Jameson's Mamba) | – |
| *Notechis scutatus* (Mainland Tiger) | – |
| *Pseudechis colleti guttatus* (Blue-bellied) | – |
| *Pseudechis textillis textillis* (Common Brown) | – |
| *Oxyuranus scutellatus* (Papuan Taipan) | – |
| Viperinae (True Vipers) | |
| *Atheris squamigera* (Green Bush Viper) | – |
| *Bitis nasicornus* (River Jack) | – |
| *Causus rhombeatus* (Rhombic Night Adder) | – |
| *Cerastes cerastes* (Desert Horned Viper) | – |
| *Cerastes vipera* (Sahara Horned Viper) | – |
| *Echis carinatus* (Saw-scaled Viper) | + |
| *Echis colorata* (Carpet Viper) | + |
| *Eristicophis macmahonii* (Macmahons Viper) | ++ |
| *Pseudocerastes fieldi* (Persian Horned Viper) | – |
| *Vipera xanthina xanthina* (Ottomans Viper) | – |
| *Vipera ammodytes* (Long-nosed Viper) | – |
| *Vipera r. russelli* (Russells Viper) | – |
| *Vipera r. siamensis* | – |
| *Vipera palaestinae* (Palestine Viper) | – |
| Crotalinae (Pit Vipers) | |
| *Agkistrodon rhodostoma* (Malayan Pit Viper) | + |
| *Agkistrodon halys blomhoffi* (Mamushi) | + |
| *Agkistrodon hypnale* (Hump-nosed Viper) | + |
| *Agkistrodon acutus* (Sharp-nosed Viper) | ++ |
| *Agkistrodon bilineatus* (Mexican Moccasin) | – |
| *Agkistrodon contortrix contortrix* | – |
| *Agkistrodon c. laticinctus* | – |
| *Agkistrodon c. pictigaster* | – |
| *Agkistrodon contortrix mokasen* (Northern Copperhead) | – |
| *Agkistrodon piscivorous piscivorous* (Eastern Cottonmouth) | – |
| *Agkistrodon piscivorus leucostoma* (Western Cottonmouth) | + |
| *Agkistrodon piscivorous conanti* | + |
| *Bothrops asper* | + |
| *Bothrops nummifer* (Jumping Viper) | – |
| *Bothrops cotiara* (Cotiara) | + |

TABLE 1-continued

CENTRICON 10 PURIFIED VENOMS SCREENED IN IIb–IIIa PLATE ASSAY

| | Activity |
|---|---|
| *Bothrops jararacussu* (Jararacussu) | + |
| *Bothrops jararaca* (Jararaca) | + |
| *Bothrops lansbergi* | + |
| *Bothrops alternata* (Urutu) | – |
| *Bothrops medusa* | + |
| *Bothrops neuwiedi* | + |
| *Bothrops nasuta* | + |
| *Bothrops pradoi* | + |
| *Bothrops schlegli* (Schlegels Viper) | – |
| *Trimeresurus gramineus* (Formosan Green Habu) | – |
| *Trimeresurus flavoviridis* (Okinawa Habu) | – |
| *Trimeresurus wagleri* | – |
| *Lachesis mutas* (Bushmaster) | – |
| *Crotalus durrisus terrificus* (Tropical Rattlesnake) | – |
| *Crotalus durissus totonatacus* | – |
| *Crotalus durissus durissus* | – |
| *Crotalus scutalatus* (Mojave rattlesnake) | – |
| *Cortalus horridus horridus* (Timber Rattlesnake) | – |
| *Crotalus horridus atricaudatus* (Canebrake RS) | – |
| *Crotalus atrox* (Western Diamondback) | – |
| *Crotalus adamanteus* (Eastern Diamondback) | – |
| *Crotalus basilicus* (Mexican West-coast RS) | – |
| *Crotalus molossus molossus* (Black-tailed RS) | – |
| *Crotalus ruber ruber* (Red diamondback RS) | – |
| *Crotalus cerastes cerastes* (Mojave sidewinder) | – |
| *Crotalus viridis viridis* (Prairie Rattlesnake) | + |
| *Crotalus v. helleri* (Southern pacific RS) | + |
| *Crotalus v. oreganus* (Northern pacific RS) | + |
| *Crotalus v. cereberus* (Arizona black RS) | + |
| *Crotalus v. lutosus* (Great Basin RS) | + |
| *Crotalus v. concolor* (Midget-faded RS) | – |
| *Sistrurus catenatus tergeminus* (Western massasauga) | + |
| *Sistrurus milarius barbouri* (Southeastern Pigmy Rattlesnake) | + |

D. Effects of Purified Snake Venom Peptides on Cell Attachment to Adhesive Proteins M21 melanoma cells, which express high levels of the vitronectin receptor, were metabolically labelled with $^{35}$S-methionine, and then added to 24-well tissue culture plates coated with vitronectin. An incubation period of 1 hr at 37° C. was allowed for cell attachment, and this was followed by a wash to remove non-adherent cells. After washing, the adherent cells were solubilized, and the supernatants placed in a liquid scintillation counter. The fraction of cells remaining adherent was calculated by dividing the cpm in the solubilized supernatants by the cpm in the total-number of cells added to each well. The effects of purifed snake venom peptides and synthetic cyclic peptides on cell adhesion was determined by including them with the M21 cells during the incubation period.

E. Specificity of Adhesion Inhibition

Figure 2A:
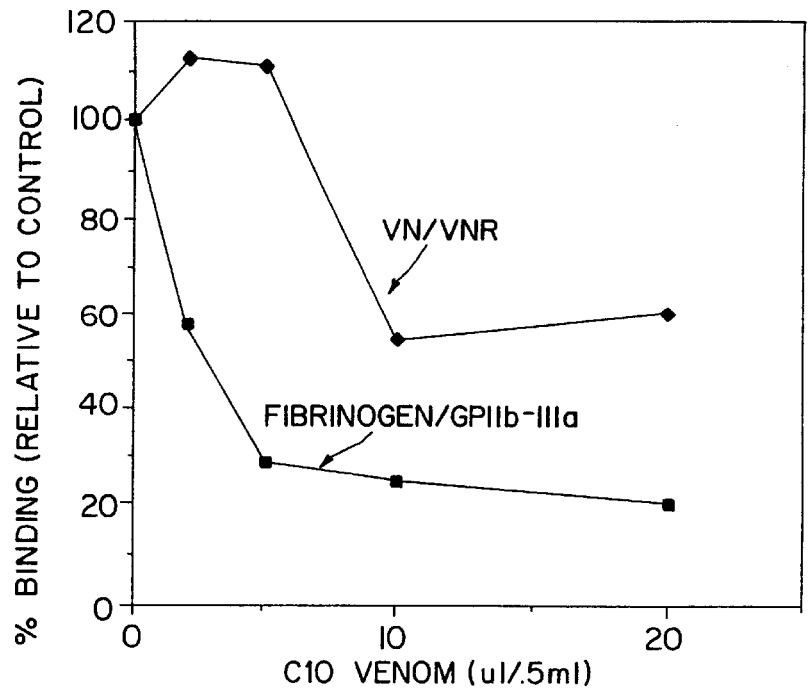
Figure 2B:
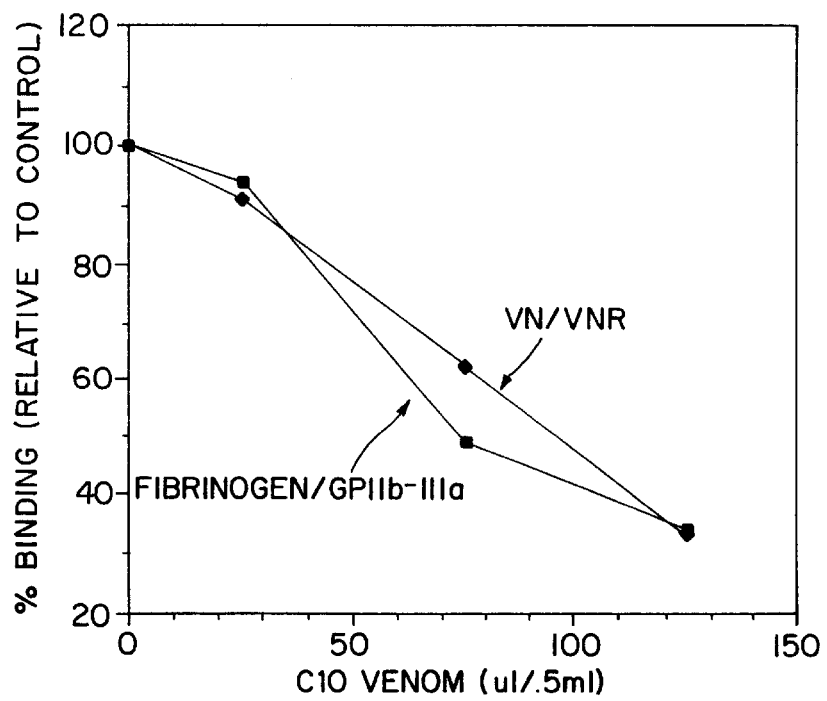
Figure 2C:
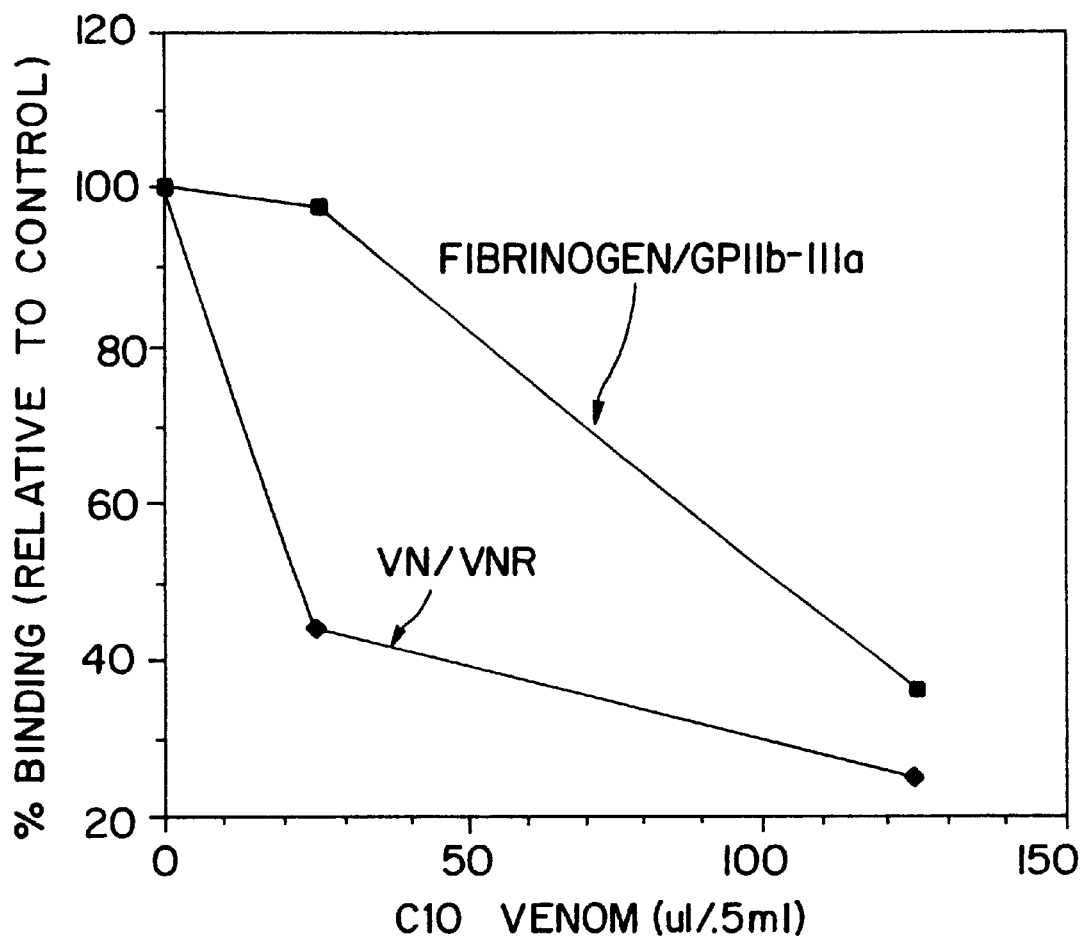

Ultrafiltrates from three species of snake venom, *Sistrurus m. barbouri, Crotalus ruber ruber*, and *Crotalus basilicus*, were tested in both the fibrinogen/GP IIb–IIIa and vitronectin/vitronectin receptor assays of paragraph A. The results were evaluated at various dilutions. As shown in FIG. 2A, the venom from *Sistrurus m. barbouri* preferentially inhibits the binding of fibrinogen to GP IIb–IIIa; as shown in FIG. 2B the venom of *Crotalus ruber ruber* inhibits binding in both systems approximately equally; and as shown in FIG. 2C the venom from *Crotalus basilicus* preferentially inhibits vitronectin/vitronectin receptor binding.

In the purifications described in Examples 2–6 and 8–12, PAI activity was assayed using a direct inhibition of platelet aggregation. Platelet rich plasma (PRP) was obtained from a healthy human volunteer. Aggregation was induced by the addition of 4 uM ADP to 0.5 ml PRP in an aggregometer (Chrono-log Corp.).

A table showing results of amino acid composition analysis of purified PAIs of Examples 2–6 will be found after Example 6; that showing the results for Examples 8–11 is shown after Example 8.

This analysis was obtained by hydrolysis of peptides using 6N HCl and analyzing the hydrolysate using a Beckman 121 HC analyzer equipped with a Model 126 data system. Cysteic acid was determined according to the method of Moore, *J Biol Chem* (1969) 230:235–237. Tryptophan was not determined.

EXAMPLE 2

Purification of Platelet Aggregation Inhibitor (PAI) From *Eristocophis macmahoni* Venom A solution of 45 mg of *Eristocophis macmahoni* venom (Miami Serpentarium Labs, Lot #EM23SZ) in 1.0 ml of 0.5% trifluoroacetic acid (TFA) was cooled on ice for 20 min, spun at 14,000 rpm for 3 min to remove insoluble material and loaded onto a 3.9 mm ×30 cm, C-18 Delta Pak reverse-phase HPLC column (Waters, Milford, Mass.) equilibrated with 5% acetonitrile containing 1% TFA. A gradient running from 5% to 15% acetonitrile over 5 min (2%/min) followed by a gradient from 15% to 30% acetonitrile over 35 min and then to 50% acetonitrile over 20 min, was run using a Waters 600E liquid chromatograph. A flow rate of 1.5 ml/min was maintained throughout the gradient and column effluent was collected in 2 min fractions into polypropylene tubes.

The column effluent was monitored at 220 nm/2.5 absorbance units full scale (AUFS).

Fractions were concentrated to one-half their original volume using a Speed-Vac concentrator (Savant) followed by lyophilization. Samples were then reconstituted constituted in 1 ml distilled water and aliquots (10–50 ul) assayed for their ability to inhibit human platelet aggregation in platelet-rich plasma induced by 20 uM ADP using a whole blood aggregometer (Chrono-Log Corp., Havertown, Pa.).

Figure 3:
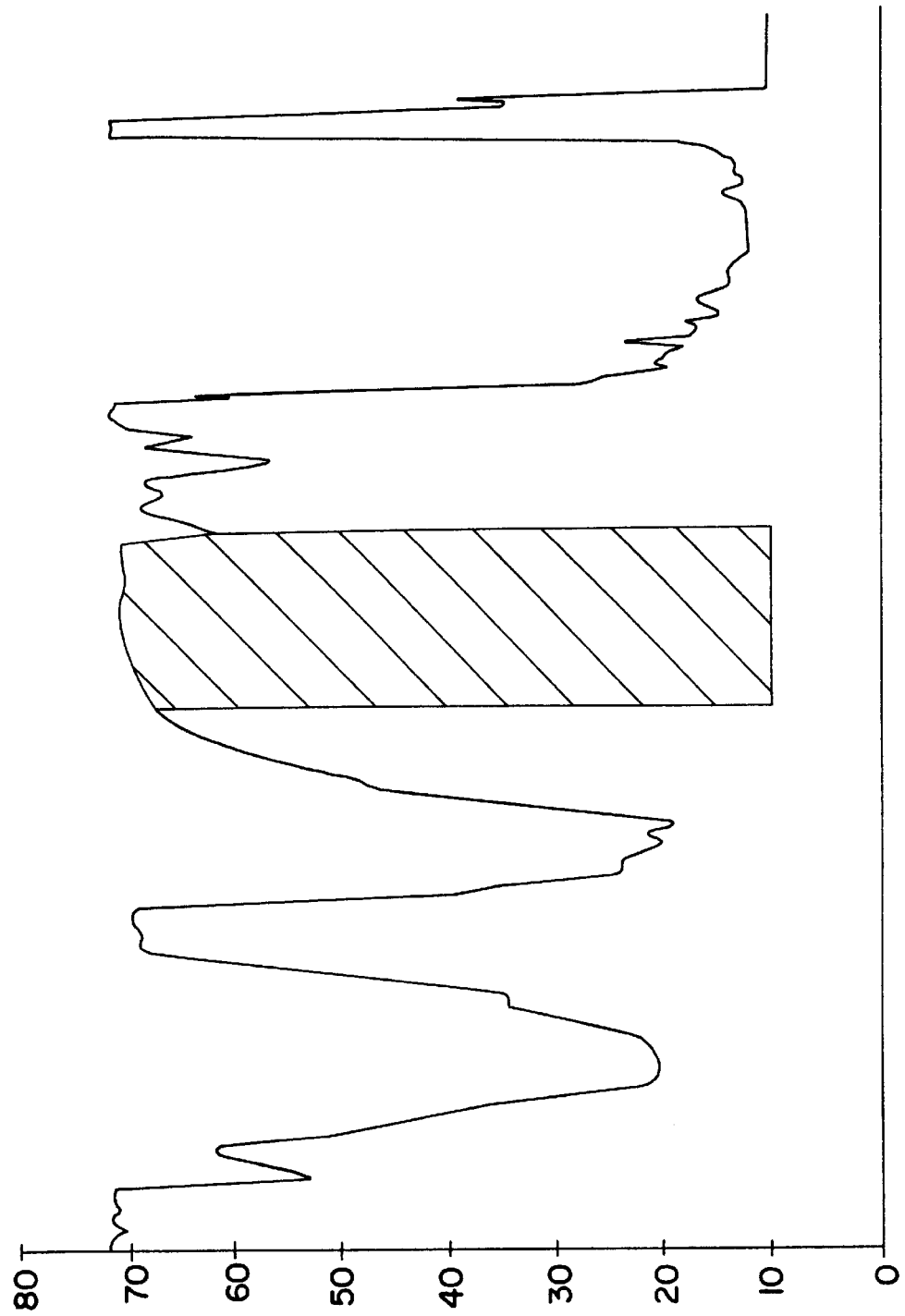
FIG. 3 shows the HPLC profile of crude PAI from Eristicophis macmahoni venom. The cross-hatched area contains the biologically active fractions.

As shown in FIG. 3, activity was found in fractions that eluted at 21–25% acetonitrile concentration. These fractions were then lyophilized and rerun on the C-18 HPLC column using shallower acetonitrile gradient as follows: Initial conditions consisted of 8% acetonitrile followed by a gradient to 25% acetonitrile over 68 min (0.25%/min), then to 60% acetonitrile in 10 min. One-minute fractions were collected, dried and reassayed for inhibitory activity in platelet aggregation of human platelets as above.

Figure 4:
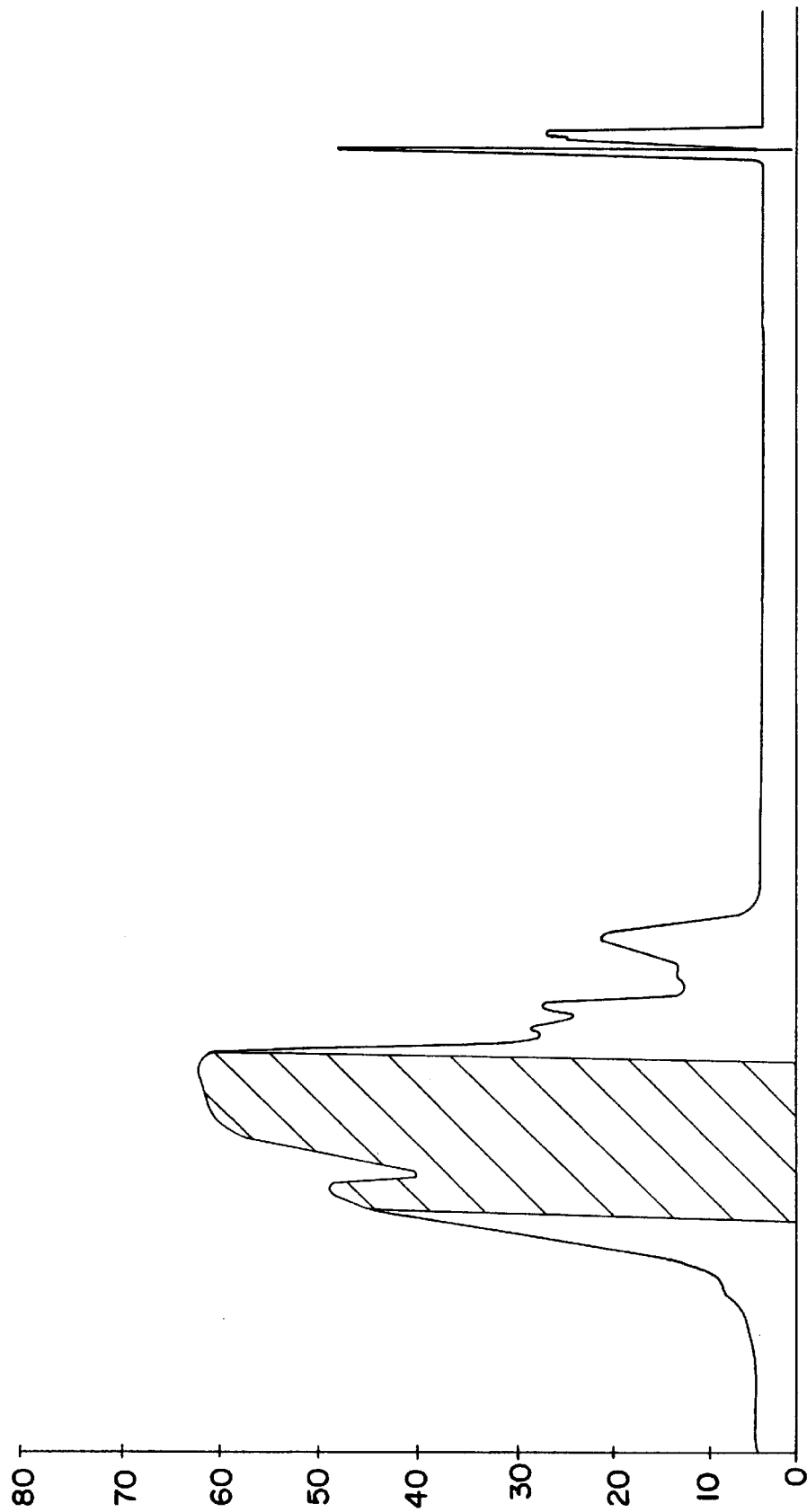
FIG. 4 shows the slow gradients HPLC profile of PAI fractions from FIG. 3. The cross-hatched area contains the bioactive fractions.
Figure 5:
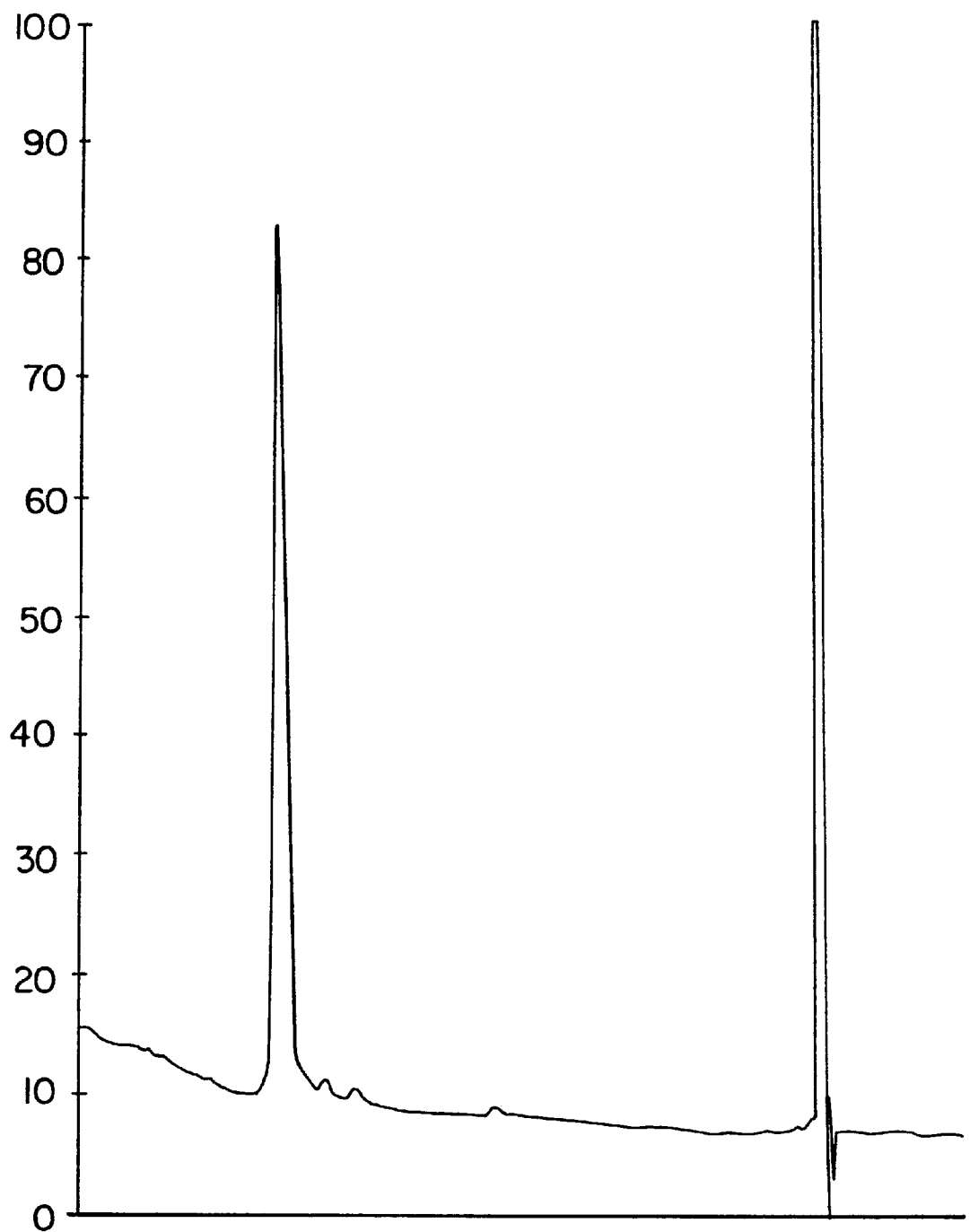
FIG. 5 shows the analytical HPLC profile of PAI fractions from FIG. 4 to demonstrate purified PAI from Eristicophis macmahoni venom.

As shown in FIG. 4, the activity eluted at 24% acetonitrile. The active fractions were then subjected to analytical HPLC with detection at 220 am and eluted as a single symmetric bioactive component as shown in FIG. 5. Amino acid analysis of the HPLC-purified material showed that the peptide contains 49 residues including 7–8 cysteines, as set forth in Table 2.

Attempts at automated Edman degradation of the carboxyamidomethylated peptide did not yield any detectable sequence. Therefore, digestion of this material was performed with Lys-C and Asp-N endoproteinases yielding fragments which were sequenced and are shown in FIG. 6. This analysis revealed a sequence of 48 residues. However, since two tryptophan residues are apparent from this sequence analysis which were not determined in the amino acid composition, the intact peptide contains 51 amino acid residues. Thus, two Glx and one Arg residues missing from the determined sequence were presumably present at the blocked amino terminus of the peptide. Since it was quite likely that one of the Glx residues was a pyroglutamyl residue at the amino terminus leading to the blocked nature of the intact peptide, we removed this group from the intact, carboxyamidomethylated peptide with the enzyme pyroglutamyl aminopeptidase (L-pyroglutamyl peptide hydrolase, EC 3.4.11.8, Boehringer Mannheim Biochemicals, Indianapolis, Ind.). Protocols described by Podell and Abraham, *Biochem Biophys Res Commun* (1978) 81:176–185 were used. Digestion of 100 ug of peptide with the peptidase at a substrate-to-enzyme ratio of 100:1, followed by reversed-phase HPLC purification of the mixture on a Waters analytical C-18 column gave material suitable for automated Edman degradation. The results of this analysis and the assignment of the entire sequence of this peptide which was named "eristicophin," is shown in FIG. 6A.

The complete amino acid sequence of this PAI, is shown in FIG. 6. This peptide has RGD in the binding region and shows considerable homology to echistatin.

EXAMPLE 3

Purification of PAI from *Sistrurus catenatus tergeminus* Venom

Three hundred sixty mg of *Sistrurus c. tergeminus* venom (Miami Serpentarium Labs, Lot #ST6Sz) was dissolved in 7.0 ml of 0.5M acetic acid and applied to a column of Sephadex G-50 fine (Pharmacia, 2.5×100 cm) equilibrated and eluted with 0.5M acetic acid. The column was run at a flow rate of approximately 25 ml/hr and 5-ml fractions collected. Twenty-five ul of each fraction was pooled in groups of 10 fractions (i.e., fractions 1–10, 11–20, etc.) and lyophilized for analysis. The dried pooled fractions were redissolved in water and aliquots assayed for inhibitory activity in ADP-stimulated aggregation of human platelets. Active fractions (31–40) were pooled and lyophilized.

This material was dissolved in 2 ml of 0.5% TFA and loaded onto a 19 mm×30 cm C-18 Delta Pak reverse-phase HPLC column (Waters) equilibrated with 8% acetonitrile containing 0.1% TFA. A gradient from 8% to 30% acetonitrile concentration over 30 min and then to 60% acetonitrile over twenty min was run at a flow rate of 18 ml/min. The column effluent was collected into polypropylene tubes in 0.2 min fractions and monitored at 220 nm/2.2 AUFS. Fractions were concentrated on a Speed-Vac concentrator (Savant), lyophilized and assayed for antiaggregation activity with human platelets as previously described.

Figure 7:
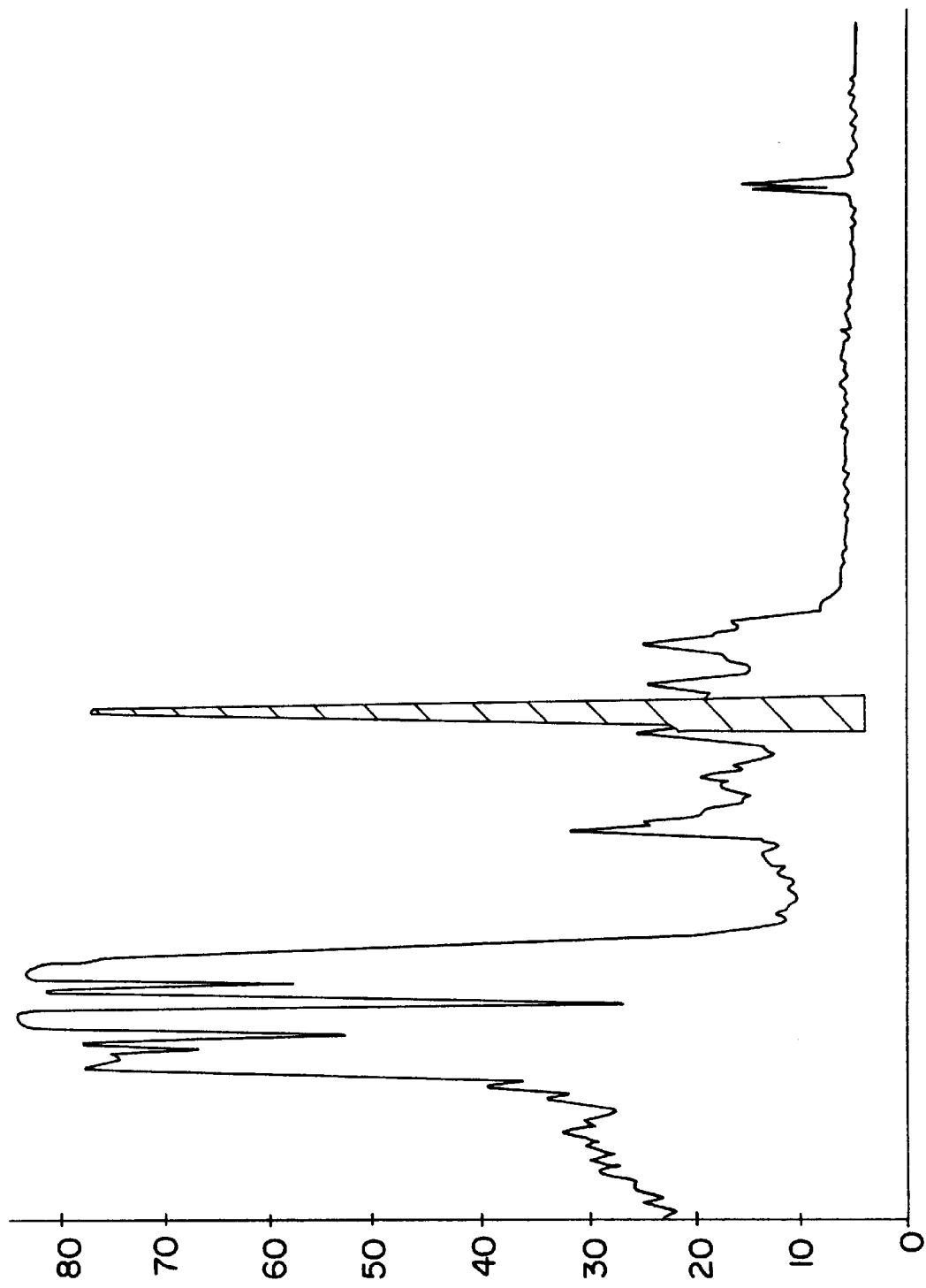
FIG. 7 depicts the HPLC profile of PAI obtained from G-50 fractions of crude Sistrurus c. tergeminus venom. The cross-hatched area contains the bioactive fractions.
Figure 8:
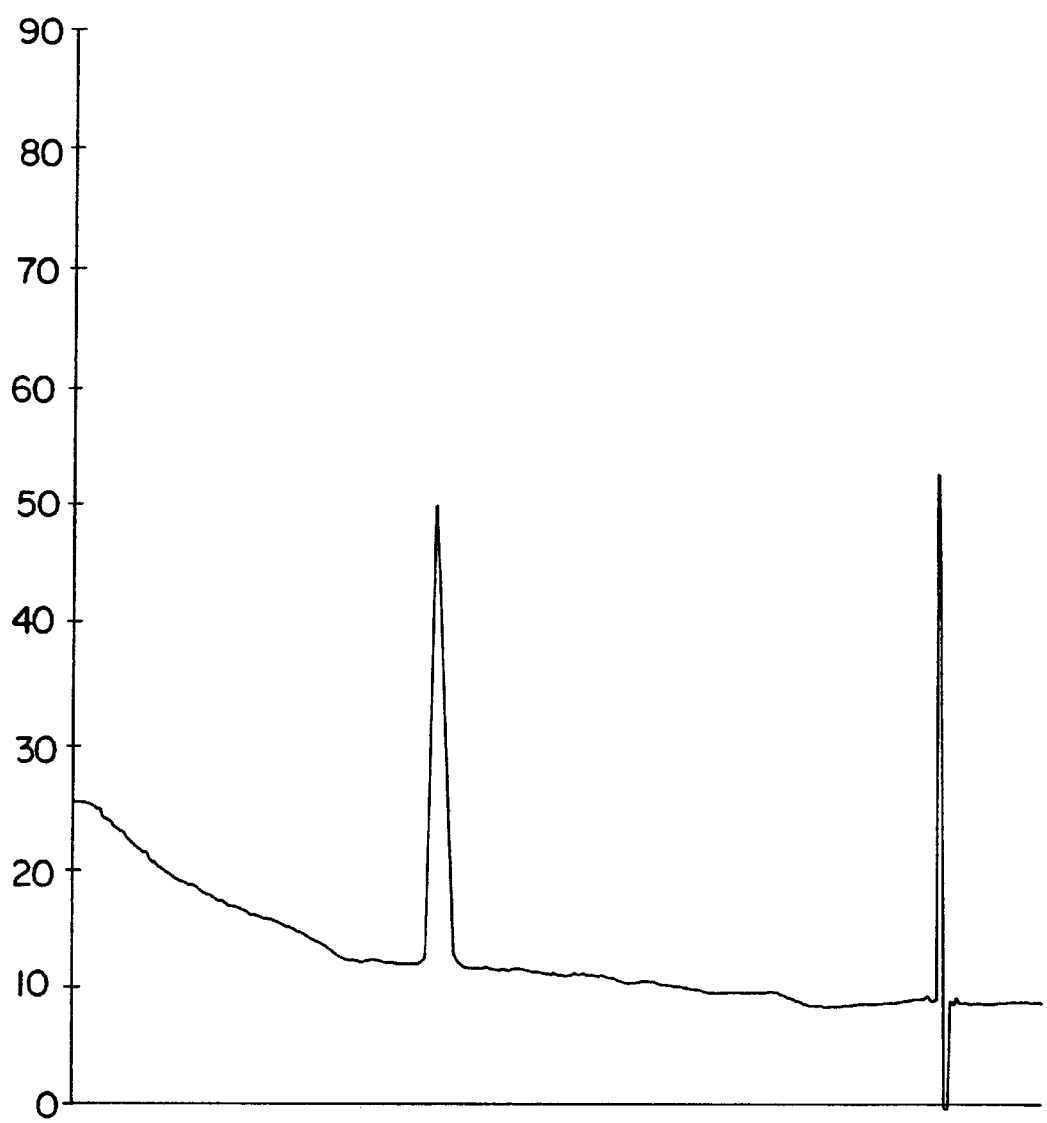
FIG. 8 depicts the HPLC profile of PAI fractions from FIG. 7 to show purified PAI from Sistrurus catenatus tergeminus venom.

FIG. 7 shows that the PAI-containing fraction elutes at 24–25% acetonitrile. Analysis of these active fractions using HPLC with detection at 220 run showed a symmetric bioactive component, as shown in FIG. 8. The amino acid analysis of this material showed a peptide of 71–72 residues, including 12 cysteines, as shown in Table 2.

A portion of the purified peptide was reduced and alkylated with iodoacetamide and purified on a C-18 reverse-phase HPLC column. N-terminal sequence analysis of this material revealed the following amino acid sequence for 23 cycles of Edman degradation: Glu-Ala-Gly-Glu-Glu-Cys-Asp-Cys-Gly-Ser-Pro-Ala-Asn-Pro-Cys-Cys-Asp-Ala-Ala-Thr-Cys-Lys-Leu.

The complete amino acid sequence for this PAI, which was named "tergeminin" is shown in FIG. 6A.

Figure 9:
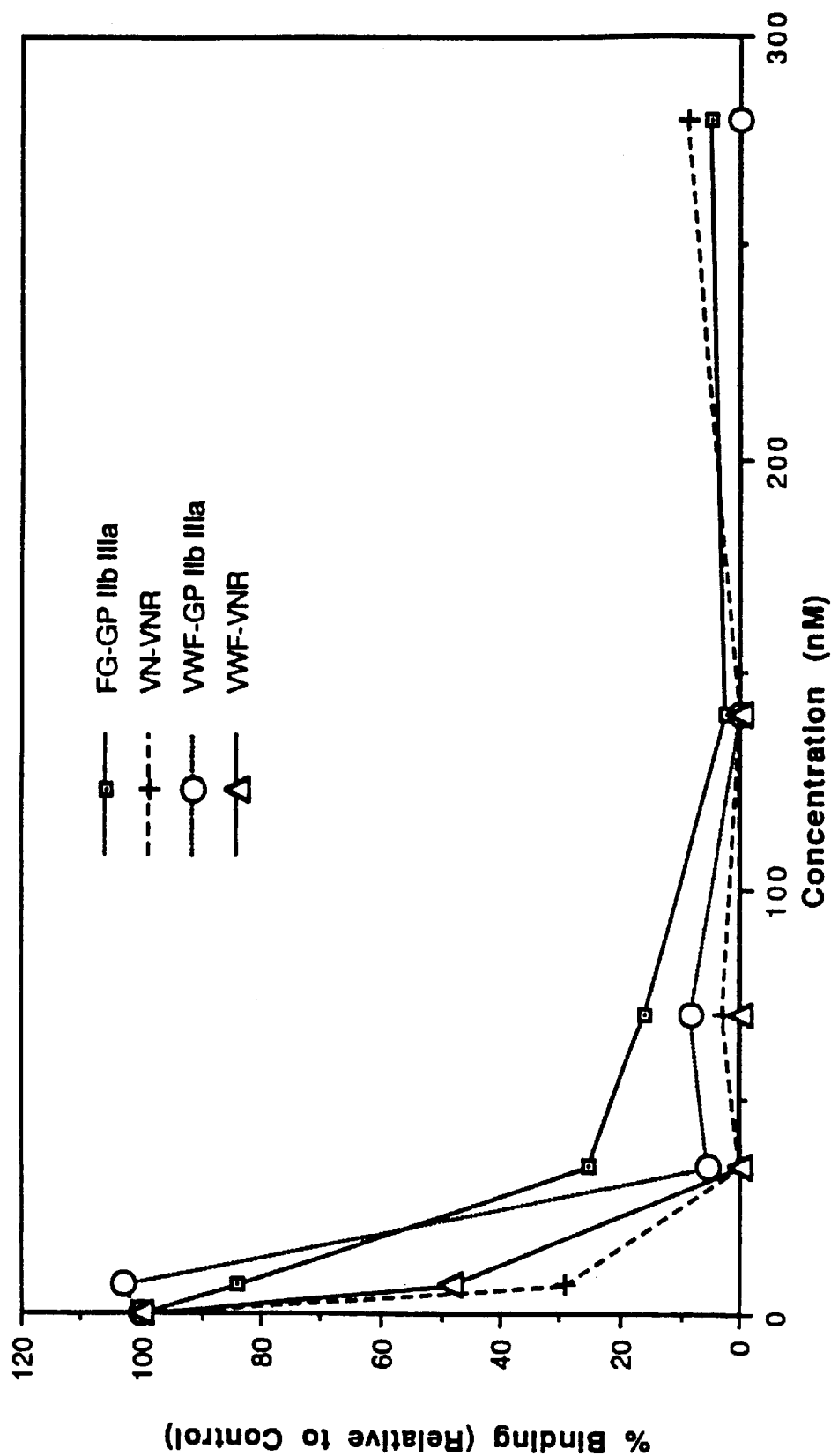
FIG. 9 shows the activity of the purified tergeminin PAI of FIG. 8 in inhibiting binding in several receptor assays.

The purified peptide was tested in the receptor-based assays described in Example 1, paragraph A. Concentrations of pure peptide at less than 100 nM inhibited the binding of Fg and vWF to GP IIb–IIIa and of Vn and vWF to the vitronectin receptor, as shown in FIG. 9.

EXAMPLE 4

Purification of Platelet Aggregation Inhibitor from *Sistrurus milarus barbouri* Venom Two hundred mg of *Sistrurus m. barbouri* venom (Miami Serpentarium Labs, Lot #SM13SZ) was dissolved in 7.0 ml of 0.5M acetic acid and applied to a column of Sephadex G-50 fine (Pharmacia, 2.5×100 cm) equilibrated and eluted with 0.5M acetic acid. The column was run at a flow rate of 26 ml/hr and 5 ml fractions were collected and analyzed for antiplatelet aggregation activity as previously described. Active fractions (41–50) were pooled and lyophilized. This material was redissolved in 2.0 ml 0.5% TFA and loaded onto the preparative C-18 HPLC column as in Example 3 and eluted employing the same gradient conditions. Two-tenths-min fractions from the column were collected into polypropylene tubes, concentrated, lyophilized and analyzed for platelet aggregation inhibitory activity.

Figure 10:
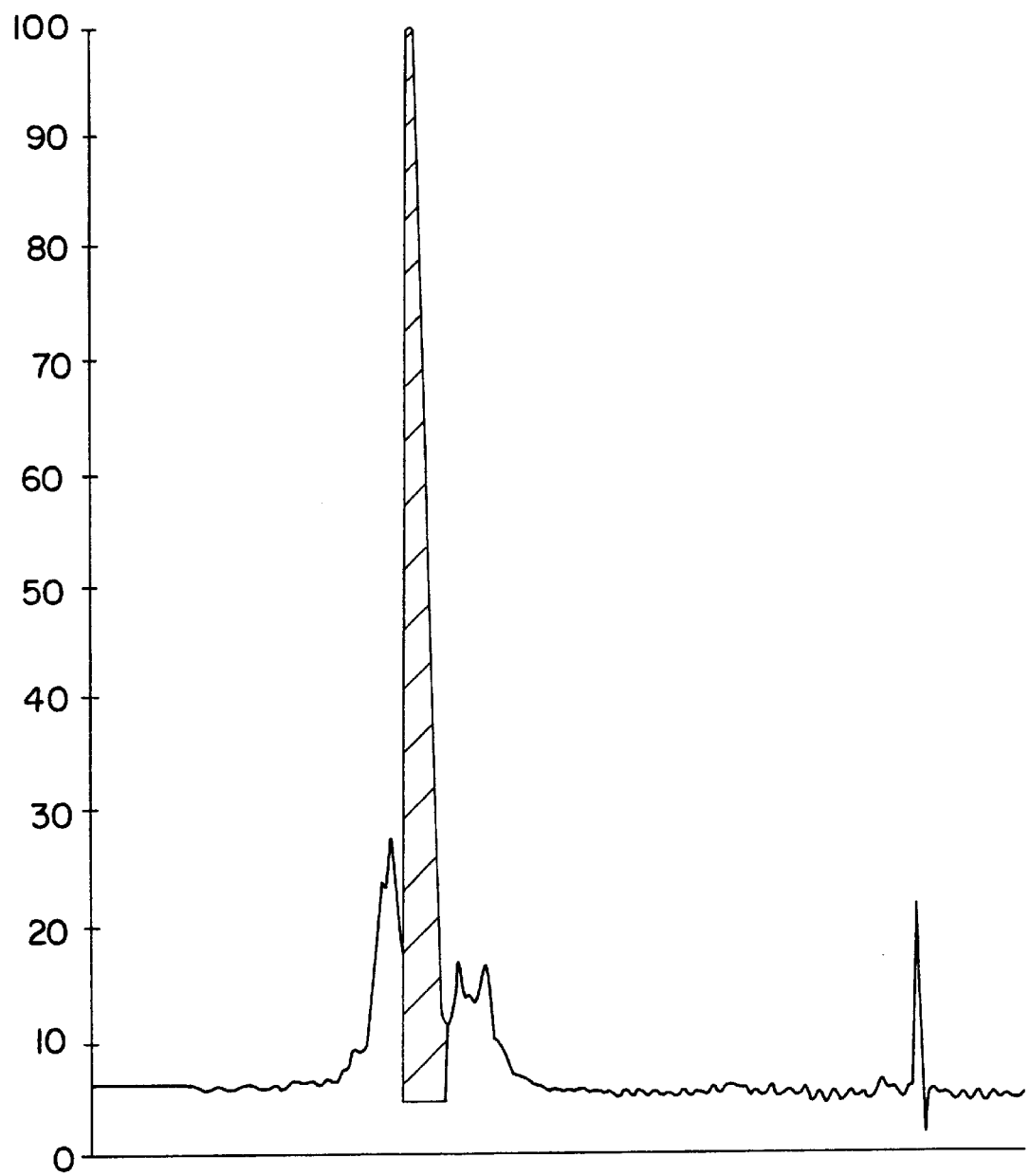
FIG. 10 depicts the HPLC profile of platelet aggregation inhibitor obtained from G-50 fractions of crude Sistrurus m. barbouri venom. The cross-hatched areas contain the bioactive fractions.
Figure 11:
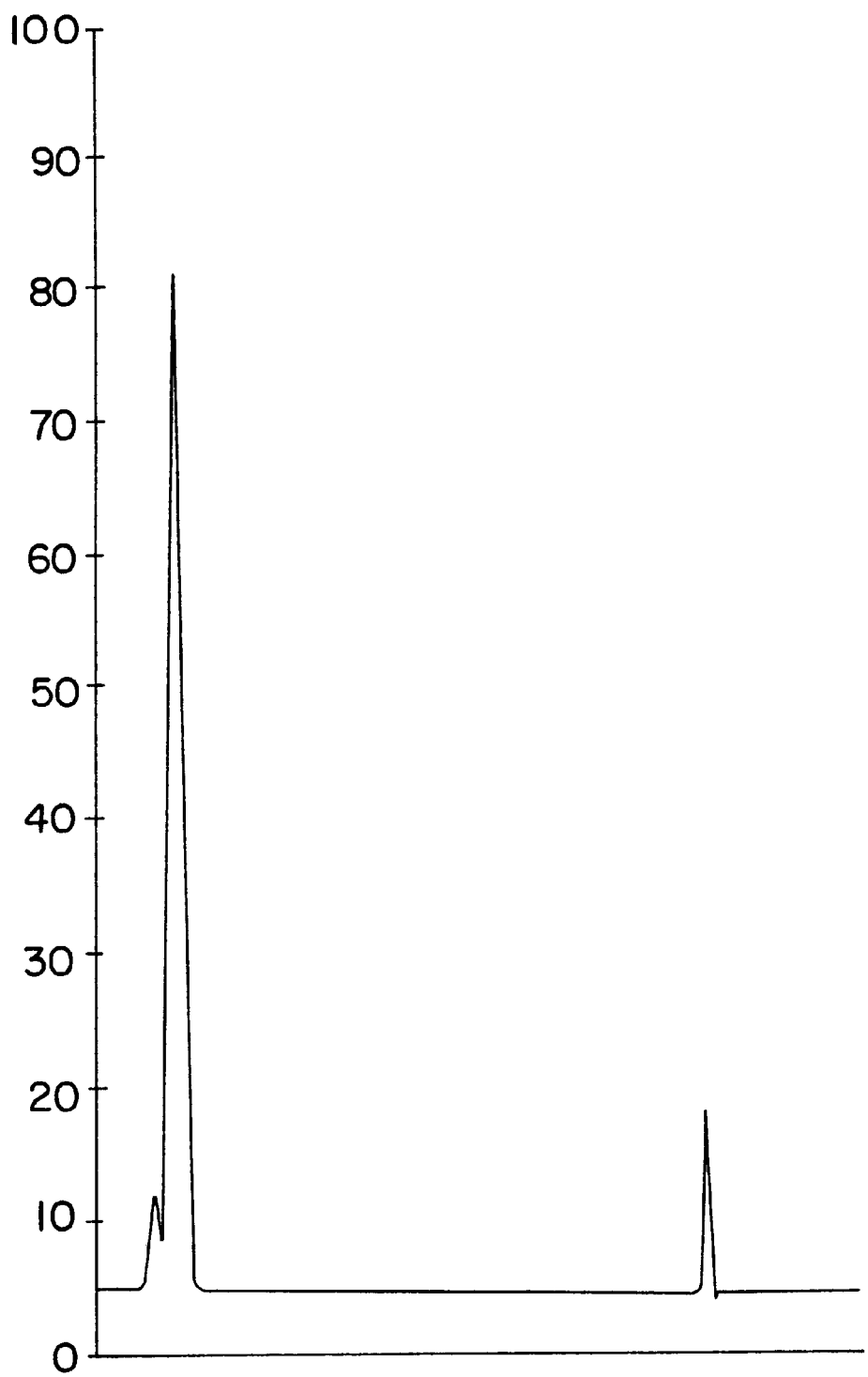
FIG. 11 depicts the HPLC profile of active PAI fractions of FIG. 10 to show purified PAI from Sistrurus milarus barbouri venom.

FIG. 10 shows the activity profile from this HPLC column. The active fractions were subjected to analytical HPLC, which showed several fractions (45–47) which were more than 90% homogeneous. The peptide of fraction 46 (150 ug) was purified to homogeneity on an analytical C-18 column with manual collection of the symmetric peak, as shown in FIG. 11. Amino acid analysis of this material showed a peptide of 71–72 amino acids, including 12 cysteine residues, as set forth in Table 2.

The purified peptide (150 ug) was dissolved in 300 ul reaction buffer (6M guanidine HCl, 0.25M Tris-HCl, 20 mM EDTA, 20 mM dithiothreitol (DTT), pH 7.5) for 1.5 hours at room temperature to reduce the peptide. This was followed by reaction of 3 ul of 4-vinylpyridine (Aldrich) at room temperature for an additional hour. The reaction was stopped by addition of 200 ul 1% TFA and loaded onto an analytical C-18 HPLC column and eluted with an acetonitrile gradient in water containing 0.1% TFA, starting at 8% acetonitrile and running to 25% acetonitrile in 20 minutes, then to 60% acetonitrile in 10 minutes.

A portion of this pyridylethylated material was submitted to N-terminal sequence analysis, as described above, and exhaustive proteolytic cleavage of the reduced and alkylated peptide was performed using endoproteinase Lys-C and endoproteinase Asp-N with peptide fragments isolated on either C-3 or C-18 reverse-phase HPLC columns using acetonitrile/water/TFA gradient elution. The amino acid sequence of the N-terminus of the intact peptide and isolated proteolytic fragments were determined as described by Yarden, Y., et al., *Nature* (1986) 323:226, using automated Edman degradation on a gas-phase sequencer.

The complete amino acid sequence of this isolated peptide, designated "barbourin" is shown in FIG. 6A, along with the sequences for the proteolytic fragments. A comparison of this sequence with those of other snake venom adhesion inhibitors is shown in FIG. 12.

EXAMPLE 5

Purification of PAI from *Lachesis mutas* venom 99 mg of *Lachesis mutas* venom (Miami Serpentarium Labs, Lot #LM15FZ) was dissolved in 2.0 ml of 0.5% trifluoroacetic acid was cooled on ice for 20 min, spun at 14,000 rpm for 3 min to remove insoluble material and loaded onto a 3.9 mm ×30 cm, C-18 Delta Pak reversed-phase HPLC column (Waters) equilibrated with 5% acetonitrile containing 0.1% trifluoroacetic acid. A gradient form 5% to 15% acetonitrile over 5 min and then to 30% over 35 min (2%/min) and continued to 60% acetonitrile over 20 min was run. The flow rate was maintained at 1.5 ml/min and the column effluent monitored at 220 nm/3.0 AUFS. Two minute fractions were collected, concentrated by Speed-Vac and lyophilized. Fractions were assayed for platelet aggregation inhibitory activity.

FIG. 13 shows the active fractions which elute at 18% acetonitrile. These fractions were rerun on the C-18 column using a shallower gradient consisting of a 40 min gradient from 5–28% acetonitrile. One-min fractions were collected, concentrated, lyophilized and assayed for platelet aggregation inhibition activity, with the results shown in FIG. 14. These active fractions were run on an analytical C-18 column, and the eluted center peak fraction collected by hand. The eluted material, which is in a single symmetric peak, as shown in FIG. 15, was subjected to amino acid analysis and showed a peptide of 72–73 amino acids containing 12 cysteines, as shown in Table 2.

The complete amino acid sequence of this PAI, called "lachesin" is shown in FIG. 6B.

EXAMPLE 6

Purification of PAI from *Crotalus viridis viridis* venom 47 mg of *Crotalus viridis viridis* venom (Sigma Chemical Co., Lot #24F-0534) was dissolved in 1 ml of 0.5% trifluoroacetic acid, cooled on ice for 20 min, spun at 14,000 rpm for 3 min to remove insoluble material and loaded onto a 3.9 mm×30 cm C-18 Delta Pak reverse-phase HPLC column (Waters) equilibrated with 5% acetonitrile containing 0.1% trifluoroacetic acid. A gradient from 5% to 15% acetonitrile over 5 min (2%/min) followed by a gradient from 15% to 30% acetonitrile in 35 min and then to 60% acetonitrile in 60 min was run. A flow rate of 1.5 ml/min was maintained throughout the gradient and the column effluent was collected into polypropylene tubes in 2 min fractions. The column effluent was monitored at 220 nm/3.0 AUFS. Fractions were concentrated, lyophilized and assayed for platelet aggregation inhibitory activity.

The active fractions, shown in FIG. 16 as 18–19% acetonitrile, were run on the C-18 HPLC column using a gradient of 8%–20% acetonitrile over 48 min (0.25%/min). The fractions were concentrated and lyophilized and tested for activity; the active fractions were run on a C-18 column using 8–16% acetonitrile over 10 min, 16–20% acetonitrile over 15 min, and then to 60% over 10 min. The effluent was monitored at 220 nm with individual peaks collected by hand into polypropylene tubes. Reanalysis of the active peak on analytical HPLC gave the results shown in FIG. 17. The amino acid analysis conducted on this peak showed a 72–73-residue peptide containing 12 cysteines, as set forth in Table 2. The complete amino acid sequence of this PAI called "viridin" is shown in FIG. 6C and is compared to other PAI in FIG. 12A.

TABLE 2

Amino acid Compositions of Purified Peptides

| Amino acid | Sistrurus m. barbouri | Sistrurus c. tergeminus | Lachesis mutas | Crotalus v. viridis | Eristicophis macmahoni |
|---|---|---|---|---|---|
| Lys | 4 | 3 | 4 | 3–4 | 4 |
| His | 0 | 0 | 0–1 | 1 | 0 |
| Arg | 4 | 5 | 7 | 5 | 7 |
| Asx | 11 | 11 | 10 | 11 | 7 |
| Thr | 4 | 4 | 2 | 4 | 2 |
| Ser | 2 | 2 | 1 | 2 | 1 |
| Glx | 6–7 | 5–6 | 7 | 6 | 4 |
| Pro | 4 | 4 | 5 | 6 | 5 |
| Gly | 9 | 9 | 9 | 10 | 5 |
| Ala | 7 | 8 | 9 | 7 | 3 |
| Cys | 12 | 12 | 12 | 12 | 7 |
| Val | 2 | 2 | 0 | 1 | 2 |
| Met | 1 | 1 | 0 | 0 | 0 |
| Ile | 0 | 0 | 2 | 1 | 0 |
| Leu | 3 | 3 | 2 | 3 | 0 |
| Tyr | 1 | 1 | 1 | 1 | 1 |
| Phe | 1 | 1 | 1 | 1 | 1 |
| | 71–72 | 71–72 | 72–73 | 74–75 | 49 |

EXAMPLE 7

Comparison of Purified PAI to Echistatin

The peptides purified as described in Examples 2 and 4, eristicophin and barbourin, were compared to the 49-residue peptide echistatin in inhibiting fibrinogen binding to GP IIb–IIIa, as described in Example 1, paragraph A. FIG. 18 shows that these purified PAIs are 2–3 times more potent in this assay than the standard echistatin.

Peptides purified to homogeneity from *Echis carinatus*, *Sistrurus m. barbouri*, and *Eristicophis macmahoni* venoms were compared to echistatin in the ADP-stimulated platelet aggregation assay. Increasing concentrations of purified snake venom peptides were added (without preincubation) at the indicated concentrations (FIGS. 19A, 19B, and 19C). Snake venom peptides from *Eristicophis macmahoni* and *Sistrurus m. barbouri* were at least twofold more potent than echistatin, in agreement with their order of potency observed for inhibiting fibrinogen binding to GP IIb–IIIa as presented above.

EXAMPLE 8

Purification of PAI from *Crotalus cerastes cerastes* venom

One gram of *Crotalus c. cerastes* venom (Miami Serpentarium Labs, Lot #CE4SZ) was dissolved in 7.0 ml of 0.5M acetic acid and applied to a column of Sephadex G-50 fine (Pharmacia, 2.5×100 cm) equilibrated and eluted with 0.5M acetic acid. The column was run at a flow rate of 25 ml/hr with 5 ml fractions collected into polypropylene tubes. Aliquots of these fractions were assayed for aggregation activity inhibitory activity as previously described. Active fractions (71–80) were pooled and lyophilized. The dried material was resuspended in 2.0 ml of 0.5% TFA, insoluble material removed by centrifugation and loaded onto the preparative C-18 Waters HPLC column as described in Example 3 and eluted employing the gradient elution conditions described in Example 3. Fractions from the column were collected into polypropylene tubes, concentrated and analyzed for platelet aggregation inhibitory activity. FIG. 20 shows the activity profile from this HPLC fractionation.

Active fractions with platelet aggregation inhibitory activity were pooled and lyophilized and rerun on the preparative C-18 HPLC column eluted with the same gradient. Fractions were collected by hand into polypropylene tubes and again assayed for platelet aggregation inhibitory activity as before. Active fractions were analyzed on an analytical C-18 column using the conditions described in Example 4 and homogeneous fractions were pooled and lyophilized. Analytical HPLC analysis of this material is shown in FIG. 21.

Purified peptide was subjected to amino acid analysis revealing that it was a peptide of 73–74 amino acids containing 12 cysteine residues, as set forth in Table 3.

The purified peptide (450 ug) was dissolved in 750 ul reaction buffer (6M guanidine-HCl, 0.25M Tris-HCl, 20 mM EDTA, 20 mM dithiothreitol (DTT), pH 7.50) for 1.5 hr at room temperature to fully reduce the peptide followed by reaction at room temperature for 1 hr with excess iodoacetamide (Fluka, 16 mg). The reaction was stopped by addition of 500 ul of 1% TFA and loaded onto an analytical C-18 HPLC column and eluted with a gradient of acetonitrile from 8% to 25% in 20 minutes, then to 60% acetonitrile in 10 minutes. The UV absorbing peak was collected by hand into 1.5 ml eppendorf tubes and dried.

A portion of this carboxyamidomethylated peptide was submitted to N-terminal sequence analysis. Exhaustive proteolytic cleavage of the carboxyamidomethylated peptide was performed using endoproteinase Lys-C and endoproteinase Asp-N. Peptide fragments from these digests were isolated on either C-3 or C-18 reversed-phase HPLC columns using acetonitrile/water/TFA gradient elution conditions. Amino acid sequence was determined as described in Example 4. The complete amino acid sequence determined for "cerastin" is shown in FIG. 6A, and is compared to that of other PAI in FIG. 12A.

TABLE 3

Amino Acid Compositions

| Amino acid | Crotalus c. cerastes | Crotalus atrox | Crotalus d. durissus | Crotalus d. totonatacus | Crotalus h. horridus | Bothrops cotiara |
|---|---|---|---|---|---|---|
| Lys | 3 | 3 | 3 | 3 | 4 | 3 |
| His | 0 | 0 | 0 | 0 | 0–1 | 0 |
| Arg | 5 | 5 | 5 | 5 | 4 | 8 |
| Asx | 11 | 10 | 12 | 12 | 10 | 10 |
| Thr | 5 | 4 | 4 | 4 | 3 | 2 |
| Ser | 1 | 2 | 2 | 2 | 2 | 1 |

TABLE 3-continued

Amino Acid Compositions

| Amino acid | Crotalus c. cerastes | Crotalus atrox | Crotalus d. durissus | Crotalus d. totonatacus | Crotalus h. horridus | Bothrops cotiara |
|---|---|---|---|---|---|---|
| Glx | 7 | 6 | 5–6 | 5–6 | 6 | 8 |
| Pro | 5 | 6–7 | 4–5 | 5 | 7 | 6 |
| Gly | 9 | 8 | 10 | 10 | 8 | 8 |
| Ala | 7 | 6 | 8 | 8 | 8 | 9 |
| Cys | 12 | 12 | 12 | 12 | 10 | 12 |
| Val | 2 | 2 | 1 | 1 | 3 | 0 |
| Met | 1 | 0 | 0 | 0 | 1 | 0 |
| Ile | 0 | 1 | 1 | 1 | 0 | 1 |
| Leu | 3 | 3 | 3 | 3 | 2–3 | 2 |
| Tyr | 1 | 1 | 1 | 1 | 1 | 0 |
| Phe | 1 | 1 | 1 | 1 | 1 | 2 |
| Trp | n.d. | n.d. | n.d. | n.d. | n.d. | n.d. |
|  | 73–74 | 70–71 | 72–74 | 73–74 | 70–72 | 72 |

EXAMPLE 9

Purification of PAI from *Crotalus ruber ruber* venom

One gram of *Crotalus ruber ruber* venom (Miami Serpentarium labs, Lot #CF17SZ) was dissolved in 8 ml of 0.5M acetic acid and applied to a column of Sephadex G-50 fine (Pharmacia, 2.5×100 cm) equilibrated at room temperature and eluted with 0.5M acetic acid. The column was run at a flow rate of 25 ml/hr with 5 ml fractions collected into polypropylene tubes. Aliquots of fractions were assayed for platelet aggregation inhibitory activity as described. Active fractions (61–70) were pooled and lyophilized. The dried material was resuspended in 2.0 ml of 0.5% TFA. Insoluble material was removed by centrifugation and loaded onto a preparative C-18 Water HPLC column as described and eluted employing the gradient conditions described in Example 3. Fractions collected into polypropylene tubes were concentrated on a Speed-Vac concentrator and analyzed for platelet aggregation inhibitory activity.

FIG. 22 shows the activity profile for this HPLC fractionation. Individual active fractions were lyophilized. Fractions 49 and 50 were pooled and loaded onto the analytical C-18 reversed phase column and eluted using conditions described in Example 4 which consisted of an acetonitrile gradient running from 8% acetonitrile to 25% in twenty minutes followed in ten minutes to 69% acetonitrile to yield homogeneous peptide which we have called "ruberin." Automated Edman degradation of carboxyamidometylated peptide give the sequence shown in FIG. 6B.

EXAMPLE 10

Purification of PAI from *Crotalus atrox*

One gram of *Crotalus atrox* venom (Miami Serpentarium Labs, Lot #CX16AZ) was dissolved in 10 ml of 0.5M acetic acid and applied to a column of Sephadex G-50 fine (Pharmacia, 2.5×110 cm) equilibrated and run at room temperature with 0.5M acetic acid. The column was run at a flow rate of 25 ml/hr with 5 ml fractions collected into polypropylene tubes. Aliquots of fractions were assayed for platelet aggregation inhibitory activity as previously described. Active fractions (81–100) were pooled and lyophilized. The dried material was dissolved in 2.0 ml of 0.5% TFA and loaded onto the preparative C-18 HPLC column and run as described in Example 3. Fractions from the column were collected into polypropylene tubes, concentrated on a Speed-vac concentrator and assayed for platelet aggregation inhibitory activity as before. Active fractions were rerun on the analytical C-18 column to yield homogeneous peptide (FIG. 23). Amino acid analysis of this material revealed that the peptide contains 72 amino acids including 12 cysteine residues, as shown in Table 3. The amino acid sequence of the isolated peptide, crotatroxin, is shown in FIG. 6B.

EXAMPLE 11

Purification of PAI from *Bothrops cotiara*

Six hundred eighty milligrams of *Bothrops cotiara* venom (Miami Serpentarium Labs, Lot #BO5SZ) was dissolved in 10 ml of 0.5M acetic acid and loaded onto a column of Sephadex G-50 fine (Pharmacia, 2.5×110 cm) equilibrated and eluted with 0.5M acetic acid. The column was run at a flow rate of 25 ml/hr with 5 ml fractions collected into polypropylene tubes. Aliquots of fractions were assayed for platelet aggregation inhibitory activity as described previously. Active fractions (71–90) were pooled and lyophilized. Dried material was resuspended into 2.0 ml of 0.5% TFA and loaded onto the Waters preparative C-18 reverse-phase column. The column was eluted using the conditions described in Example 3. Fractions were collected into polypropylene tubes, concentrated on a Speed-Vac concentrator and assayed for platelet aggregation inhibitory activity. Active fractions were individually lyophilized. Several peak fractions were rerun on the analytical C-18 column as described in Example 4. The analytical HPLC profile of homogenous peptide is shown in FIG. 24. Amino acid analysis of this material reveals this peptide to contain 72 amino acids including 12 cysteine residues, as shown in Table 3. Complete amino acid sequence of this peptide which we have called "cotiarin" is shown in FIGS. 6 and 12.

The purified peptide was tested in the receptor assays described in Example 1. Initial determinations showed that low concentrations of cotiarin (1–4 nM) selectively inhibited vitronectin binding to vironectin receptor, whereas the same concentrations had significantly lower inhibiting activity in binding of fibrinogen to GP IIb–IIIa as shown in FIG. 25; however, subsequent experiments failed to verify this result.

EXAMPLE 12

Purification of PAI from *Crotalus viridis lutosus*

A. One gram of *Crotalus viridis lutosus* venom (Miami Serpentarium Labs, Lot #CL18SZ) was dissolved in 8 ml of 0.5 m acetic acid and applied to a column of Sephadex G-50 fine (Pharmacia, 2.5×110 cm) which was equilibrated and eluted with 0.5M acetic acid. The column was run at a flow rate of 25 ml/hr and 5 ml fractions collected into polypropylene tubes. Aliquots of fractions were assayed for platelet aggregation inhibitory activity. Fractions (71–100) were pooled and lyophilized. Dried material was resuspended in 2.0 ml of 0.5% TFA. Insoluble material was removed by centrifugation and loaded onto the preparative C-18 Waters reversed-phase column and eluted using the gradient elution conditions described in Example 3. Fractions from the column were collected into polypropylene tubes, concentrated on a Speed-Vac concentrator and analyzed for platelet aggregation inhibitory activity. Active fractions were lyophilized in their individual tubes. Fractions with peak activity were rerun on the Waters analytical C-18 column using the acetonitrile gradient described in Example 4. Fractions were collected by hand into 1.5 ml Eppendorf tubes. Homogeneous fractions were pooled and lyophilized. Analytical HPLC of this material showed a single symmetric peak. The complete amino acid sequence of this peptide which we have called "lutosin" is shown in FIGS. 6B and 12B.

B. In a similar manner to that set forth in paragraph A, the PAIs from *B. jararacussu; C. basilicus, C. durissus durissus, C. v. oreganus, C. h. horridis, C. v. helteri, C. durisgus totonactus* and from *C. m. molossus*, were isolated and purified. Amino acid compositions for several of these peptides are shown in Table 3. The amino acid sequences of the PAI from *C. h. horridus, C. basilicus*, and *C. m. molossus*, designated horridin, basilicin and molossin, respectively, are shown in FIG. 6. Receptor binding data for the purified peptides of Examples 1–12 are shown in FIG. 26.

In Examples 13–16 below, peptides were synthesized by solid-phase techniques on an Applied Biosystems 431A Peptide Synthesizer using t-Boc amino acids activated as HOBt active esters in accordance with the instructions of the manufacturer, which are briefly as follows for the preparation of Boc-AA1. . . AA(n–1)-AA AA(n)-O-PAM-polystyrene resin.

One-half mmol of selected Boc-AA(n)-O-PAM-polystyrene resin is treated according to the following schedule for incorporation of the Boc-AA(n–1)-OH:

1) TFA deprotection: 30% TFA in DCM, 3 min, 50% TFA in DCM, 16 min.
2) Washes and neutralizations: DCM washes (5×), 3 min, 5% DIEA in DCM, 2 min, 5% DIEA in NMP, 2 min. NMP wash (6×), 5 min.
3) Coupling: 4 equivalents Boc-AA-HOBt ester in NMP (preactivate 55 min), 38 min, DMSO to make 15% DMSO/85% NMP, 16 min, 3.8 equiv DIEA, 5 min.
4) Wash and resin sample: NMP wash, 3 min.
5) Capping: 10% acetic anhydride, 5% DIEA in NMP, 8 min.
6) Washes: DCM washes (6×) 4 min.

EXAMPLE 13

Preparation of Analog #1 [$E^{28}L^{41}C^{64}$]barbourin (28–73) E-C-A-D-G-L-C-C-D-Q-C-R-F-L-K-K-G-T-V-C-R-V-A-K-G-D-W-N-D-D-T-C-T-G-Q-S-C-D-C-P-R-N-G-L-Y-G One-half mmol of PAM-Gly resin (0.6 meq/g, Applied Biosystems, Foster City, Calif.) was subjected to Procedure A with the required amino acids (introduced in order). The Boc-protected amino acids had the following side-chain protection: Arg(Tos), Asp(OcHex), Cys(4-MeBzl), Glu (OcHex), Lys (Cl-Z), Thr(OBzl), Trp(CHO), and Tyr(Br-Z). Following assembly of the completed protected peptide-resin chain, the amino terminal Boc- group was removed with TFA and the resin dried as its TFA-salt form. The resin (1.3 g) was subjected to "low-high" HF deprotection protocols followed by removal of HF "in vacuo". The dried peptide-resin mixture was transferred to a fritted funnel (coarse) with ethyl ether and was washed several times with alternate washes of ether and chloroform to remove most of the organic protecting groups and scavengers used in the deprotection.

The peptide mixture was transferred to 2 L of 0.4% acetic acid and the pH adjusted to 7.99 with concentrated $NH_4OH$. The resin was filtered from this solution and the solution allowed to sit at 4° C. without stirring for 20 hr. This was followed by warming the solution to room temperature and storing for 3 days again without stirring. Precipitated material was removed by filtration and the supernatant pH adjusted to 3.0 with acetic acid and lyophilized.

The crude material was dissolved in 8.0 ml of 0.5M acetic acid and loaded onto a Sephadex G-50 fine column (2.5×100 cm) equilibrated with 0.5M acetic acid. The column was run at 20 ml/hr and fractions (4 ml) were collected into polypropylene tubes. Aliquots of fractions were dried, resuspended in water and tested for platelet aggregation inhibitory activity as previously described. Active fractions (71–90) were pooled and lyophilized.

Dried material (66 mg) was redissolved in 2.0 ml of 0.1M acetic acid and loaded onto the Waters Preparative C-18 column equilibrated with 8% acetonitrile containing 0.1% TFA. A gradient running from 8% acetonitrile to 20% in 10 minutes followed by a slow gradient to 30% acetonitrile in 40 min was performed. The column was eluted at 18 ml/min and fractions (12 sec) were collected into polypropylene tubes. Fractions were concentrated on a Speed-Vac concentrator to 1.0 ml volume and 10 ul aliquots were tested in the platelet aggregation assay.

Active fractions (29–32) were individually lyophilized and analyzed on the analytical C-18 HPLC column with an 8–30% acetonitrile gradient. Fractions 29 and 30 were pooled and loaded onto the analytical column in 1.0 ml of 0.5% TFA. The major peak was collected manually and lyophilized to yield 1.6 mg of pure peptide.

Amino acid analysis of this material confirmed the identity of the peptide. Assay of this material for its ability to inhibit the binding of fibrinogen to GP IIb–IIIa and vitronectin to VnR is displayed in FIGS. 26 and 27. These data demonstrate the high affinity of this analog for GP IIb–IIIa and the relative lack of affinity for VnR at concentrations up to 1 uM.

EXAMPLE 14

Preparation of Analog #2, [$K^{29}$]eristicophin (4–51): E-E-P-C-A-T-G-P-C-C-R-R-C-K-F-K-R-A-G-K-V-C-R-V-A-K-G-D-W-N-N-D-Y-C-T-G-K-S-C-D-C-P-R-N-P-W-N-G One-half mmol of PAM-Gly resin (0.6 meq/g, Applied Biosystems, Foster City, Calif.) was subjected to Procedure A with the required amino acids (introduced in order). The Boc-protected amino acids had the following side-chain protection: Arg(Tos), Asp(OcHex), Cys(4-MeBzl), Glu(O-cHex), Lys(Cl-Z), Ser(OBzl), Thr(OBzl), Trp(CHO) and Tyr(Br-Z). Cleavage, refolding and purification of this pep-

EXAMPLE 15

Preparation of Analog #3: G-C-G-K-G-D-W-P-C-A-NH$_2$

One-half mmol of pMBRA resin (0.72 meq/g, Applied Biosystems, Foster City, Calif.) was subjected to Procedure A with the required amino acids (introduced in order). The Boc-protected amino acids had the following side-chain protection: Asp(O-cHex), Cys(4-MeBzl), and Lys(Cl-Z). Following completion of the assembly of the protected peptide-resin, the amino terminal Boc group was removed with TFA and the resin dried as its TFA-salt form. The resin (1.54 g) was treated with anhydrous hydrogen fluoride (HF) containing 10% anisole, 2% ethyl methyl sulfide for 30 min at −10° C., and an additional 30 min at 0° C. The HF was removed in vacuo and the peptide/resin mixture was suspended in diethyl ether followed by alternately washing with chloroform and ether 3×. After a final ether wash, the peptide was extracted from the resin with 2.0M acetic acid, diluted with distilled water and lyophilized.

The crude peptide (370 mg) was dissolved in deoxygenated 10 mM NH$_4$OAc, pH 8, to 0.5 mg/ml and allowed to oxidize by dropwise addition of a slight excess of 0.01M potassium ferricyanide (K$_3$Fe(CN)$_6$) solution, stirred an additional 20 min, and adjusted to pH 5 with acetic acid. The peptide solution was treated with DOWEX AG3×4 anion-exchange resin for 15 min with stirring and the resin filtered, diluted with H$_2$O and lyophilized to yield the crude cyclized peptide. The crude cyclized peptide (392 mg) was purified by desalting on Sephadex G-25F using 0.5M acetic acid as eluent, followed by ion-exchange chromatography on CM-Sepharose (Pharmacia) using an elution gradient generated by addition of 100 mM NH$_4$OAc to a solution of 10 mM NH$_4$OAc, pH 4.5. Fractions which had a minimum purity of 90% by HPLC analysis were pooled and lyophilized from H$_2$O several time to yield 175 mg. Final purification consisted of preparative HPLC purification on a Water C-18 reverse-phase column with an acetonitrile/water/TFA gradient to yield purified peptide. Receptor binding data for this analog are shown in FIGS. 26 and 29B.

EXAMPLE 16

Preparation of Additional Analogs

The following analogs were synthesized; in most cases in a manner similar to that set forth in Example 15. However, analog 60, shown below, was prepared in solution via guanidation of the side chain of the lysine residue of analog #19 using the procedure of Bajusz, S., et al., *FEBS Letts* (1980) 110:85–87.

One mg of analog #19 was reacted with 1 mg of 1-amidino-3,5-dimethylpyrazole nitrate (Aldrich) in 1 ml of absolute ethanol in the presence of diisopropylethylamine (DIEA) at room temperature for 4 days. The product analog 60 was purified from excess reagent and starting materials by reversed-phase HPLC on a C-18 column using a gradient of acetonitrile in 0.1% trifluoroacetic acid. Nine hundred ug of this material was isolated in purified form.

4 G-C-K-G-D-W-P-C-A-NH$_2$
5 C-G-K-G-D-W-P-C-NH$_2$
6 G-C-G-K-G-D-W-C-A-NH$_2$
7 G-C-K-G-D-W-C-A-NH$_2$
8 Acetyl-C-K-G-D-C-NH$_2$
9 Mpr-K-G-D-Pen-NH$_2$
10 C-K-G-D-W-P-C-NH$_2$
11 Acetyl-C-R-G-D-Pen-NH$_2$
12 C-K-G-D-Y-P-C-NH$_2$
13 C-K-G-D-F-P-C-NH$_2$
19 Mpr-K-G-D-W-P-C-NH$_2$
34 C-K-G-D-W-G-C-NH$_2$
35 C-K-G-E-W-P-C-NH$_2$
36 C-Orn-G-D-W-P-C-NH$_2$
37: C-K-A-D-W-P-C-NH$_2$
38: C-K-A°-D-W-P-C-NH$_2$
39: C-K-G-D-W-(Sar)-C-NH$_2$
40: C-K(Formyl)-G-D-W-P-C-NH$_2$
41: C-K-G-D-I-P-C-NH$_2$
42: C-K-G-D-(4-Cl-Phe)-P-NH$_2$
43: C-K-(Sar)-D-W-P-C-NH$_2$
44: C-K-G-D-(4-NO$_2$-Phe)-P-C-NH$_2$
45: C-K-G-D-(NMePhe)-P-C-NH$_2$
46: C-H-G-D-W-P-C-NH$_2$
47: Acetyl-C-K-G-D-W-P-C-NH$_2$
48: Mpr-K-G-D-W(Formyl)-P-C-NH2
49: Mvl-K-G-D-W-P-C-NH$_2$
50: Mpr-K-G-D-W°-P-Pen-NH$_2$
51: Mpr-K-G-D-W-P-Pen-NH$_2$
52: Mpr-K-G-D-W-P-Pen°-NH$_2$
53: Mpr-K-G-D-W-P°-Pen-NH$_2$
54: Mpr-K-G-D°-W-P-Pen-NH$_2$
55: Mpr-K-G-D-W-(Thz)-C-NH$_2$
56: Mpr-K-G-D-H(2,4-DNP)-p-C-NH$_2$
57: Mpr-K-G-D-(2-Nal)-p-Pen-NH$_2$
58: Mvl-K-G-D-W-P-Pen-NH$_2$
59: Mpr-K-G-D-W-(Pip)-Pen-NH$_2$
60: Mpr-(Har)-G-D-W-P-C-NH$_2$
61: Mpr-K-G-D-W-P-C°-NH$_2$
62: Mpr-(D-Lys)-G-D-W-P-Pen-NH$_2$
63: Mpr-(Har)-G-D-W-P-Pen-NH$_2$
64: Mpr-(Acetimidyl-Lys)-G-D-W-P-C-NH$_2$
65: Mpr-(Acetimidyl-Lys)-G-D-W-P-Pen-NH$_2$
66: Mpr-(N$^G$, N$^{G'}$-ethylene-Har)-G-D-W-P-C-NH$_2$
67: Mpr-(N$^G$, N$^{G'}$-ethylene-Har)-G-D-W-P-Pen-NH$_2$
68: Mpr-Har-Sar-D-W-P-C-NH$_2$
69: Mpr-(Acetimidyl-Lys)-G-D-W-P-Pen-NH$_2$

EXAMPLE 17

PAI Activity of Peptides

When tested in the standard aggregation inhibition assays described above, analogs #3–5 had IC$_{50}$ values of 5 uM for ability to inhibit ADP-induced human platelet aggregation. However, analog #6 has an IC$_{50}$ of more than 200 uM, and analog #7, 100 uM. IC$_{50}$ values for the analogs of the invention in this assay are as follows:

| Analog | Sequence | Appr. IC$_{50}$ (uM) |
|---|---|---|
| #3 | G—C—G—K—G—D—W—P—C—A—NH$_2$ | 5 |
| #4 | G—C—K—G—D—W—P—C—A—NH$_2$ | 5 |
| #5 | C—G—K—G—D—W—P—C—NH$_2$ | 5 |
| #6 | G—C—G—K—G—D—W—C—A—NH$_2$ | >200 |
| #7 | G—C—K—G—D—W—C—A—NH$_2$ | 100 |
| #8 | Acetyl—C—K—G—D—C—NH$_2$ | 200 |
| #9 | Mpr—K—G—D—Pen—NH$_2$ | 25 |
| #10 | C—K—G—D—W—P—C—NH$_2$ | 5 |
| #11 | Acetyl—C—R—G—D—Pen—NH$_2$ | 5 |
| #12 | C—K—G—D—Y—P—C—NH$_2$ | 12 |
| #13 | C—K—G—D—F—P—C—NH$_2$ | 20 |
| #19 | Mpr—K—G—D—W—P—C—NH$_2$ | 1 |
| #34 | C—K—G—D—W—G—C—NH$_2$ | 100 |
| #35 | C—K—G—E—W—P—C—NH$_2$ | >300 |
| #36 | C—Orn—G—D—W—P—C—NH$_2$ | 150–200 |
| #37 | C—K—A—D—W—P—C—NH$_2$ | 100 |
| #38 | C—K—A†—D—W—P—C—NH$_2$ | >200 |
| #39 | C—K—G—D—W—(Sar)—C—NH$_2$ | 5 |
| #40 | C—K(Formyl)—G—D—W—P—C—NH$_2$ | >200 |
| #41 | C—K—G—D—I—P—C—NH$_2$ | 100 |
| #42 | C—K—G—D—(4-Cl—Phe)—P—NH$_2$ | 20 |
| #43 | C—K—(Sar)—D—W—P—C—NH$_2$ | 50 |
| #44 | C—K—G—D—(4-NO$_2$—Phe)—P—C—NH$_2$ | 75 |
| #45 | C—K—G—D—(NMePhe)—P—C—NH$_2$ | >200 |
| #46 | C—H—G—D—W—P—C—NH$_2$ | 200 |
| #47 | Acetyl—C—K—G—D—W—P—C—NH$_2$ | 2.5 |
| #48 | Mpr—K—G—D—W(Formyl)—P—C—NH$_2$ | 1 |
| #49 | Mvl—K—G—D—W—P—C—NH$_2$ | 1.5 |
| #50 | Mpr—K—G—D—W†—P—Pen—NH$_2$ | >200 |
| #51 | Mpr—K—G—D—W—P—Pen—NH$_2$ | 0.75 |
| #52 | Mpr—K—G—D—W—P—Pen†—NH$_2$ | 5 |
| #53 | Mpr—K—G—D—W—P†—Pen—NH$_2$ | >200 |
| #54 | Mpr—K—G—D†—W—P—Pen—NH$_2$ | >100 |
| #55 | Mpr—K—G—D—W—(Thz)—C—NH$_2$ | 2 |
| #56 | Mpr—K—G—D—H(2,4-DNP)—P—C—NH$_2$ | 5 |
| #57 | Mpr—K—G—D—(2-Nal)—P—Pen—NH$_2$ | 1 |
| #58 | Mvl—K—G—D—W—P—Pen—NH$_2$ | 1 |
| #59 | Mpr—K—G—D—W—(Pip)—Pen—NH$_2$ | 1 |
| #60 | Mpr—(Har)—G—D—W—P—C—NH$_2$ | 0.15 |
| #61 | Mpr—K—G—D—W—P—C†—NH$_2$ | 15 |
| #62 | Mpr—K†—G—D—W—P—Pen—NH$_2$ | 2.5 |
| #63 | Mpr—(Har)—G—D—W—P—Pen—NH$_2$ | 0.10 |
| #64 | Mpr—(Acetimidyl—Lys)—G—D—W—P—C—NH$_2$ | 0.25 |
| #68 | Mpr—Har—Sar—D—W—P—C—NH$_2$ | 3.0 |
| #69 | Mpr—(Acetimidyl—Lys)—G—D—W—P—Pen—NH$_2$ | 0.5 |

EXAMPLE 18

Activity of Linear versus Cyclic Peptides

When tested for inhibition of fibrinogen binding to GP IIb–IIIa in the plate assay, linear RGDW-NH2 was very similar in activity to cyclic GCGRGDWPCA-NH$_2$ (FIG. 29A). In contrast, the linear KGDW-NH$_2$ was much less potent than cyclic GCGKGDWPCA-NH$_2$ (FIG. 29B). For the KGDW compounds, but not the RGDW compounds, cyclization resulted in a marked increase in the ability of the peptide to inhibit the binding of fibrinogen to GP IIb–IIIa.

EXAMPLE 19

Results of Plate Binding Assays for Synthetic Peptides

The peptides synthesized in Example 17, in addition to being assessed for the ability to inhibit platelet aggregation directly, were also tested in the plate assays of the invention as described above. The results for analogs 5,6,7, and 8 are shown in FIGS. 30C, 30D, 30E, 30A, and 30B respectively. As indicated in the figure, these analogs are differentially capable, to varying degrees, of inhibiting the binding of fibrinogen to GP IIb–IIIa as compared to vitronectin to vitronectin receptor. Analog #4 appears, among this group, to have the highest differential. Analogs #7 and #5, on the other hand, are also quite specific, and have excellent platelet aggregation inhibition activities.

EXAMPLE 20

Effects of Purified Peptides on Cell Adhesion

M21 melanoma cells were labelled with $^{35}$S-methionine, and then added to vitronectin-coated plates in the presence of the indicated concentrations of purified snake venom peptides. Cell attachment was measured by solubilizing the cells remaining after an incubation and wash, as described in Section C, on page 40. As shown in FIG. 31, neither barbourin nor Peptide 1 (truncated barbourin) had a significant effect on cell adhesion to vitronectin, although both are potent inhibitors of platelet aggregation as shown in Examples 2 and 3. In contrast, cotiarin, which is a potent inhibitor of vitronectin binding to the vitronectin receptor, was very potent in inhibiting cell attachment to vitronectin. In similar experiment, Peptide #3, Peptide #3 with K replaced by R (GCGRGDWPCA-NH$_2$) and RGDS were examined on M21 cell attachment to vitronectin. As shown in FIG. 32, RGDS and GCGRGDWPCA-NH2 are potent inhibitors of cell attachment whereas GCGKGDWPCA-NH$_2$ was ineffective up to 60 uM.

EXAMPLE 21

Comparison of Analogs 60 and 19

Analogs 60 and 19 described above are peptides of the invention containing the sequence K*GDX and are identical except for the embodiment of K*. Analog 60 is of the formula:

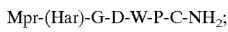

Mpr-(Har)-G-D-W-P-C-NH$_2$;

analog 9 is of the formula:

Mpr-K-G-D-W-P-C-NH$_2$.

These analogs were tested by standard platelet aggregation inhibition assays and using the cell adhesion assay of Example 20 above. The results are shown in FIGS. 33 and 34. As shown in FIG. 33, analog #60 is efficient at vanishingly small concentrations in inhibiting platelet aggregation, and is relatively less effective in preventing cell adhesion to victronectin. FIG. 34 shows analog #19 has good platelet aggregation inhibition activity as well as specificity; however, it is less active in the platelet aggregation inhibition assay than its analog #60 counterpart. Analog #60 has an IC$_{50}$ in platelet aggregation of approximately 0.15 nM; analog #19 has an IC$_{50}$ of approximately 1 nM.

EXAMPLE 22

Folt's Model of Thrombosis in Dog Coronary Artery

A. Initiation of cyclic flow reductions (CFRs) in open chest dog. An occluder placed on the left anterior descending (LAD) coronary artery of a 20 kg dog, as previously described was performed. The phasic and mean blood flows as measured by an elecromagnetic (EM) flow probe, and Doppler flow probe are shown in FIG. 35.

B. Effect of Cyclic GCGKGDWPCA-NH2 (Analog #3) on the CFRs in the open chest dog. A dose of 10 mg of this peptide was infused into a peripheral vein in the dog. Shown in FIG. 36 are the blood flow patterns in the LAD, as described above. Note the partial ablation of the CFRs, as seen in the decreased slope of the flow reductions. Note also that flow is not reduced to the same degree as in the control (A).

C. A second infusion of 40 mg of Analog #3 was given into a peripheral vein. As shown in FIG. 37 the complete ablation of the CFRs indicates that full flow has been restored in the LAD.

EXAMPLE 23

Construction of Expression Vectors for Barbourin Peptides

A gene encoding the full length [L$^{41}$] barbourin peptide (1–73) was assembled from synthetic oligonucleotides as shown in FIG. 38, which were kinased, annealed and ligated into EcoRI-HindIII digested M13mp18 using standard procedures. The bacterial alkaline phosphatase gene (phoA) signal sequence (Watson, M. E. E., *Nucleic Acids Research* (1984) 12:5145) was added to the barbourin construct by ligating synthetic oligonucleotides into the EcoRI/NcoI sites of the [L$^{41}$] barbourin (1–73) construct as shown in FIG. 39. The nucleotide sequences of all constructs were verified by the Sanger dideoxy chain termination method.

A truncated version of this peptide was also constructed from synthetic oligonucleotides which would encode only amino acids 28–73 of the full length molecule. Two alterations, Q$^{28}$ to E$^{28}$ and A$^{64}$ to C$^{64}$ were introduced using site directed mutagenesis as described by Kunkel et al. *Meth Enzymol* (1987) 154:367. The phoA signal sequence was added to the truncated version as described above (FIG. 40). In addition, the signal sequence for the *E. coli* heat-stable enterotoxin II (Picken, R. W., et al. *Infect Immun* (1983) 42:269) was added to the truncated version using synthetic oligonucleotides with EcoRI and NcoI compatible ends. All bacterial secretion constructs were subcloned into the bacterial expression vector pPROK-1 (Brosius, J., *Gene* (1984) 27:151, ibid:161), available commercially from CLONTECH Lab, Inc. using EcoRI and HindIII restriction endonucleases.

A gene encoding tandem repeats of the desired title peptide was prepared using the polymerase chain reaction (PCR) to produce the multimerization unit from the full-length barbourin peptide 1–73 containing L41 and C64.

FIG. 41A and 41B show the oligonucleotides used for the PCR synthesis. The PCR reaction was conducted according to the method of Saiki, R. K., et al. *Science* (1988) 239:487. The resulting polymer junction contains methionines at either end of the sequence as shown in FIG. 42 and provides desirable restriction sites for the construct.

The tandem repeats are formed from the individual multimer-forming components by, for example, ligating an EcoRI/BamHI fragment to a BglII/HindIII fragment in an M13mp18 vector cut with EcoRI/HindIII to form a dimer. The resultant dimer is excised with EcoRI and BamHI and religated to a BglII/HindIII fragment to produce a trimer, and so on until the desired size is obtained. This construction is diagramed in FIGS. 43A and 4B.

The multimer was then ligated into the *E. coli* vector pKK233-2, Amann, E., et al., *Gene* (1985) 40:183, available from Clontech, by digesting the vector with NcoI/HindIII and ligating a monomer subfragment of NcoI/BamHI and multimer subfragments of BglII/HindIII.

For expression as a fusion protein, the above digested vector was used along with an NcoI-EcoRI subfragment containing a slightly modified amino-terminal portion (amino acids 1 to 72) of the chloramphenicol acetyltransferase gene (Chang, C. N., et al. *Gene* (1987) 55:189) and EcoRI-HindIII subfragments of the multimer constructions.

EXAMPLE 24

Expression of Recombinant Genes

Protein expression from all of the recombinant plasmids described above is induced according to Kanamari et al. *Gene* (1988) 66:295 after transfection into appropriate *E. coli* host strains. Products are characterized by sodium dodecyl sulfate polyacrylamide gel electrophoresis and by their ability to inhibit ADP-induced platelet aggregation in platelet-rich plasma. Following purification, the multimeric proteins are converted to monomer units with cyanogen bromide cleavage and the products assayed as above.

We claim:

1. A DNA in isolated and purified form which encodes a PAI comprising naturally occurring protein amino acids, wherein said PAI:

comprises a KGD or RGD sequence,
   is active by a method for determining the presence of platelet aggregation inhibitor activity, which method comprises contacting said platelet aggregation inhibitor with purified platelet GP IIb-IIa in the presence of a solution of fibrinogen or von Willebrand Factor under conditions wherein fibrinogen or von Willebrand Factor binds to said GP IIb–IIIa and detecting the decrease in the binding of fibrinogen or von Willebrand Factor to GP IIb–IIIa in comparison to the binding of fibrinogen or von Willebrand Factor to GP IIb–IIIa in a control which does not contain said platelet aggregation inhibitor, and is a modified and/or truncated form of a PAI which is obtainable from a snake venom other than echistatin, trigramin, flavoviridin, elegantin, albolabrin, bitistatin, batroxostatin, halysin, applaggin, or derived from *Agkistrodon rhodostoma*, wherein said modified form differs from the native sequence by 1 to 10 conservative substitutions at other than the KGD or RGD sequence.

2. A recombinant expression system capable, when transformed into compatible host, of expressing the DNA of claim 1.

3. A recombinant host transformed with the expression system of claim 2.

4. A method to produce PAI which method comprises:
culturing the host of claim 3 under conditions effective to express the PAI-encoding DNA to produce PAI; and recovering the PAI from the culture.

5. A DNA in isolated and purified form which encodes a platelet aggregation inhibitor (PAI) comprising naturally occurring protein amino acids, wherein said PAI:

comprises a KGD or RGD sequence, is active by a method for determining the presence of platelet aggregation inhibitor activity, which method comprises contacting said platelet aggregation inhibitor with purified platelet GP IIb–IIIa in the presence of a solution of fibrinogen or von Willebrand Factor under conditions wherein fibrinogen or von Willebrand Factor binds to said GP IIb–IIIa and detecting the decrease in the binding of fibrinogen or von Willebrand Factor to GP IIb–IIIa in comparison to the binding of fibrinogen or von Willebrand Factor to GP IIb–IIIa in a control which does not contain said platelet aggregation inhibitor, and is a modified and/or truncated form of a PAI which is obtainable from a snake venom with the proviso that said venom is not from *Echis carinatus, Trimeresurus gramineus, T. flavoviridis, T. Elegans, T. albolabris, Bitis arietans, Bothrops atrox, Agkistrodon halys, Agkistrodon p. piscivorus*, or *Agkistrodon rhodostoma*, wherein said modified form differs from the native sequence by 1 to 10 conservative substitutions at other than the KGD or RGD sequence.

6. A recombinant expression system capable, when transformed into compatible host, of expressing the DNA of claim 5.

7. A recombinant host transformed with the expression system of claim 6.

8. A method to produce PAI which method comprises:
culturing the host of claim 7 under conditions effective to express the PAI-encoding DNA to produce PAI; and recovering the PAI from the culture.

9. A DNA in isolated and purified form which encodes a platelet aggregation inhibitor (PAI) comprising naturally occurring protein amino acids, said PAI being capable of inhibiting binding of fibrinogen or von Willebrand Factor to GP IIb–IIIa with substantially more potency than of inhibiting binding of vitronectin to vitronectin receptor or fibronectin to fibronectin receptor, which PAI comprises the amino acid sequence K*GDX, wherein X is an amino acid residue, and wherein K* is K.

10. A recombinant expression system capable, when transformed into a compatible host, of expressing a DNA encoding a specific platelet aggregation inhibitor (PAI) capable of inhibiting binding of Fg or vWF to GP IIb–IIIa with substantially more potency than of inhibiting binding of vitronectin to vitronectin receptor or fibronectin to fibronectin receptor, which PAI comprises the amino acid sequence KGDX, wherein X is an amino acid residue.

11. A recombinant host transformed with the expression system of claim 10.

12. A method to produce a GP IIb–IIIa specific PAI which method comprises:
culturing the host of claim 11 under conditions effective to express the PAI-encoding DNA to produce PAI; and recovering the PAI from the culture.

* * * * *